(12) United States Patent
Miyoshi

(10) Patent No.: US 8,142,348 B2
(45) Date of Patent: Mar. 27, 2012

(54) ENDOSCOPE INSERTION APPARATUS

(75) Inventor: Hiroaki Miyoshi, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/827,114

(22) Filed: Jun. 30, 2010

(65) Prior Publication Data

US 2011/0009696 A1    Jan. 13, 2011

Related U.S. Application Data

(63) Continuation of application No. PCT/JP2009/071030, filed on Dec. 17, 2009.

(30) Foreign Application Priority Data

Feb. 18, 2009    (JP) .................................. 2009-035744
Feb. 18, 2009    (JP) .................................. 2009-035745

(51) Int. Cl.
    *A61B 1/00*              (2006.01)
    *A61B 1/04*              (2006.01)

(52) U.S. Cl. .......................... 600/114; 600/106; 600/115

(58) Field of Classification Search .................. 600/104, 600/121, 127, 129, 130, 156, 177, 106, 114–116; 604/95.01–95.05, 104–109; 606/1, 50, 191, 606/192, 194, 197, 198

See application file for complete search history.

(56) References Cited

U.S. PATENT DOCUMENTS

| | | | | |
|---|---|---|---|---|
| 4,040,413 A | * | 8/1977 | Ohshiro | 600/116 |
| 4,066,070 A | * | 1/1978 | Utsugi | 600/116 |
| 4,207,872 A | * | 6/1980 | Meiri et al. | 600/116 |
| 4,389,208 A | * | 6/1983 | LeVeen et al. | 604/95.03 |
| 5,398,670 A | * | 3/1995 | Ortiz et al. | 600/114 |
| 5,595,565 A | * | 1/1997 | Treat et al. | 600/114 |
| 6,162,171 A | * | 12/2000 | Ng et al. | 600/141 |
| 6,263,248 B1 | * | 7/2001 | Farley et al. | 607/98 |
| 6,312,429 B1 | * | 11/2001 | Burbank et al. | 606/47 |
| 6,337,998 B1 | * | 1/2002 | Behl et al. | 607/101 |
| 6,468,298 B1 | * | 10/2002 | Pelton | 623/1.11 |
| 6,517,477 B1 | * | 2/2003 | Wendlandt | 600/114 |
| 6,716,179 B2 | * | 4/2004 | Burbank et al. | 600/564 |
| 6,988,986 B2 | * | 1/2006 | Gross | 600/114 |

(Continued)

FOREIGN PATENT DOCUMENTS

JP      56-135820      10/1981

(Continued)

OTHER PUBLICATIONS

International Search Report dated Feb. 18, 2009.

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

An endoscope insertion apparatus is provided that has an inner-side unit in which a plurality of inner-side fixing sections having an inner-side arm are uniformly arranged in a circumferential direction, an outer-side unit in which a plurality of outer-side fixing sections having an outer-side arm are uniformly arranged in a circumferential direction and in which slit portions that extend in a direction perpendicular to the circumferential direction and from which the inner-side arms protrude are uniformly arranged in the circumferential direction between the outer-side fixing sections, and an insertion operation portion that changes a front/rear relationship between the inner-side arms and outer-side arms.

13 Claims, 43 Drawing Sheets

U.S. PATENT DOCUMENTS

| | | | |
|---|---|---|---|
| 7,051,587 B2 * | 5/2006 | Simpson et al. | 73/152.54 |
| 2006/0095063 A1 * | 5/2006 | Sekiguchi | 606/192 |
| 2006/0287666 A1 * | 12/2006 | Saadat et al. | 606/198 |
| 2009/0062608 A1 * | 3/2009 | Miyoshi | 600/115 |
| 2010/0145143 A1 * | 6/2010 | Salomon et al. | 600/104 |
| 2010/0268029 A1 * | 10/2010 | Phan et al. | 600/115 |

FOREIGN PATENT DOCUMENTS

| | | |
|---|---|---|
| JP | 59-181124 | 10/1984 |
| JP | 07-100127 | 4/1995 |
| JP | 2001-315636 | 11/2001 |
| JP | 2002-065595 | 3/2002 |
| JP | 2002-301019 | 10/2002 |
| JP | 2006-110309 | 4/2006 |
| JP | 2007-330467 | 12/2007 |
| JP | 2008-284322 | 11/2008 |

* cited by examiner

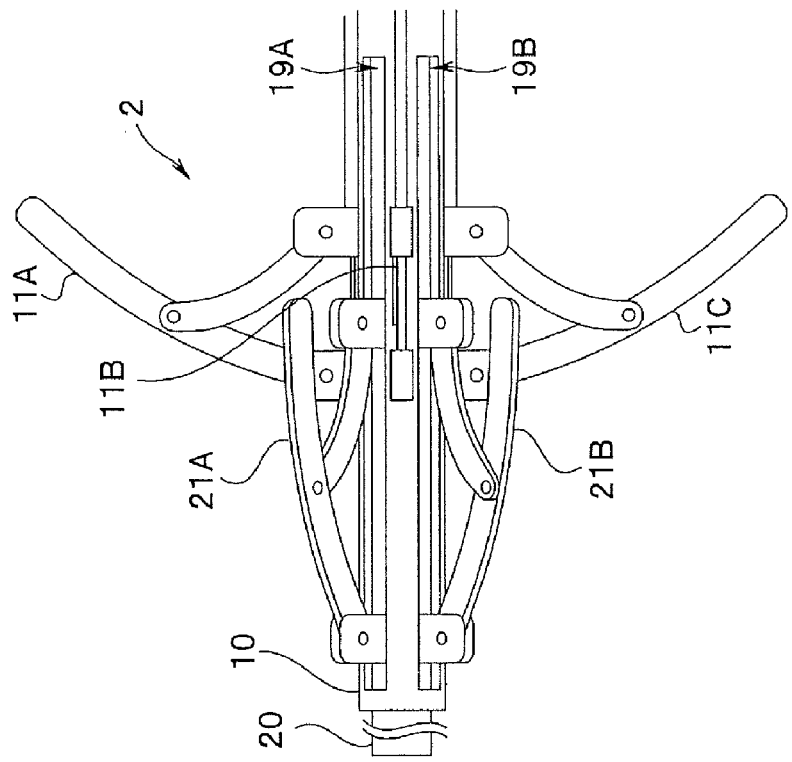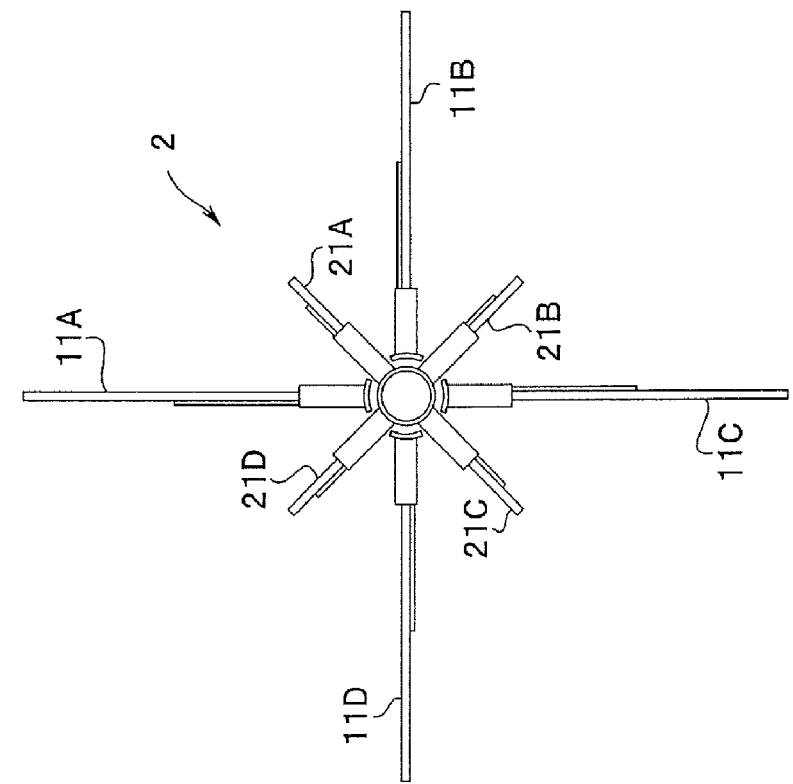

ENDOSCOPE INSERTION APPARATUS

CROSS REFERENCE TO RELATED APPLICATION

This application is a continuation application of PCT/JP2009/071030 filed on Dec. 17, 2009 and claims benefit of Japanese Applications No. 2009-035744 filed in Japan on Feb. 18, 2009, No. 2009-035745 filed in Japan on Feb. 18, 2009, the entire contents of each of which are incorporated herein by their reference.

BACKGROUND OF THE INVENTION

1. Field of the Invention

The present invention relates to an insertion apparatus for inserting an endoscope having an image pickup section into a duct. More particularly, the present invention relates to an endoscope insertion apparatus that includes an inner-side insertion assisting section and an outer-side insertion assisting section, in which each insertion assisting section is equipped with a fixing member that can be fixed to a duct wall.

2. Description of the Related Art

An endoscope has an insertion portion that includes an elongated flexible portion, a bendable bending portion that is connected to a distal end side of the flexible portion, and a distal end portion that is connected to a distal end side of the bending portion. The insertion portion of the endoscope is, for example, anally inserted into a body cavity of a subject to conduct observation and diagnosis of a predetermined region or conduct treatment while observing the predetermined region.

However, when a conventional endoscope is inserted as far as a deep region of a digestive tract, for example, when the endoscope is inserted as far as the small intestine via the large intestine, it is difficult to insert the endoscope to the deep part by merely pushing in the insertion portion because it is hard for the force to be transmitted to the distal end portion due to complicated bends in the intestinal tract. Consequently, when an endoscope is inserted into the large intestine, operations such as angle adjusting, twisting, retracting, and axis retaining are performed, and combined use of air feeding and x-ray fluoroscopy and the like is also performed.

In order to facilitate the insertion operation described above, endoscopes having fixing balloons have been proposed.

For example, Japanese Patent Application Laid-Open Publication No. 2002-65595 discloses a double-balloon endoscope that has two tubes, in which each tube includes a balloon portion that is provided near a distal end of the tube and which can be inflated and deflated by means of fluid, a fluid channel that communicates with the balloon portion, and a fluid feeding apparatus which is provided at a proximal end portion of the tube and communicates with the fluid channel.

Further, Japanese Patent Application Laid-Open Publication No. 2002-301019 discloses a sliding-tube type endoscope that includes an endoscope body that is provided with a balloon for fixation of the endoscope body at an outer circumferential portion of the distal end thereof, and an overtube that is provided with a balloon for fixation of the tube at an outer circumferential portion of the distal end thereof and into which the endoscope body is inserted.

FIG. 1 is a view that illustrates procedures for inserting a double-balloon endoscope into an intestinal tract 9A. According to the double-balloon endoscope, an overtube 240a can be fixed to an intestinal wall 9 of the intestinal tract 9A by a balloon 230a that is attached to the distal end thereof, and an endoscope 202a can be fixed to the intestinal wall 9 by a balloon 230b that is attached to the distal end thereof. Therefore, by repeating an operation whereby the endoscope 202a advances to the deep part side and the overtube 240a thereafter progresses by the amount that the endoscope 202a has advanced while the balloon 230a and the balloon 230b are alternately fixed to the intestinal wall 9 in accordance with the procedures illustrated in FIG. 1(A) to (H), the endoscope 202a arrives at a deep part of the large intestine or the small intestine.

FIG. 2 is a view for describing a method of inserting a double-balloon endoscope. FIG. 3 and FIG. 4 are views for describing a method of inserting a sliding-tube type endoscope.

Regions such as the sigmoid colon and transverse colon of the large intestine are free regions at which the intestinal tract 9A is not fixed to the abdominal cavity and at which the intestinal tract 9A can freely move inside the abdominal cavity. Therefore, in some cases the double-balloon endoscope cannot be inserted well at a free region. As shown in FIG. 2A, when a double-balloon endoscope is used, first, a balloon 230b attached to an endoscope 202a is inserted to a deep side. Next, as shown in FIG. 2B, the balloon 230b is inflated so that the balloon 230b is fixed to the intestinal wall 9. Subsequently, as shown in FIG. 2C, it is attempted to glide a balloon 230a that is attached to an overtube 240a along the inside of the intestine to approach the balloon 230b at the deep part side. However, in this case, if there is a large amount of friction between the intestinal wall 9 and the balloon 230a, the intestinal tract 9A shortens into a bellows-like shape. As a result, although the distance between the balloon 230a and the balloon 230b is shortened, the overtube 240a is not moved relative to the intestinal wall 9.

Next, as shown in FIG. 2D, the balloon 230a is inflated and fixed to the intestinal wall 9, and the balloon 230b is deflated. The surgeon then attempts to advance the balloon 230b towards a deep region by extending the endoscope 202a. However, even in the deflated state, the balloon 230b slips inside the intestine and does not move due to friction between the balloon 230b and the intestinal wall 9. Consequently, the intestinal tract 9A that has been shortened into a bellows-like shape is stretched back into its original state. More specifically, since the intestinal tract 9A returns from the state in FIG. 2D to the state in FIG. 2A, the endoscope 202a cannot move in the direction of the deep region of the intestinal tract 9A.

On the other hand, in the case of a sliding-tube type endoscope also, there are cases in which the sliding-tube type endoscope cannot be inserted well at a free region. As shown in FIG. 3A, according to a sliding tube method, the surgeon initially inserts an endoscope 302a as far as a region to which the endoscope 302a can be inserted without difficulty. Next, as shown in FIG. 3B, the surgeon inflates a balloon 330b to fix the balloon 330b to the intestinal wall 9, and pushes in an overtube 340a that has a balloon 330a to feed the overtube 340a to the deep region side. However, if the balloon 330a does not move while sliding with respect to the intestinal wall 9, even if the surgeon pushes in the overtube 340a in the direction of the deep region, the only result is that the intestinal tract 9A is shortened into a bellows-like shape between the balloon 330a and the balloon 330b. Consequently, as shown in FIG. 3C, when the balloon 330b is deflated, the intestinal tract 9A that had been shortened expands. More specifically, since the intestinal tract 9A returns to the state in FIG. 3A from the state in FIG. 3C, the surgeon cannot move the endoscope 302a in the direction of the deep region of the intestinal tract 9A.

Further, according to the sliding-tube type endoscope, the endoscope insertion portion is used in combination with the overtube 340a. Therefore, as shown in FIG. 4, an operation by which a surgeon pushes the endoscope into a deep region of the intestinal tract 9A using a hand 115 or the like is performed via the overtube 340a that covers the endoscope 302a.

SUMMARY OF THE INVENTION

An endoscope insertion apparatus according to an embodiment of the present invention is an endoscope insertion apparatus for inserting an endoscope into a duct, that includes: an inner-side insertion assisting section in which inner-side arm members that press a duct wall are uniformly arranged in a circumferential direction on a distal end side of an inner-side insertion assisting section body portion; and an outer-side insertion assisting section in which outer-side arm members that press the duct wall are uniformly arranged in a circumferential direction on a distal end side of an outer-side insertion assisting section body portion, and which is mounted on an outer circumferential portion of the inner-side insertion assisting section so that the inner-side arm members and the outer-side arm members are alternately arranged in the circumferential direction, and which advances and retracts on a same axis as the inner-side insertion assisting section; wherein distal end portions of the outer-side arm members and distal end portions of the inner-side arm members can be moved to an overlapping state in the insertion direction or can be moved to a state in which the distal end portions of the outer-side arm members and the distal end portions of the inner-side arm members move forward and rearward with respect to each other in the insertion direction.

BRIEF DESCRIPTION OF THE DRAWINGS

FIG. 12A is an exterior view of the endoscope insertion apparatus according to the first embodiment, that is a view as observed from the distal end side;

FIG. 12B is an exterior side view of the endoscope insertion apparatus according to the first embodiment;

FIG. 59 is a side schematic view of the endoscope insertion apparatus according to the second embodiment;

FIG. 60 is a side schematic view of the endoscope insertion apparatus according to the second embodiment;

FIG. 61A is a side schematic view for describing a method of using the endoscope insertion apparatus according to the second embodiment;

FIG. 61B is a side schematic view for describing a method of using the endoscope insertion apparatus according to the second embodiment;

FIG. 61C is a side schematic view for describing a method of using the endoscope insertion apparatus according to the second embodiment;

FIG. 61D is a side schematic view for describing a method of using the endoscope insertion apparatus according to the second embodiment;

FIG. 62 is an oblique perspective view of an endoscope insertion apparatus according to a third embodiment;

FIG. 63A is a view of the endoscope insertion apparatus according to the third embodiment as seen from the insertion axis direction, that shows a state when a diameter is expanded;

FIG. 63B is a view of the endoscope insertion apparatus according to the third embodiment as seen from the insertion axis direction, that shows a state when the diameter is reduced;

FIG. 64A is a view for describing a method of withdrawing the endoscope insertion apparatus according to the third embodiment from the intestine, as seen from a direction perpendicular to the insertion axis;

FIG. 64B is a view for describing a method of withdrawing the endoscope insertion apparatus according to the third embodiment from the intestine, as seen from a direction perpendicular to the insertion axis;

FIG. 64C is a view for describing a method of withdrawing the endoscope insertion apparatus according to the third embodiment from the intestine, as seen from a direction perpendicular to the insertion axis;

Figure 65:
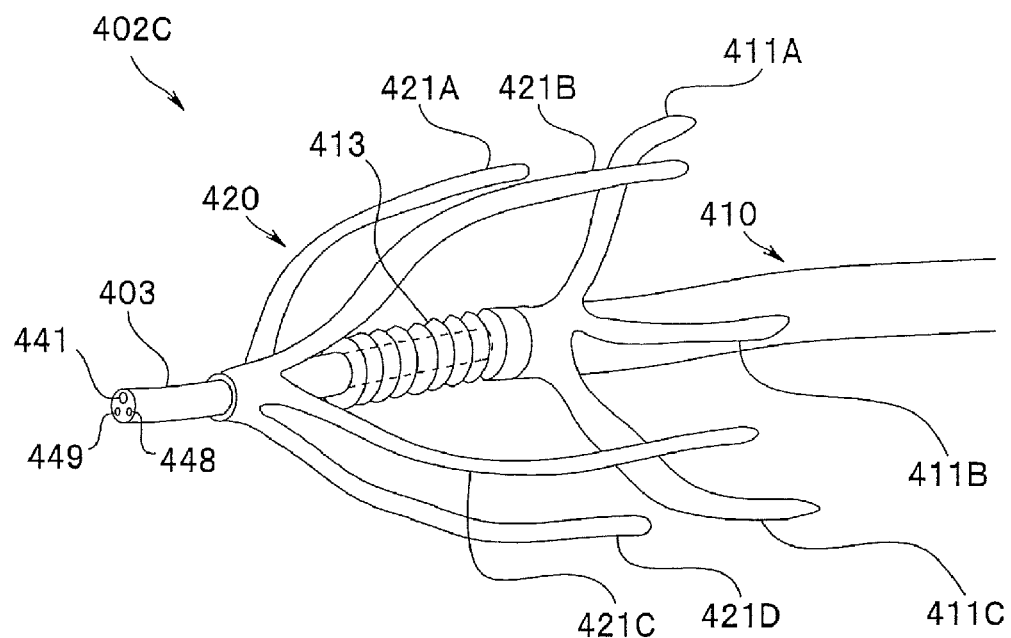
Figure 66:
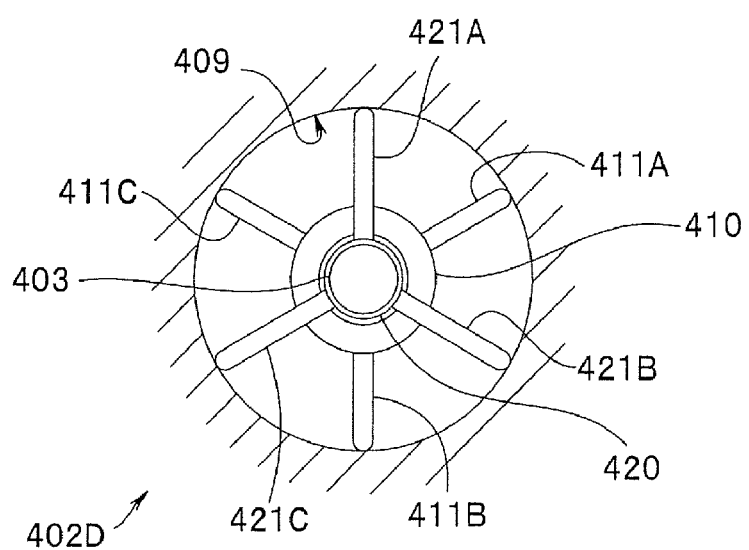
Figure 67:
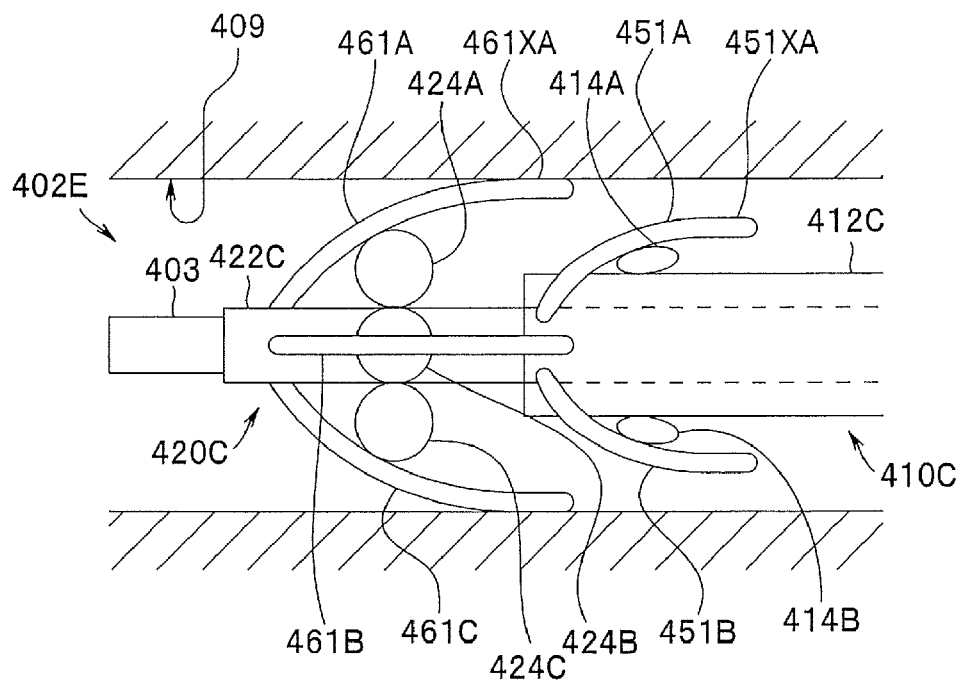
Figure 68:
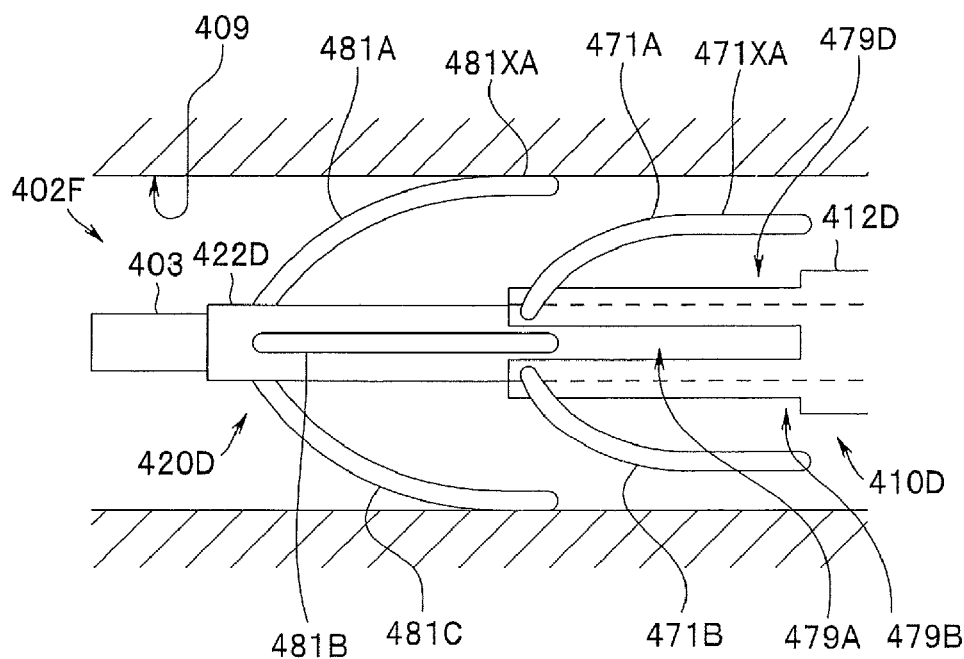

FIG. 65 is an oblique perspective view of an endoscope insertion apparatus according to a fourth embodiment;

FIG. 66 is a front view of an endoscope insertion apparatus according to a fifth embodiment;

FIG. 67 is a schematic diagram as viewed from a lateral direction of an endoscope insertion apparatus according to a sixth embodiment in a state in which the endoscope insertion apparatus is inserted inside the intestine; and FIG. 68 is a schematic diagram as viewed from a lateral direction of an endoscope insertion apparatus according to a seventh embodiment in a state in which the endoscope insertion apparatus is inserted inside the intestine.

DETAILED DESCRIPTION OF THE PREFERRED EMBODIMENTS

First Embodiment

Hereunder, an endoscope insertion apparatus (hereafter, referred to as "insertion apparatus") 2 according to the first embodiment of the present invention is described referring to the drawings.

Figure 1:
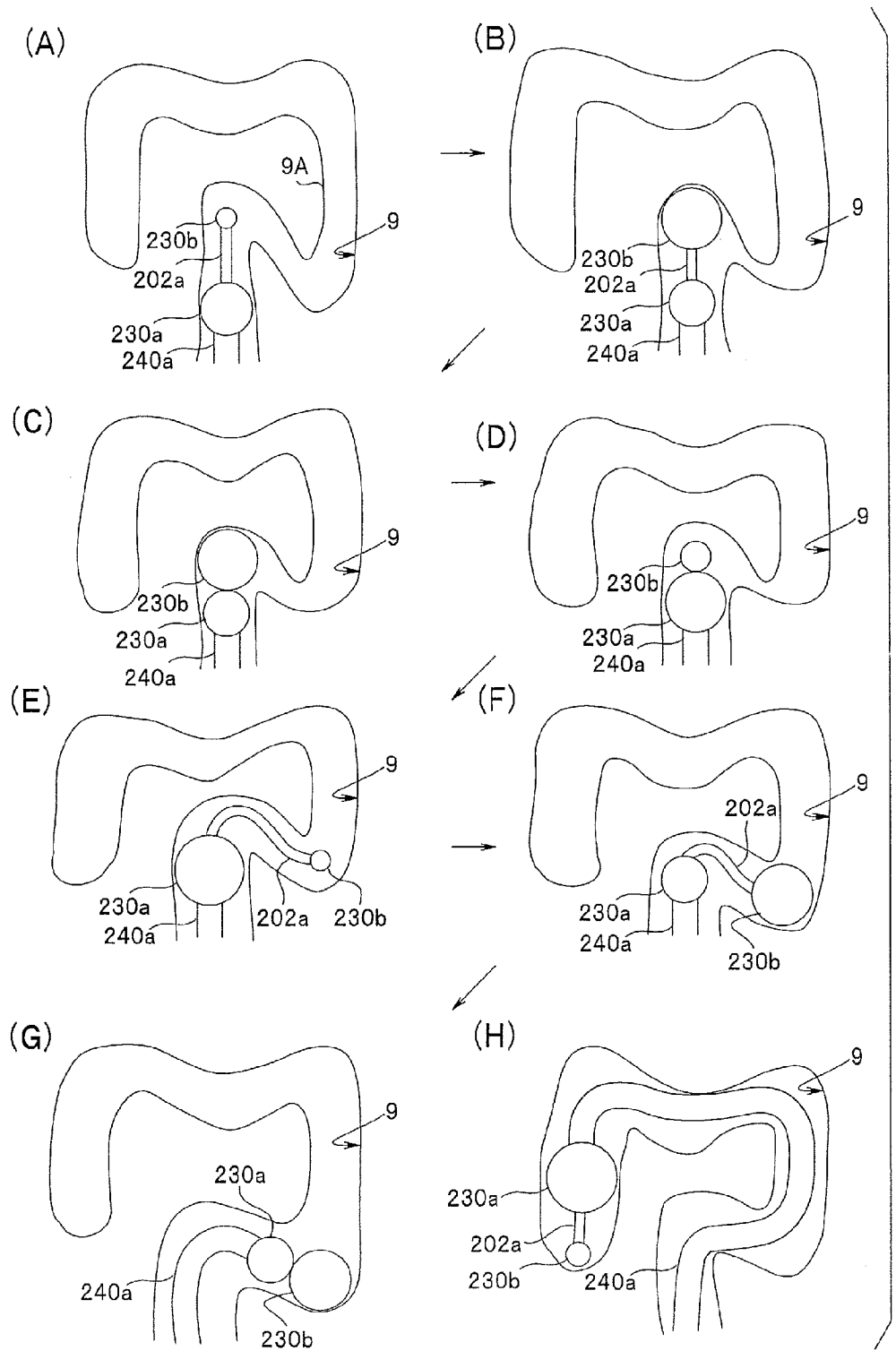
FIG. 1 is a view that illustrates procedures for inserting a double-balloon endoscope into the large intestine.
Figure 2A:
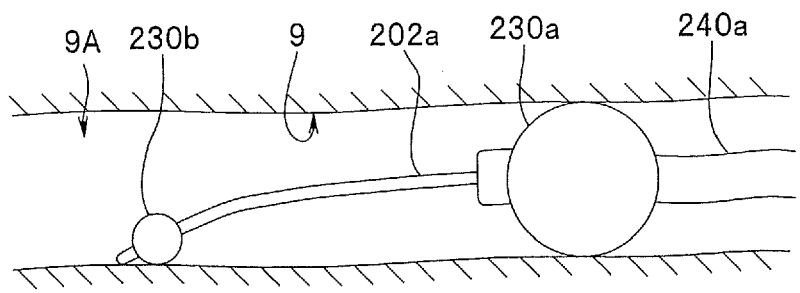
FIG. 2A is a view for illustrating a problem when inserting a double-balloon endoscope.
Figure 2B:
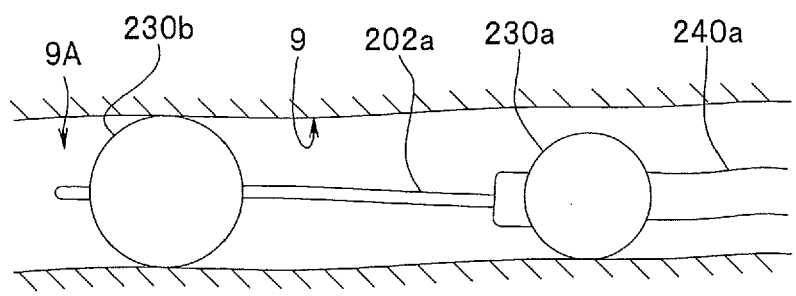
FIG. 2B is a view for illustrating a problem when inserting a double-balloon endoscope.
Figure 2C:
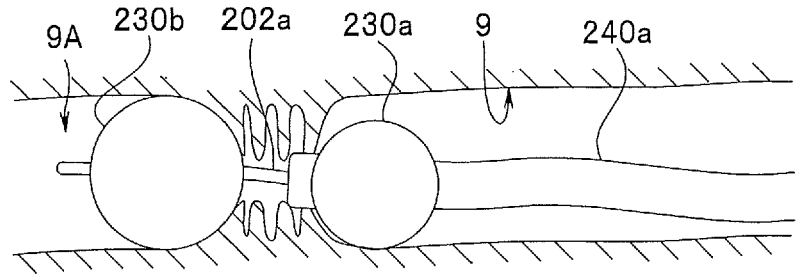
FIG. 2C is a view for illustrating a problem when inserting a double-balloon endoscope.
Figure 2D:
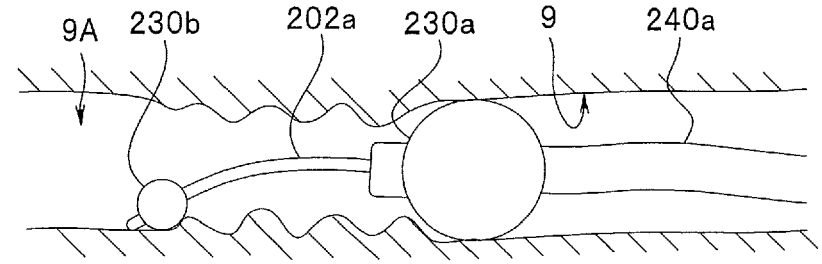
FIG. 2D is a view for illustrating a problem when inserting a double-balloon endoscope.
Figure 3A:
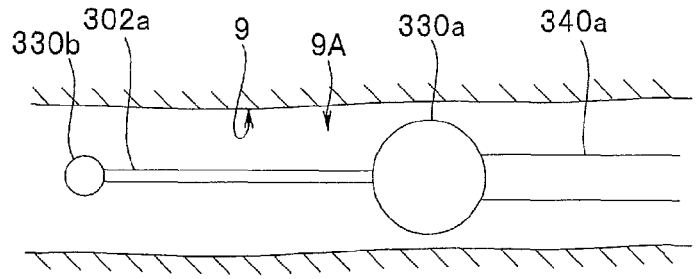
FIG. 3A is a view for illustrating a problem when inserting a sliding-tube type endoscope.
Figure 3B:
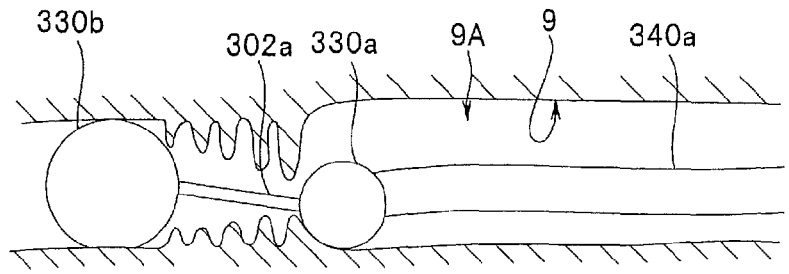
FIG. 3B is a view for illustrating a problem when inserting a sliding-tube type endoscope.
Figure 3C:
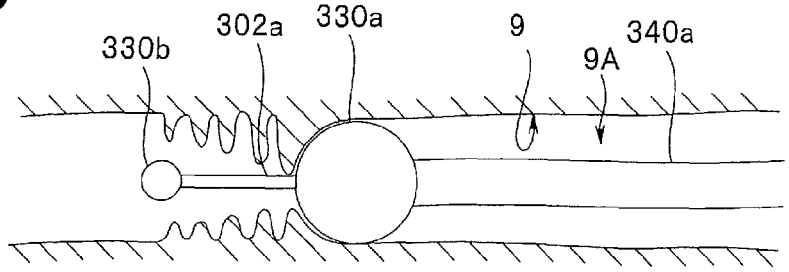
FIG. 3C is a view for illustrating a problem when inserting a sliding-tube type endoscope.
Figure 4:
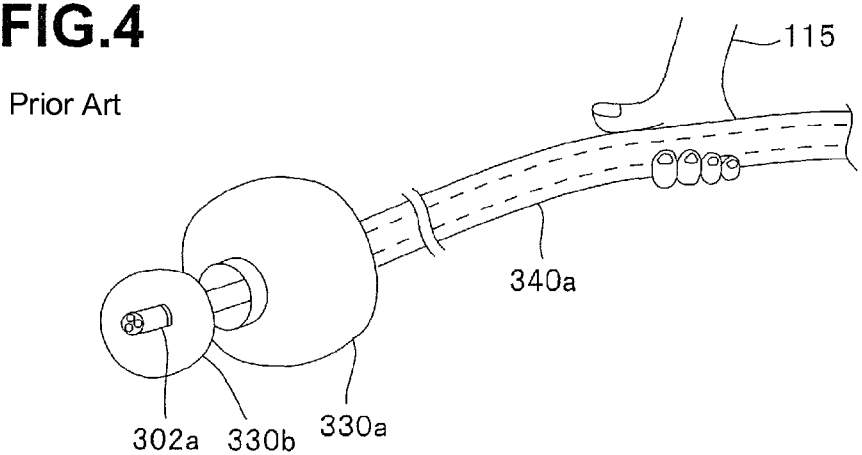
FIG. 4 is a view for illustrating a way of handling a sliding-tube type endoscope.
Figure 5:
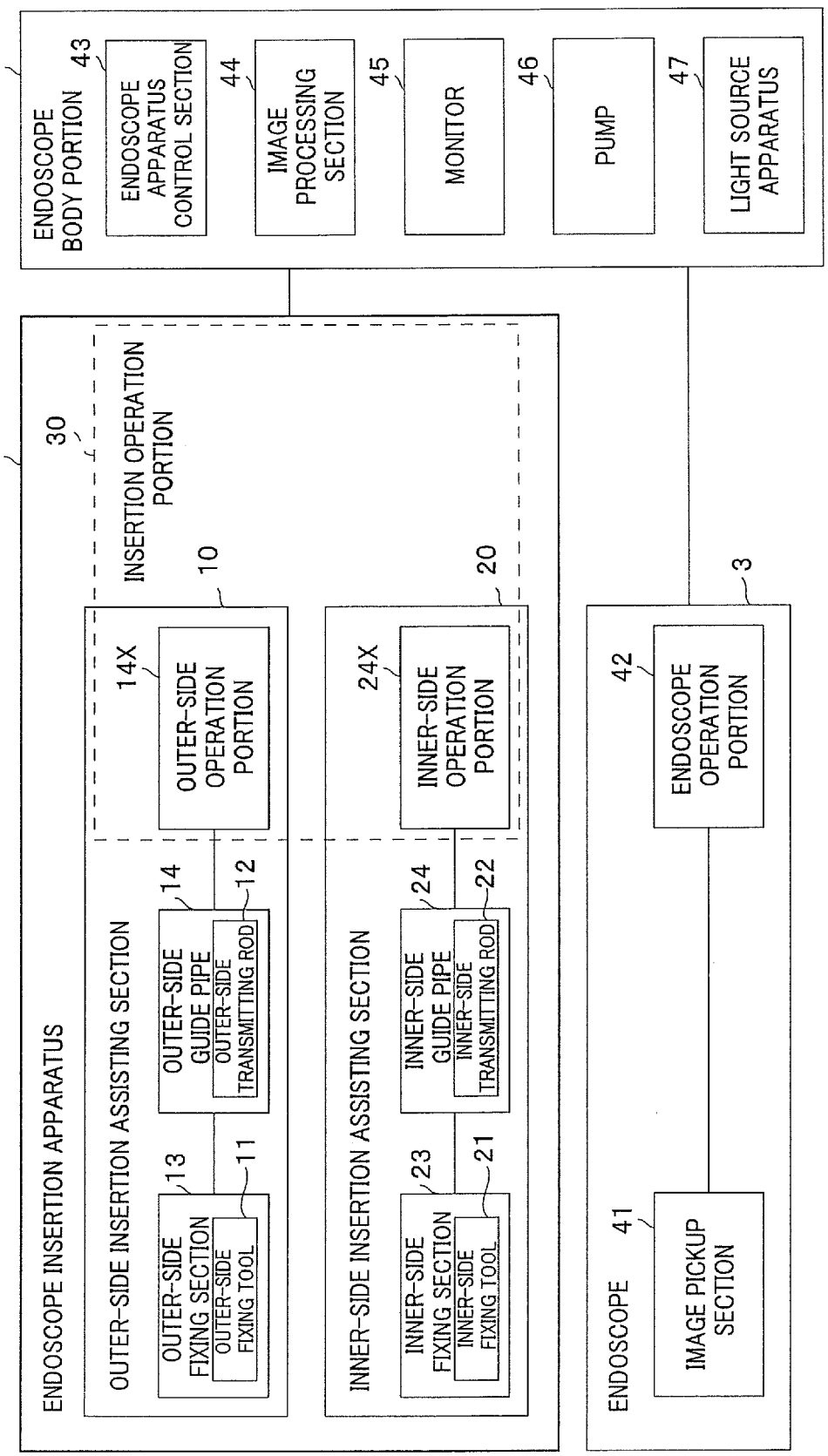
FIG. 5 is an overall configuration diagram of an endoscope apparatus that includes an endoscope insertion apparatus according to a first embodiment.

As shown in FIG. 5, an endoscope apparatus 1 includes an endoscope 3, an insertion apparatus 2 for inserting a distal end portion of the endoscope 3 into a deep region of an intestinal tract 9A of a patient as an object to be examined, and an endoscope body portion 4. More specifically, the insertion apparatus 2 of the present embodiment is a so-called "over-tube-type endoscope insertion apparatus" through which an insertion portion of the endoscope 3 that has an image pickup section 41 and an endoscope operation portion 42 can be inserted.

The endoscope body portion 4 has an endoscope apparatus control section 43, an image processing section 44, a monitor 45, a pump 46, and a light source apparatus 47. The endoscope apparatus control section 43 performs control of the endoscope apparatus 1. The image processing section 44 processes signals of images that have been photographed by the image pickup section 41 provided at the distal end portion of the endoscope 3. The monitor 45 displays images that have been processed by the image processing section 44. The pump 46, for example, feeds air or feeds water into the intestinal tract 9A through an opening 48 (see FIG. 6) in the distal end portion of the endoscope 3, or sucks a fluid from inside the intestinal tract 9A. An illuminating light of the light source apparatus 47 is guided as far as an illumination section 49 (see FIG. 6) of the distal end portion of the endoscope 3.

The insertion apparatus 2 includes an inner-side insertion assisting section (hereunder, referred to as "inner-side unit") 20, an outer-side insertion assisting section (hereunder referred to as "outer-side unit") 10, and an insertion operation portion 30. The inner-side unit 20 includes an inner-side fixing section 23 that has an inner-side arm member (hereunder, referred to as "inner-side arm") 21, an inner-side transmitting rod 22 as an inner-side operation transmitting section that is flexible, and an inner-side guide pipe 24 that is flexible and which allows the inner-side transmitting rod 22 to pass therethrough, and an inner-side operation portion 24X to which the inner-side guide pipe 24 and the inner-side transmitting rod 22 are connected. The outer-side unit 10 includes an outer-side fixing section 13 that has an outer-side arm member (hereunder, referred to as "inner-side arm") 11, an outer-side transmitting rod 12 as an outer-side operation transmitting section that is flexible, an outer-side guide pipe 14 that is flexible and which allows the outer-side transmitting rod 12 to pass therethrough, and an outer-side operation portion 14X to which the outer-side guide pipe 14 and the outer-side transmitting rod 12 are connected. More specifically, the inner-side operation portion 24X is connected to the inner-side unit 20 and the outer-side operation portion 14X is connected to the outer-side unit 10.

As described later, not only can the surgeon perform an operation to change the state of the inner-side arms 21 or outer-side arms 11 between an expanded diameter state and a reduced diameter state by operating the inner-side operation portion 24X or outer-side operation portion 14X as the insertion operation portion 30, but the surgeon can also change the relative positions of the inner-side unit 20 and the outer-side unit 10 by operating the insertion operation portion 30 to change the front/rear relationship with respect to the insertion direction, i.e. the direction perpendicular to the circumferential direction, between the inner-side arms 21 and the outer-side arms 11. Further, by operating the insertion operation portion 30 the surgeon can also move the entire inner-side unit 20 and outer-side unit 10 with respect to the insertion direction.

Figure 6:
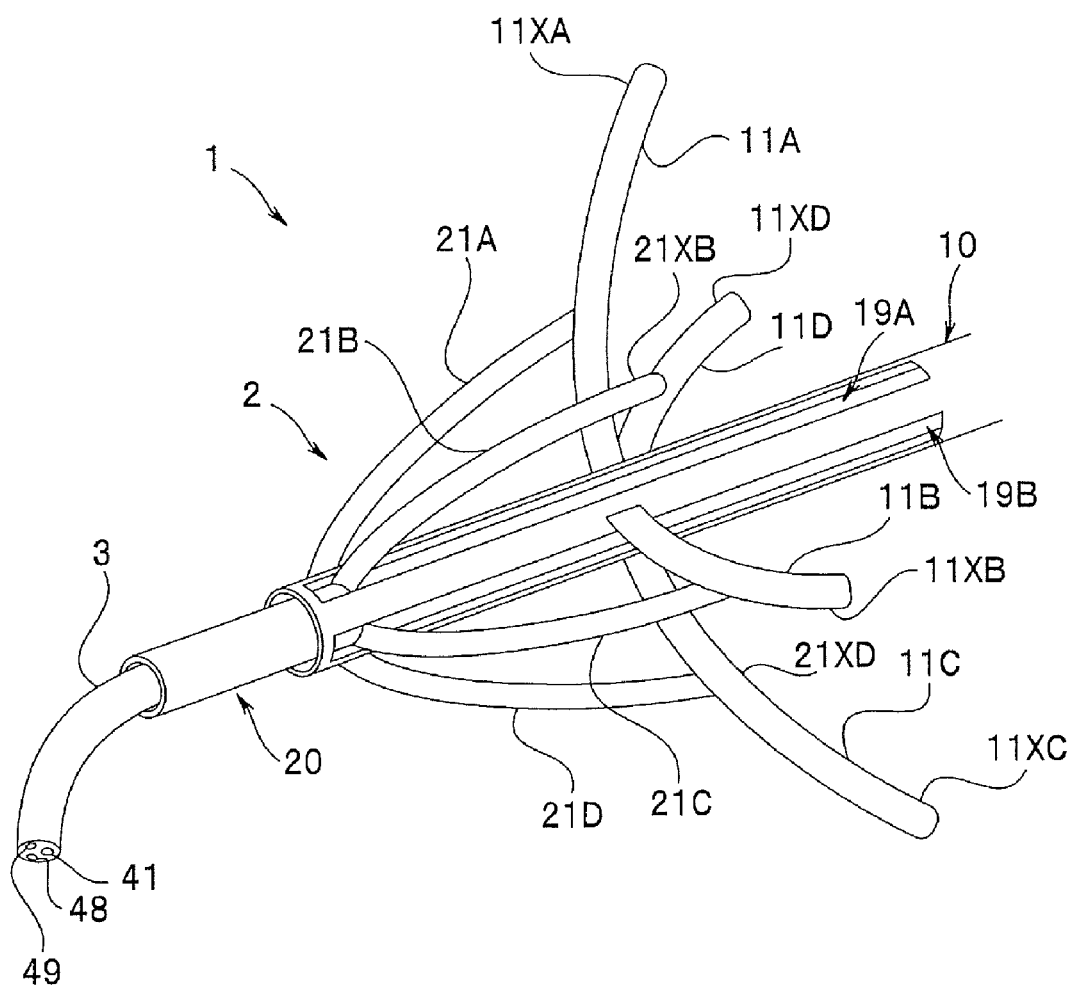
FIG. 6 is a perspective view of the external appearance when the endoscope insertion apparatus of the first embodiment is joined to an endoscope.

Next, the structure of the insertion apparatus 2 is described using FIG. 6. As described later, in order to simplify the illustration in FIG. 6, the detailed structure of the inner-side fixing section 23 (see FIG. 7A, FIG. 7B, FIG. 8A, and FIG. 8B) and the outer-side fixing section 13 and the like is not illustrated in FIG. 6.

As shown in FIG. 6, the endoscope 3 is inserted through the inside of the inner-side unit 20 and fixed to the inner-side unit 20. The outer-side unit 10 is mounted in a movable condition to an outer circumferential portion of the inner-side unit 20. Consequently, the outer-side unit 10 is movable in the axial direction of the inner-side unit 20 on the outer circumferential portion of the inner-side unit 20, more specifically, in a direction (insertion direction) perpendicular to the circumferential direction. In other words, the outer-side unit 10 can move on the same axis as the inner-side unit 20. Four inner-side arms 21A to 21D that protrude in a radial shape are provided in an equally spaced manner in the circumferential direction on the outer circumferential portion of the inner-side unit 20. Further, slit portions 19A to 19D through which the inner-side arms 21A to 21D can protrude are formed between the four outer-side arms 11A to 11D in the outer circumferential portion of the outer-side unit 10.

Consequently, the outer-side unit 10 can move forward and rearward with respect to the insertion direction by the amount of the length of the slit portions 19A to 19D that extend in the axial direction on the outer circumferential portion of the inner-side unit 20. Further, from the opposite viewpoint, the inner-side unit 20 can move forward and rearward with respect to the insertion direction by the amount of the length of the slit portions 19A to 19D at the inner circumferential portion of the outer-side unit 10. As a result, it is possible to change the front/rear relationship with respect to the insertion direction between the inner-side arms 21A to 21D and the outer-side arms 11A to 11D, that is, the front and rear positional relationship that indicates whether the inner-side arms 21A to 21D or the outer-side arms 11A to 11D are positioned further on the distal end portion side. In this connection, the relative relationship between the outer-side unit 10 and the inner-side unit 20 is manipulated by means of the insertion operation portion 30.

Although according to FIG. 6 the outer-side arms 11A to 11D, that is, the outer-side fixing section 13 (see FIG. 7A and FIG. 7B) are provided in the vicinity of the center in the longitudinal direction of the slit portions 19A to 19D, the present invention is not limited thereto. It is sufficient for the outer-side arms 11A to 11D to be provided inside the range in the longitudinal direction of the slit portions 19A to 19D. For example, the outer-side arms 11A to 11D may be provided at a portion that is further toward the front with respect to the insertion direction of the slit portions 19A to 19D.

The outer-side arms 11A to 11D and the inner-side arms 21A to 21D can be changed between an expanded diameter state and a reduced diameter state, respectively. In FIG. 6, a case is illustrated in which the outer-side arms 11A to 11D are in an expanded diameter state and the inner-side arms 21A to 21D are in a reduced diameter state. When the outer-side arms 11A to 11D or the inner-side arms 21A to 21D are in an expanded diameter state, the distal end portions thereof are pressed against the intestinal wall 9.

As described in the foregoing, the outer-side unit 10 has four slit portions 19A to 19D in the outer circumferential portion thereof. The inner-side arms 21A to 21D of the inner-side unit 20 protrude in a radial shape through windows of the slit portions 19A to 19D, and the inner-side arms 21A to 21D and the outer-side arms 11A to 11D are alternately disposed in the circumferential direction of an axis of advancement and retraction. As a result, because of the existence of the slit portions 19A to 19D, distal end portions of the inner-side arm members (hereunder, referred to as "inner-side distal end portions") 21XA to 21XD are movable in the forward and rearward directions with respect to the insertion direction of the distal end portions of the outer-side arm members (hereunder, referred to as "outer-side distal end portions") 11XA to 11XD. More specifically, the slit portions 19 are window portions formed in the outer circumferential portion of the outer-side unit 10 parallel to the longitudinal direction of the insertion apparatus 2.

In this case, although a structure in which the distal end portion side of the slit portions 19 is provided as an open end is necessary in order to attach and detach the outer-side unit 10 to and from the inner-side unit 20, this structure is not necessary after the outer-side unit 10 has been mounted to the outer circumferential portion of the inner-side unit 20. Therefore, when it is not necessary to attach and detach the outer-side unit 10 to and from the inner-side unit 20, the slit portions 19 may be elongated window portions in a roughly rectangular shape whose distal end portion side is closed. In other words, the slit portions 19 may be shaped like a window in a side surface of a tubular member of the outer-side unit 10 for which the axial direction is the longitudinal direction.

After mounting the outer-side unit 10 to the outer circumferential portion of the inner-side unit 20, for example, a ring-shaped member may be provided that fixes an open end of the distal end portion side of the slit portions 19 and closes the open end. More specifically, it is sufficient for the endoscope insertion apparatus to have elongated window portions of a length that is adequate for the inner-side distal end portions 21X and the outer-side distal end portions 11X to move forward and rearward relatively with respect to the insertion direction while passing each other.

Hereunder, when each of a plurality of components that have the same structure is referred to, one alphabet character at the end of the symbol thereof is omitted. For example, when the inner-side fixing sections 23A to 23D, the outer-side fixing sections 13A to 13D, the inner-side arms 21A to 21D, or the outer-side arms 11A to 11D are referred to, the terms "inner-side fixing sections 23", "outer-side fixing sections 13", "inner-side arms 21", and "outer-side arms 11", respectively, are used. Further, regarding similar components that are possessed by both the outer-side unit 10 and the inner-side unit 20, in some cases hereunder a description is given with respect to only the components of one of the outer-side unit 10 and the inner-side unit 20.

Figure 7A:
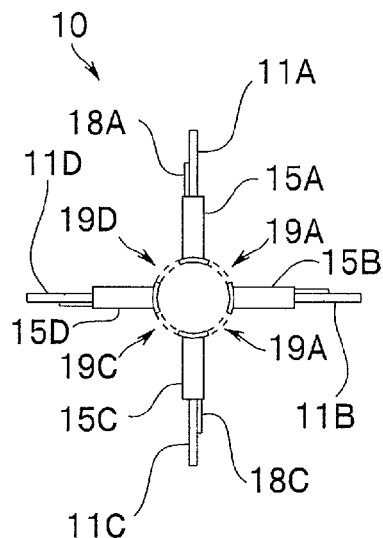
FIG. 7A is an exterior view of an outer-side insertion assisting section according to the first embodiment, that is a view as observed from the distal end side.
Figure 7B:
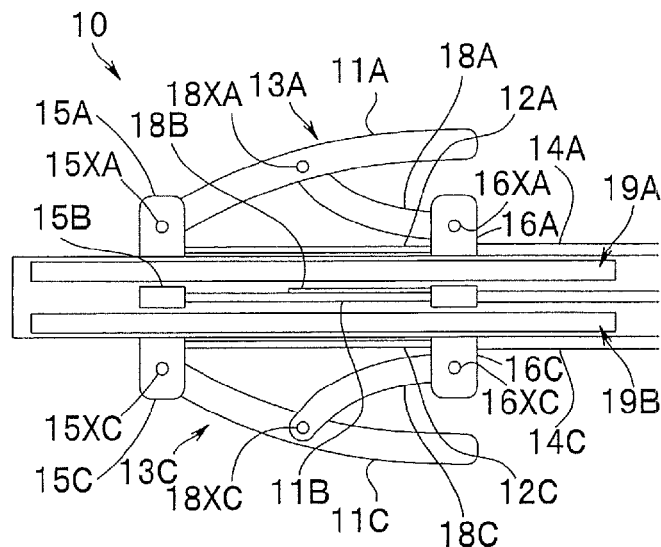
FIG. 7B is an exterior side view of the outer-side insertion assisting section according to the first embodiment.

Next, the structure of the outer-side unit 10 and the inner-side unit 20 is described using FIG. 7A to FIG. 8B. As shown in FIG. 7A and FIG. 7B, each of the four outer-side fixing sections 13 of the outer-side unit 10 can cause an outer-side arm 11 to change between an expanded diameter state and a reduced diameter state by means of a link mechanism formed by a single outer-side arm 11, a movement supporting portion 15 that has a pivot 15X that is a second pivot, a fixed support portion 16 that has a pivot 16X, and a link portion 18 that has a pivot 18X in the vicinity of the center thereof.

The inner circumferential part of the outer-side unit 10 is a space through which the inner-side unit 20 can be inserted. The slit portions 19 are formed between the outer-side fixing sections 13 that are uniformly arranged on the outer circumferential portion of the outer-side unit 10. Further, outer-side transmitting rods 12 for performing operations to push or pull movement supporting portions 15 are connected to respective movement supporting portions 15. On the proximal end portion side, each outer-side transmitting rod 12 is inserted through the inside of a hollow outer-side guide pipe 14.

Figure 8A:
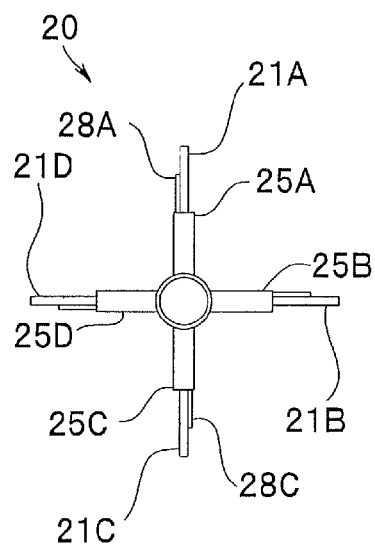
FIG. 8A is an exterior view of an inner-side insertion assisting section according to the first embodiment, that is a view as observed from the distal end side.
Figure 8B:
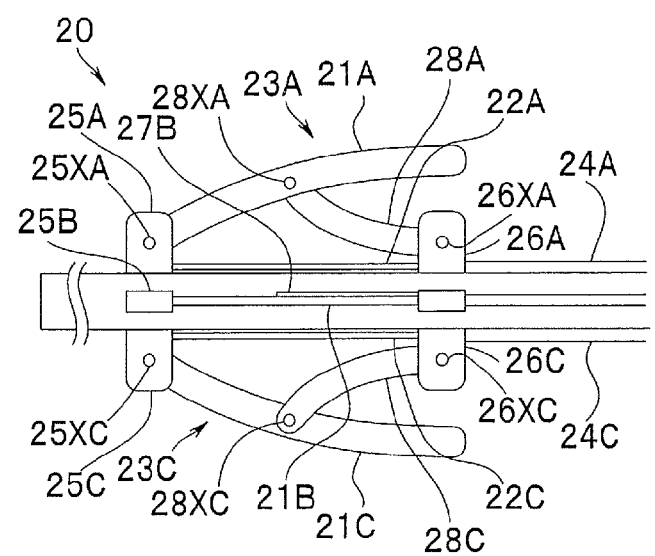
FIG. 8B is an exterior side view of the inner-side insertion assisting section according to the first embodiment.

As shown in FIG. 8A and FIG. 8B, the structure of the inner-side unit 20 resembles the structure of the outer-side unit 10. More specifically, each of the four inner-side fixing sections 23 of the inner-side unit 20 can cause an inner-side arm 21 to change between an expanded diameter state and a reduced diameter state by means of a link mechanism formed by a single inner-side arm 21, a movement supporting portion 25 that has a pivot 25X that is a first pivot, a fixed support portion 26 that has a pivot 26X, and a link portion 28 that has a pivot 28X in the vicinity of the center thereof.

The inner circumferential part of the inner-side unit 20 is a space through which the endoscope 3 can be inserted. Inner-side transmitting rods 22 for performing operations to push or pull movement supporting portions 25 are connected to respective movement supporting portions 25. On the proximal end portion side, each inner-side transmitting rod 22 is inserted through the inside of a hollow inner-side guide pipe 24.

Figure 9A:
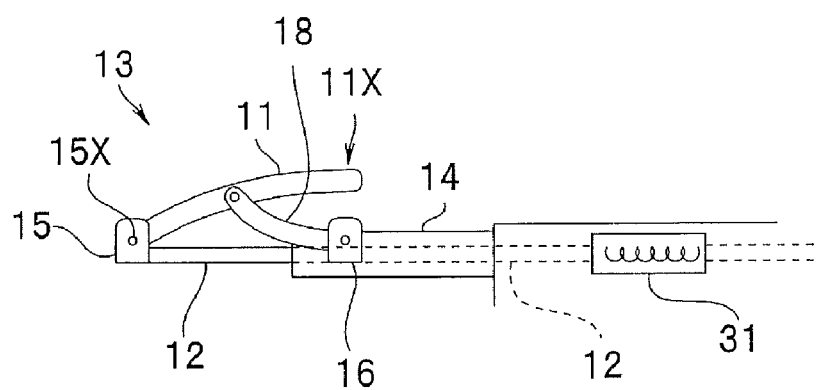
FIG. 9A is a side view for describing motion of an inner-side fixing section or an outer-side fixing section of the endoscope insertion apparatus of the first embodiment, that illustrates a case where an arm member is in a reduced diameter state.
Figure 9B:
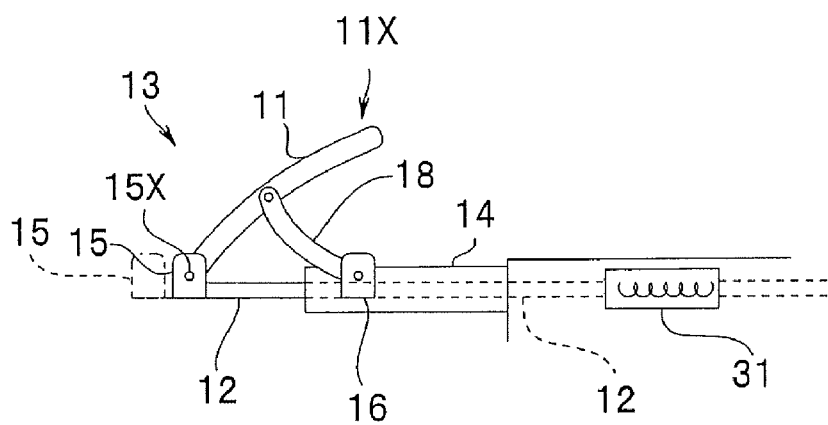
FIG. 9B is a side view for describing motion of the inner-side fixing section or the outer-side fixing section of the endoscope insertion apparatus of the first embodiment, that illustrates a case where an arm member is in an expanded diameter state.
Figure 9C:
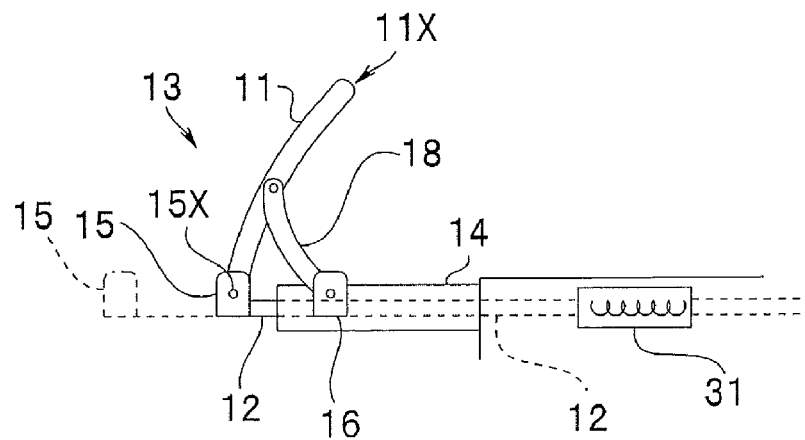
FIG. 9C is a side view for describing motion of the inner-side fixing section or the outer-side fixing section of the endoscope insertion apparatus of the first embodiment, that illustrates a case where an arm member is in a state in which the diameter thereof is expanded to the maximum.

Next, motion of the inner-side fixing sections 23 and outer-side fixing sections 13 is described taking the outer-side fixing sections 13 as an example using FIG. 9A to FIG. 9C. In this connection, only one outer-side fixing section 13 is illustrated in FIG. 9.

As shown in FIG. 9A, the outer-side fixing section 13 can cause an outer-side arm 11 to change between an expanded diameter state and a reduced diameter state by means of a link mechanism formed by the movement supporting portion 15, the fixed support portion 16, and the link portion 18. The outer-side transmitting rod 12 connected to the movement supporting portion 15 is housed inside the outer-side guide pipe 14 on the proximal end portion side.

As shown in FIG. 9B, when the outer-side transmitting rod 12 is operated so as to be pulled to the proximal end portion side, the movement supporting portion 15 of the outer-side arm 11 is drawn to the proximal end portion side and hence the outer-side arm 11 rotates in a diameter-expanding direction around the pivot 15X. Next, as shown in FIG. 9C, when the outer-side transmitting rod 12 is operated so as to be pulled further to the proximal end portion side, the outer-side arm 11 rotates further in the diameter-expanding direction around the pivot 15X to reach a state in which the diameter thereof is expanded to the maximum.

In contrast, when the outer-side transmitting rod 12 operated so as to be pushed to the distal end portion direction from the state shown in FIG. 9B or FIG. 9C, the outer-side arm 11 rotates in a diameter-reducing direction around the pivot 15X.

In FIG. 9A to FIG. 9C, an insertion apparatus 2 is exemplified that has an outer-side elastic connection portion 31 that has elasticity and that is provided partway along the outer-side transmitting rod 12. The outer-side elastic connection portion 31 is, for example, a helical spring. The insertion apparatus 2 that has the outer-side elastic connection portion 31 can prevent the outer-side arm 11 from pressing excessively against the intestinal wall 9 if the outer-side transmitting rod 12 is operated so as to be pulled to an excessive degree by the surgeon. Naturally, the insertion apparatus 2 also preferably has an inner-side elastic connection portion that has elasticity and that is provided partway along the inner-side transmitting rod 22.

The insertion apparatus 2 that includes at least either one of an inner-side elastic connection portion that has elasticity and that connects between the inner-side transmitting rod 22 that is flexible as an inner-side operation transmitting section and the inner-side operation portion 24X, and an outer-side elastic connection portion that has elasticity and that connects between the outer-side transmitting rod 12 that is flexible as an outer-side operation transmitting section and the outer-side operation portion 14X, can prevent the outer-side arm 11 from pressing excessively against the intestinal wall 9.

In this connection, preferably the inner-side distal end portions 21XA to 21XD and the outer-side distal end portions 11XA to 11XD are softer than portions other than the distal end portions that are principal portions of the outer-side arms 11A to 11D and inner-side arms 21A to 21D. More specifically, the distal end portion of the arm member may be a separate member to the arm member. For example, the arm member may be formed with a metal material and the distal end portion of the arm member may be formed with a resin material. According to the insertion apparatus 2 in which the distal end portions of the inner-side arm members and the outer-side arm members are softer than portions other than the distal end portions of the inner-side arm members and the outer-side arm members, when the distal end portion of an arm member presses the intestinal wall 9, since there is a large amount of friction between the distal end portion and the intestinal wall 9, the fixing section that is fixed to the intestinal wall 9 does not move even if an external force is applied thereto.

Next, the structure of the insertion apparatus 2 is further described using FIG. 10A to FIG. 18B. In the following drawings, to simplify the illustration, the endoscope 3 is not shown unless particularly necessary.

Figure 10A:
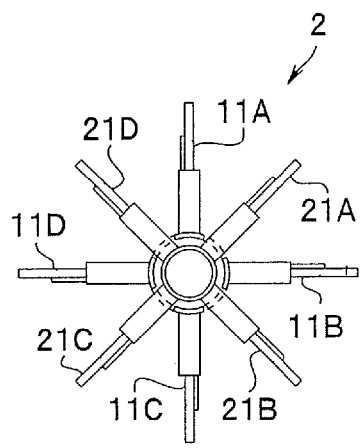
FIG. 10A is an exterior view of the endoscope insertion apparatus according to the first embodiment, that is a view as observed from the distal end side.
Figure 10B:
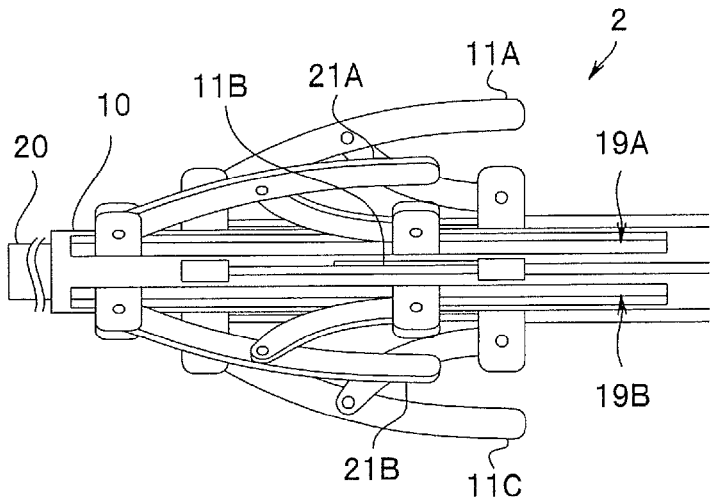
FIG. 10B is an exterior side view of the endoscope insertion apparatus according to the first embodiment.

As shown in FIG. 10A and FIG. 10B, the outer-side unit 10 is mounted to the outer circumferential portion of the inner-side unit 20 for use. More specifically, the inner-side arm 21A of the inner-side unit 20 protrudes from the slit portion 19A of the outer-side unit 10, the inner-side arm 21B protrudes from the slit portion 19B, the inner-side arm 21C protrudes from the slit portion 19C, and the inner-side arm 21D protrudes from the slit portion 19D.

Figure 11:
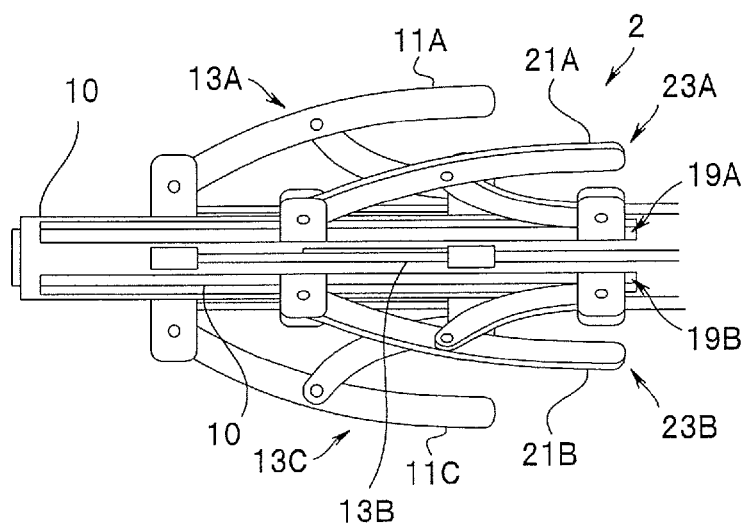
FIG. 11 is an exterior side view of the endoscope insertion apparatus according to the first embodiment.

The inner-side arms 21 can advance and retract in the frontward and rearward directions with respect to the insertion direction along the slit portions 19. As shown in FIG. 11, when the outer-side fixing section 13 has moved to the distal end portion side, the outer-side distal end portion 11X is movable forward and rearward in the insertion direction with respect to the inner-side distal end portion 21X.

Figure 13B:
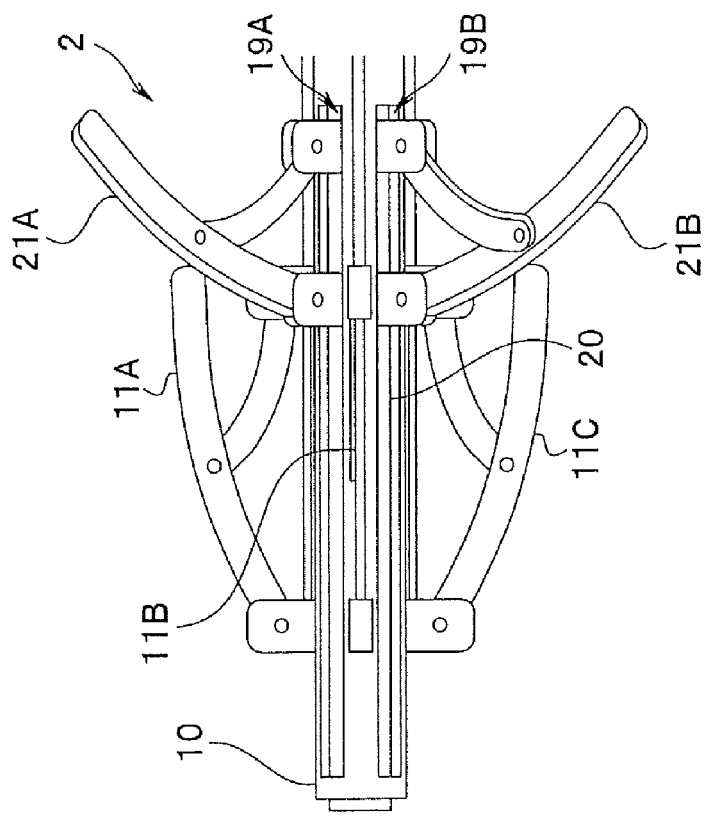
FIG. 13B is an exterior side view of the endoscope insertion apparatus according to the first embodiment.
Figure 13A:
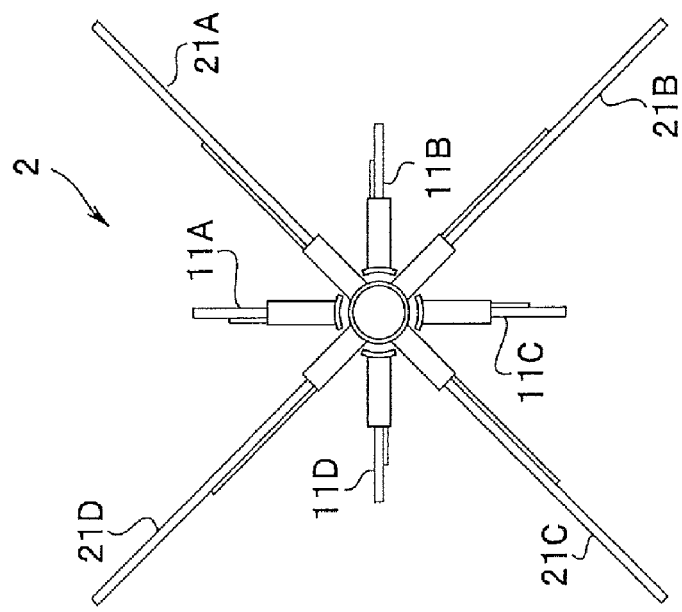
FIG. 13A is an exterior view of the endoscope insertion apparatus according to the first embodiment, that is a view as observed from the distal end side.

As shown in FIG. 12A and FIG. 12B, according to the insertion apparatus 2, the inner-side arms 21 of the inner-side unit 20 can enter a reduced diameter state when the outer-side arms 11 of the outer-side unit 10 are in an expanded diameter state. Further, as shown in FIG. 13A and FIG. 13B, the inner-side arms 21 of the inner-side unit 20 can enter an expanded diameter state when the outer-side arms 11 of the outer-side unit 10 are in a reduced diameter state. Furthermore, regardless of whether the outer-side arms 11 are in an expanded diameter state or a reduced diameter state, the inner-side arms 21 can advance and retract in the frontward and rearward directions in the insertion direction with respect to the outer-side arms 11 through the slit portions 19.

Figure 14:
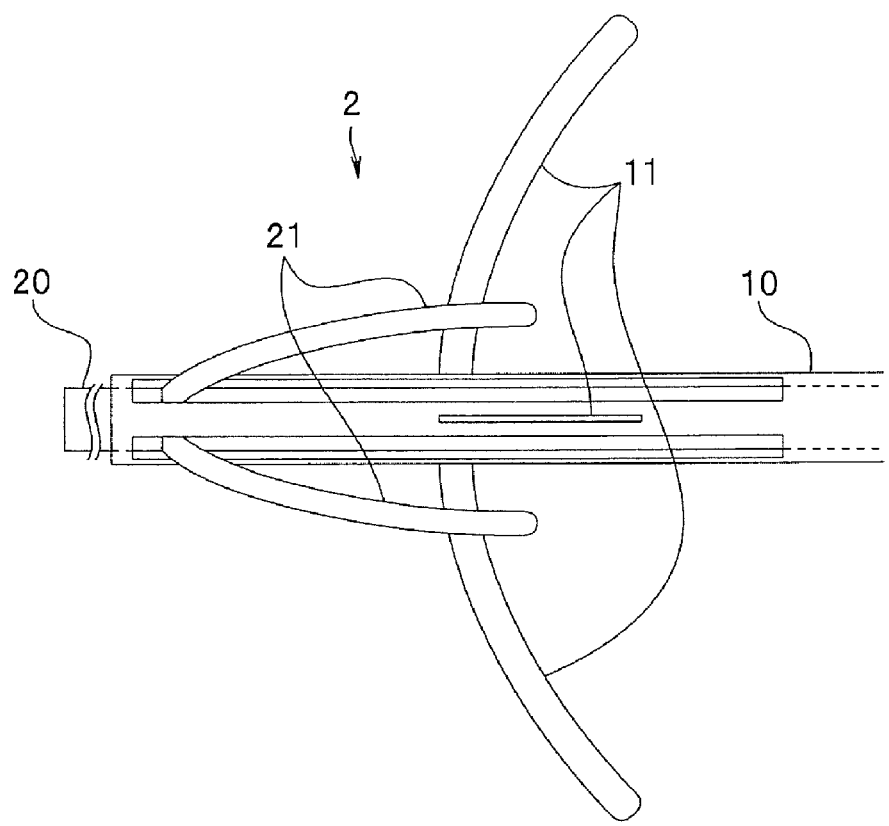
FIG. 14 is a side schematic view of the endoscope insertion apparatus according to the first embodiment.
Figure 15:
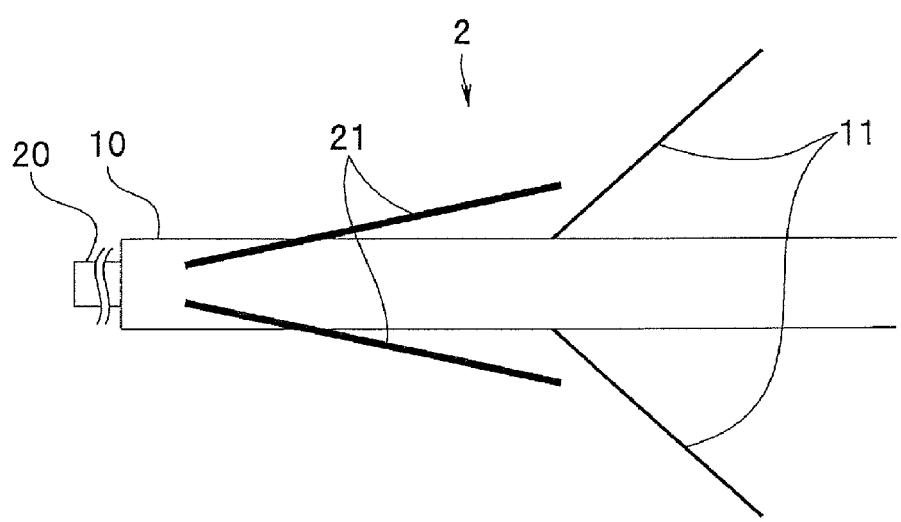
FIG. 15 is a side schematic view of the endoscope insertion apparatus according to the first embodiment.

In this connection, although the illustration of FIG. 6 has been simplified in FIG. 14, hereunder the illustration of FIG. 6 is further simplified as shown in FIG. 15. More specifically, two outer-side arms 11 are illustrated using thick lines that are twice the width of a normal line, and two inner-side arms 21 are illustrated using thick lines that are four times the width of a normal line.

Figure 16:
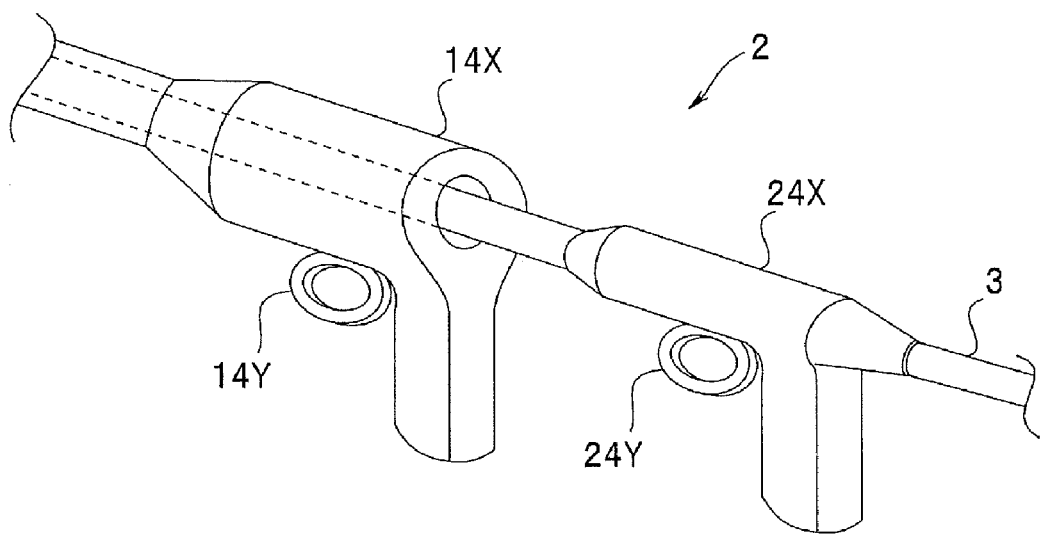
FIG. 16 is an oblique perspective view of an operation portion of the endoscope insertion apparatus according to the first embodiment.

As shown in FIG. 16, the operation portion of the insertion apparatus 2 includes an inner-side operation portion 24X that operates an inner-side insertion assisting section, and an outer-side operation portion 14X. An inner-side slide ring 24Y is provided on the inner-side operation portion 24X, and an outer-side slide ring 14Y is provided on the outer-side operation portion 14X.

Figure 17:
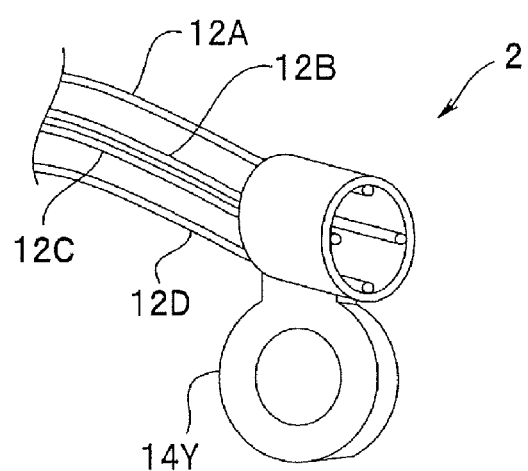
FIG. 17 is a view for describing the structure of a slide ring of the operation portion of the endoscope insertion apparatus according to the first embodiment.

As shown in FIG. 17, outer-side transmitting rods 12A to 12D for operating the outer-side arms 11A to 11D are connected to the outer-side slide ring 14Y. Also, although not shown in FIG. 17, inner-side transmitting rods 22A to 22D for operating the inner-side arms 21A to 21D are connected to the inner-side slide ring 24Y.

Figure 18A:
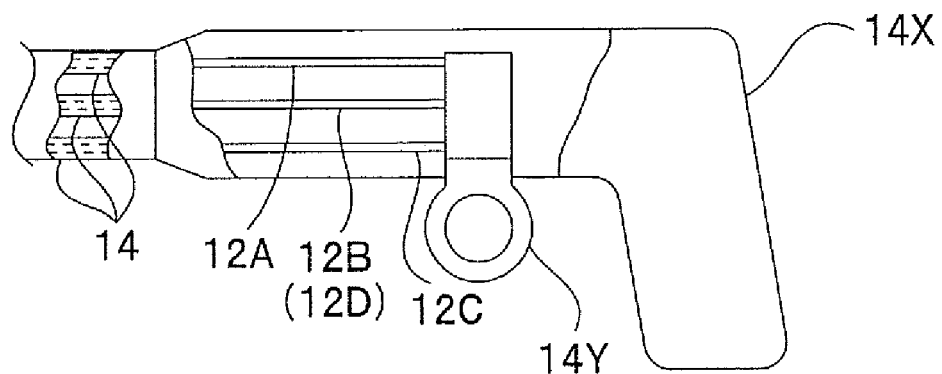
FIG. 18A is a partially transparent view for describing the operation portion of the endoscope insertion apparatus according to the first embodiment.
Figure 18B:
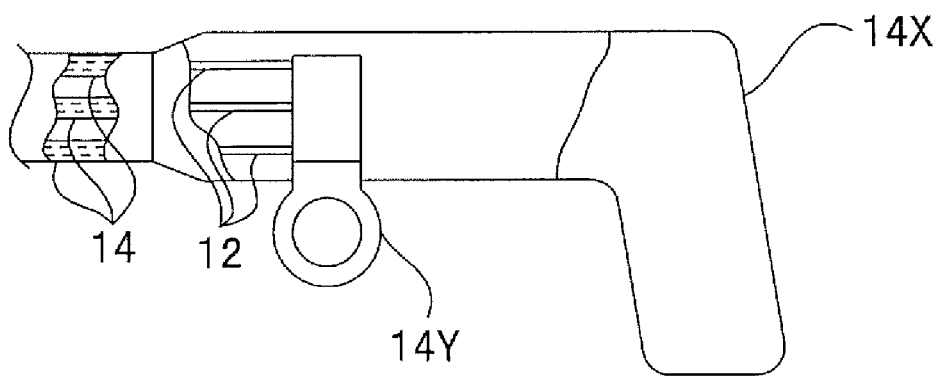
FIG. 18B is a partially transparent view for describing the operation portion of the endoscope insertion apparatus according to the first embodiment.

Therefore, for example, as shown in FIG. 18A and FIG. 18B, the surgeon causes the outer-side arms 11A to 11D to change between an expanded diameter state and a reduced diameter state by performing an operation to push/pull the outer-side slide ring 14Y of the outer-side operation portion 14X forward/rearward with respect to the insertion direction. The structure of the inner-side operation portion 24X and the like is the same as the structure of the outer-side operation portion 14X and the like.

The installation space can be decreased by reducing the four outer-side transmitting rods 12A to 12D or four inner-side transmitting rods 22A to 22D that are unshown to a single rod each between the distal end side and the insertion operation portion 30.

The surgeon can also move the entire inner-side unit 20 and outer-side unit 10 to the proximal end portion side by performing an operation to pull the entire operation portion, that is, the outer-side operation portion 14X and the inner-side operation portion 24X, to the proximal end portion side. As described later, a pulling operation with respect to the entire operation portion is used when the surgeon performs an operation that shortens the intestinal tract 9A, that is, when the surgeon performs a drawing-in operation.

Figure 19A:
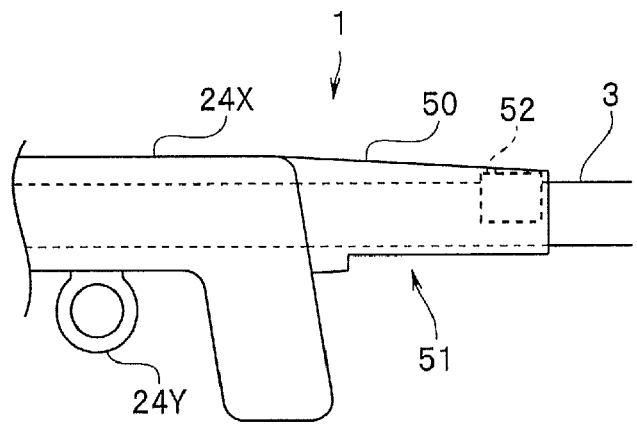
FIG. 19A is a side view for describing a fixing section of the endoscope insertion apparatus according to the first embodiment.
Figure 19B:
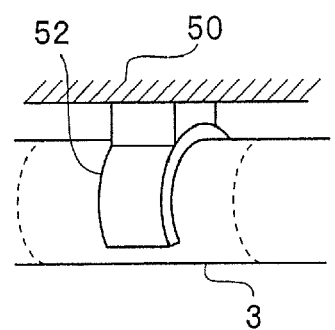
FIG. 19B is a partially transparent view for describing the fixing section of the endoscope insertion apparatus according to the first embodiment.

As shown in FIG. 6, the endoscope 3 is fixed to the inner-side unit 20. As shown in FIG. 19A to FIG. 19B, the fixing location is, for example, an extending portion 50 that is provided on a proximal end portion side of the inner-side operation portion 24X. The extending portion 50 has a fixing member 52, and a notch 51 is provided at a lower part thereof. As shown in FIG. 19B, the fixing member 52 is an elastic member whose cross section is a "C" shape. The fixing member 52 is fitted to the endoscope 3 and detachably fixes the endoscope 3.

Figure 20A:
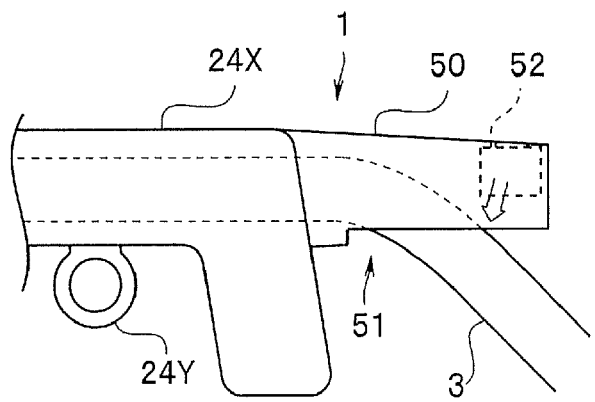
FIG. 20A is a side view for describing a fixing section of the endoscope insertion apparatus according to the first embodiment.
Figure 20B:
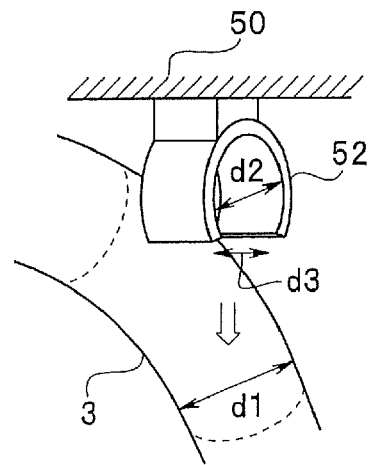
FIG. 20B is a partially transparent view for describing the fixing section of the endoscope insertion apparatus according to the first embodiment.

More specifically, an inner diameter d2 of the "C"-shaped fixing member 52 is approximately the same as an outer diameter d1 of the endoscope 3, and a width d3 of an opening portion is normally slightly smaller than d1. However, the width of the opening portion changes elastically under an external stress and becomes greater than d1. Therefore, as shown in FIG. 20A and FIG. 20B, the surgeon can detach the endoscope 3 from the fixing member 52 by pushing the endoscope 3 that is fitted in the fixing member 52 downward along the notch 51 of the extending portion 50. Conversely, the surgeon can fit and fix the endoscope 3 in the fixing member 52 by pushing the endoscope 3 against the opening portion of the fixing member 52. That is, the endoscope 3 is detachably fixed to the insertion apparatus 2 through the fixing member 52.

Although FIG. 6 shows a state in which the bent endoscope 3 is protruding from the distal end portion of the insertion apparatus 2, during an insertion operation the distal end portion of the endoscope 3 may be fixed at a position that is contained inside the insertion apparatus 2. After inserting the endoscope 3 as far as a desired position, the surgeon can release the fixed state of the endoscope 3 and cause the endoscope 3 to protrude from the distal end portion of the insertion apparatus 2 for use. Naturally, the surgeon may fix the endoscope 3 again during use in order to stabilize the observation field of view.

As described above, the insertion apparatus 2 that includes the fixing member 52 that detachably fixes the endoscope 3 has excellent operability and a simple structure. In this connection, the fixing member 52 may be arranged at a position on the inner-side unit 20, or when it is not necessary to release the fixed state of the endoscope 3 during an insertion operation, the fixing member 52 may be arranged at a position on the distal end portion side of the extending portion 50 or the like, rather than on the proximal end portion side.

Figure 21A:
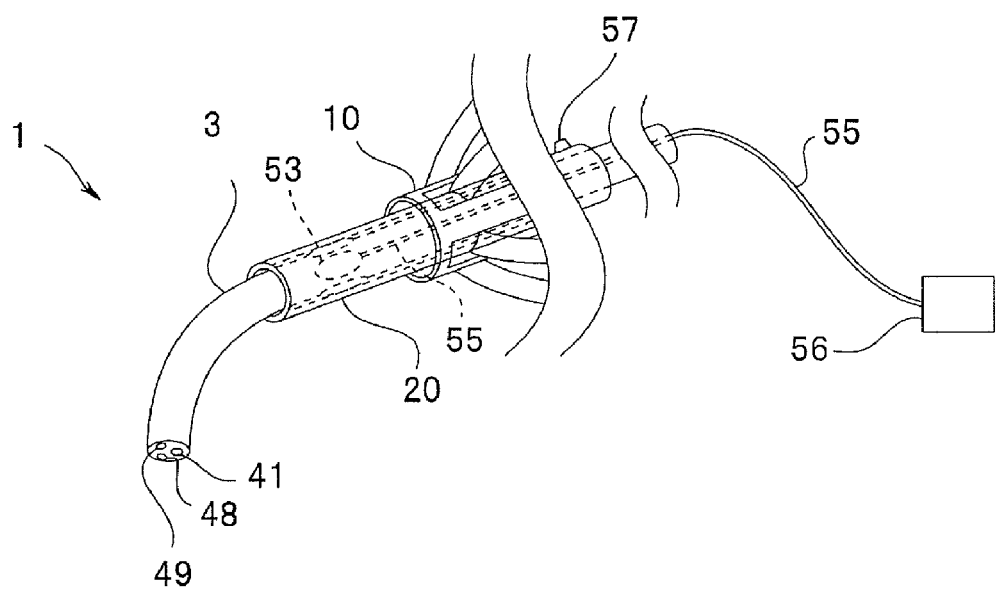
FIG. 21A is an oblique perspective view for describing the fixing section of the endoscope insertion apparatus according to the first embodiment.

A method of detachably fixing the endoscope 3 to the insertion apparatus 2 is not limited to use of the fixing member 52 as shown in FIG. 19A and the like. For example, a balloon-type fixing section may be used. As exemplified in FIG. 21A to FIG. 21C, a balloon-type fixing section includes three balloons 53 that are provided between the endoscope 3 and the inner-side unit 20. The balloons 53 inflate when a fluid is supplied from a fluid supply system 56 via a fluid supply tube 55, and deflate when the fluid inside each balloon decreases. That is, the surgeon can inflate/deflate the balloons 53 by operating a fluid supply switch 57. In this connection, the fluid supply tube 55 is thin and flexible and therefore does not cause an increase in the diameter of the insertion apparatus 2.

Figure 21B:
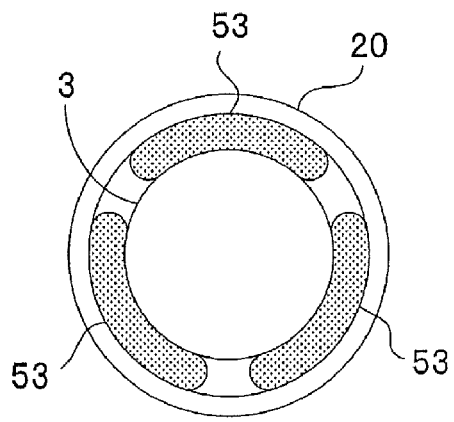
FIG. 21B is a view for describing the cross-sectional structure of the fixing section of the endoscope insertion apparatus according to the first embodiment.
Figure 21C:
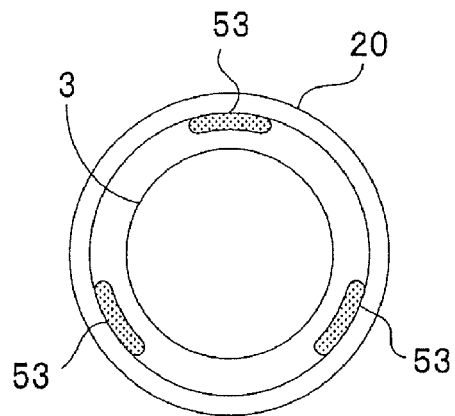
FIG. 21C is a view for describing the cross-sectional structure of the fixing section of the endoscope insertion apparatus according to the first embodiment.

As shown in FIG. 21B, when the balloons 53 inflate, the endoscope 3 is pressed by the balloons 53 so as to fix the endoscope 3 inside the inner-side unit 20. In contrast, as shown in FIG. 21C, when the balloons 53 deflate, the endoscope 3 can move inside the inner-side unit 20.

Figure 22A:
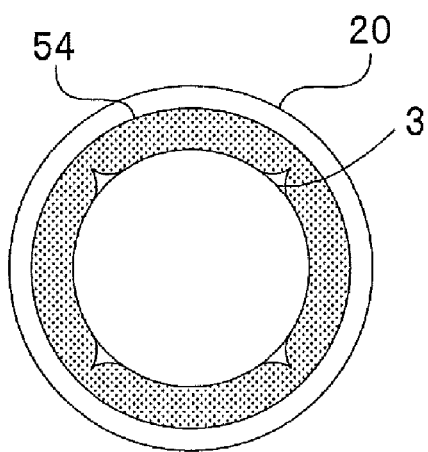
FIG. 22A is a view for describing the cross-sectional structure of the fixing section of the endoscope insertion apparatus according to the first embodiment.
Figure 22B:
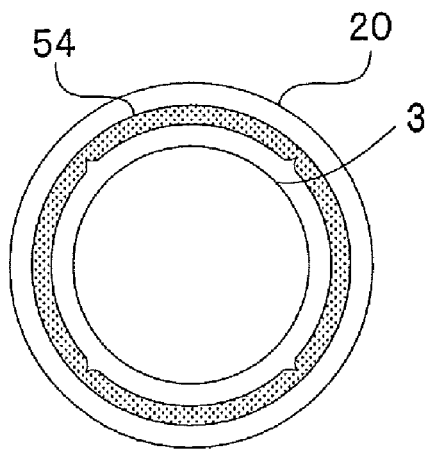
FIG. 22B is a view for describing the cross-sectional structure of the fixing section of the endoscope insertion apparatus according to the first embodiment.

In this connection, a single balloon 54 that has a donut shape as shown in FIG. 22A and FIG. 22B may also be used as the fixing balloon.

Since the balloons 53 or 54 can fix the endoscope 3 at a center part inside the inner-side unit 20, that is, dispose the image pickup section at the center of a tube cavity, it is easy for the surgeon to secure a desired observation field of view with the image pickup section 41. Conversely, when it is not necessary to fix the endoscope 3 at a center part inside the inner-side unit 20, a single balloon may be used and the endoscope 3 may be pressed and fixed to the inner wall of the inner-side unit 20 by the balloon.

The balloon-type fixing section has the advantages of a fixing section that uses the fixing member 52, and because the endoscope 3 can be fixed at the distal end portion side, the balloon-type fixing section can also stabilize the observation field of view.

The endoscope insertion apparatus that can detachably fix the endoscope 3 as described above has excellent operability.

Next, a method of inserting the endoscope insertion apparatus according to the first embodiment is described using FIG. 23A to FIG. 27G.

Figure 23A:
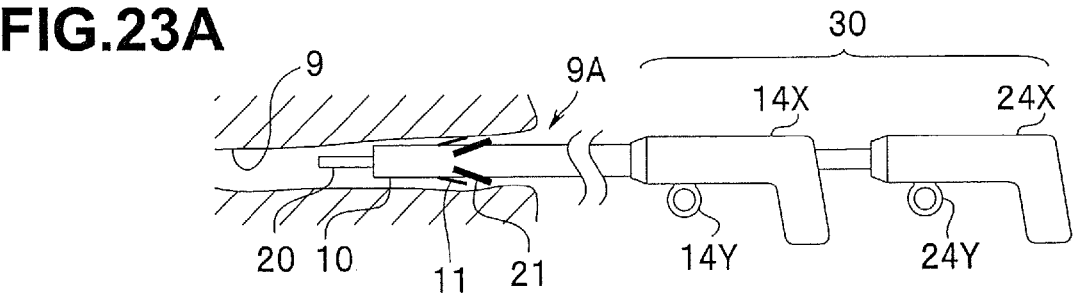
FIG. 23A is a cross-sectional schematic view for describing a method of inserting the endoscope insertion apparatus according to the first embodiment.
Figure 25A:
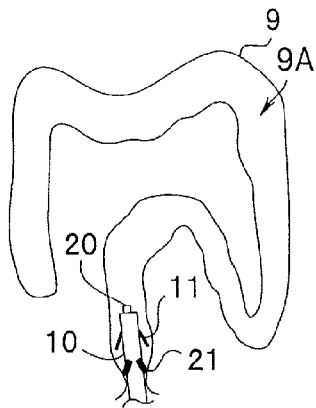
FIG. 25A is a cross-sectional schematic view for describing a method of inserting the endoscope insertion apparatus according to the first embodiment.

<Initial Insertion Step> FIG. 23A and FIG. 25A

The distal end portion side of the insertion apparatus 2 in which the inner-side arms 21 of the inner-side unit 20 and the outer-side arms 11 of the outer-side unit 10 are each in a reduced diameter state is inserted into the intestinal tract 9A from the anus of the subject. The endoscope 3 is inserted into and fixed to an inner circumferential portion of the inner-side unit 20.

At this time, as shown in FIG. 23A, there is a predetermined distance between the outer-side operation portion 14X and the inner-side operation portion 24X, and the inner-side unit 20 is at the most rearward position in the insertion direction with respect to the relative relationship between the inner-side unit 20 and the outer-side unit 10. More specifically, the inner-side arms 21 are positioned on the proximal end portion side of the slit portions 19.

Figure 23B:
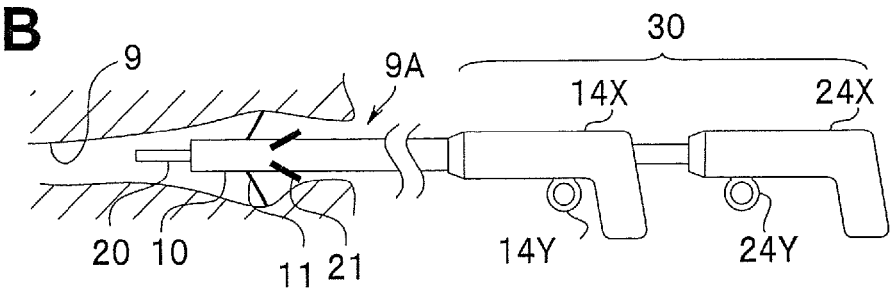
FIG. 23B is a cross-sectional schematic view for describing a method of inserting the endoscope insertion apparatus according to the first embodiment.
Figure 25B:
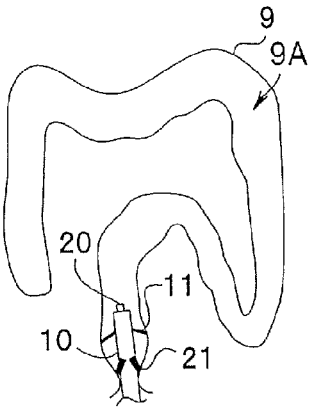
FIG. 25B is a cross-sectional schematic view for describing a method of inserting the endoscope insertion apparatus according to the first embodiment.

<Outer-side Insertion Assisting Section Fixing Step> FIG. 23B and FIG. 25B

The surgeon causes the outer-side arms 11 of the outer-side unit 10 to enter an expanded diameter state so as to press against and be fixed to the intestinal wall 9. More specifically, the surgeon performs a pulling operation with respect to the outer-side slide ring 14Y of the outer-side operation portion 14X. Because the insertion apparatus 2 has an outer-side elastic connection portion 31 that has elasticity that is provided partway along the outer-side transmitting rod 12, even if the surgeon performs a strong pulling operation with respect to the outer-side slide ring 14Y, the outer-side arms 11 do not press with unnecessary strength against the intestinal wall 9.

In this connection, the term "expanded diameter state" does not refer to a state in which the diameter is expanded to a maximum. Rather, the term "expanded diameter state" refers to a state which is sufficient to fix the outer-side arms 11 to the intestinal wall 9. There are individual differences and age differences with respect to the inner diameter of the intestinal tract 9A. For example, if the outer-side arms 11 are in a state in which the outer-side arms 11 are sufficiently fixed to the intestinal wall 9 in the state illustrated in FIG. 9B, the state illustrated in FIG. 9B is the expanded diameter state. Further, there are cases that correspond to the expanded diameter state of the present invention even when the diameter of the arm members is expanded by only a slight amount.

Figure 23C:
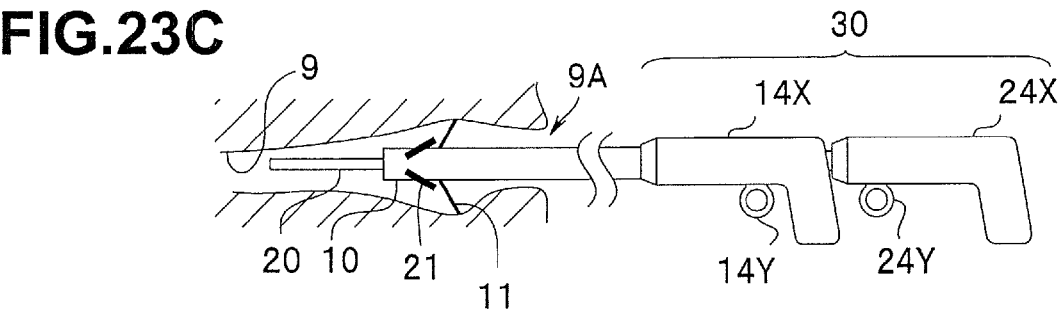
FIG. 23C is a cross-sectional schematic view for describing a method of inserting the endoscope insertion apparatus according to the first embodiment.
Figure 25C:
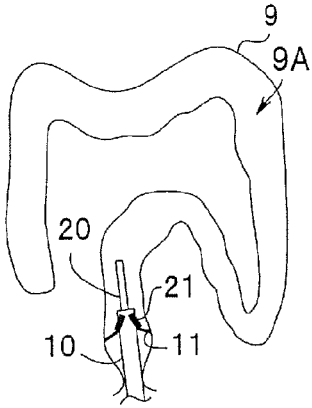
FIG. 25C is a cross-sectional schematic view for describing a method of inserting the endoscope insertion apparatus according to the first embodiment.

<Inner-side Insertion Assisting Section Advancing Step> FIG. 23C and FIG. 25C

The surgeon advances the inner-side unit 20 as far as a deep region side of the intestinal tract 9A until the inner-side arms 21 move to the front in the insertion direction with respect to the outer-side arms 11 that are alternately arranged in the circumferential direction with the inner-side arm members in the circumferential direction of the axis of advancement and retraction.

More specifically, as shown in FIG. 23C, the surgeon pushes in the inner-side operation portion 24X until the inner-side operation portion 24X is adjacent to the outer-side operation portion 14X. As a result, the inner-side unit 20 moves to the most forward position in the insertion direction with respect to the relative relationship between the inner-side unit 20 and the outer-side insertion assisting section. More specifically, the inner-side arms 21 are positioned at the distal end portion side of the slit portions 19.

In this connection, when the inner-side arms 21 move forward of the outer-side arms 11 in the insertion direction, in other words, when the inner-side arms 21 move to the deep region side, it is sufficient that at least the inner-side distal end portions 21X move to the same position as the outer-side distal end portions 11X in the insertion direction, in other words, move as far as the same insertion depth. In this case, even if the intestinal tract 9A has been contracted during the movement up to this point, the contracted state is released when the inner-side distal end portions 21X move as far as the same insertion depth as the outer-side distal end portions 11X. Consequently, the distal end portion of the insertion apparatus 2 can actually move in the direction of the deep region of the intestinal tract 9A.

Figure 23D:
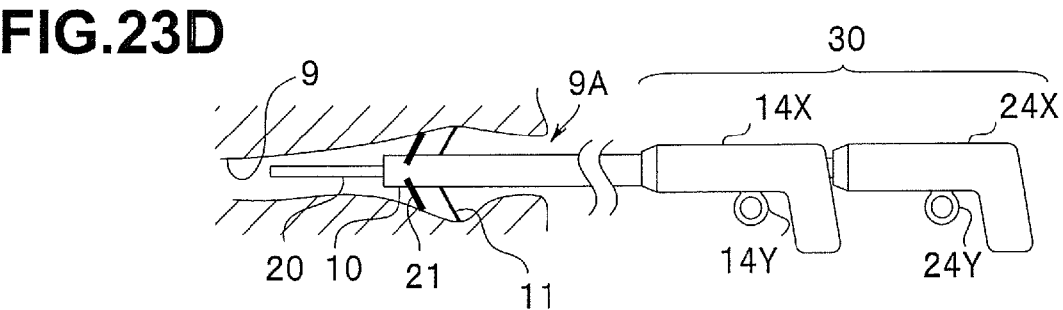
FIG. 23D is a cross-sectional schematic view for describing a method of inserting the endoscope insertion apparatus according to the first embodiment.
Figure 25D:
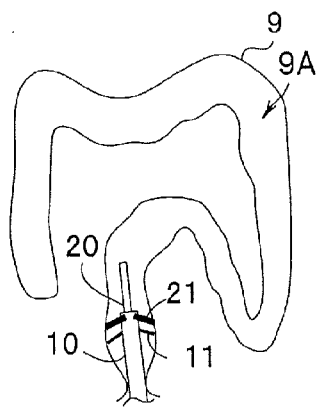
FIG. 25D is a cross-sectional schematic view for describing a method of inserting the endoscope insertion apparatus according to the first embodiment.

<Inner-side Insertion Assisting Section Fixing Step> FIG. 23D and FIG. 25D

The surgeon causes the inner-side arms 21 of the inner-side unit 20 to enter an expanded diameter state and push against the intestinal wall 9 to be fixed thereto. More specifically, the surgeon performs an operation to pull the inner-side slide ring 24Y of the inner-side operation portion 24X. Because the insertion apparatus 2 has an outer-side elastic connection portion that has elasticity and that is provided partway along the inner-side transmitting rod 22, even if the surgeon performs a strong pulling operation with respect to the outer-side slide ring 14Y, the inner-side arms 21 do not press with unnecessary strength against the intestinal wall 9.

Figure 23E:
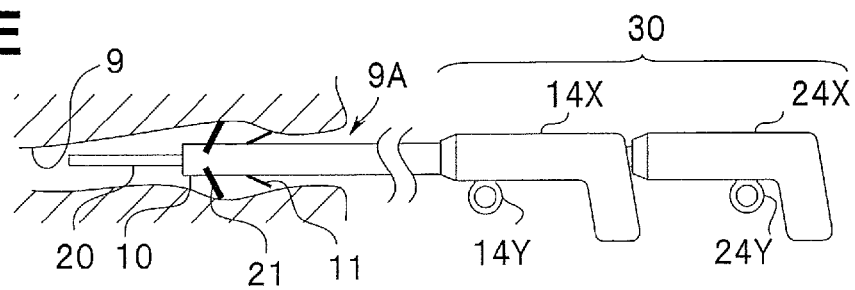
FIG. 23E is a cross-sectional schematic view for describing a method of inserting the endoscope insertion apparatus according to the first embodiment.
Figure 25E:
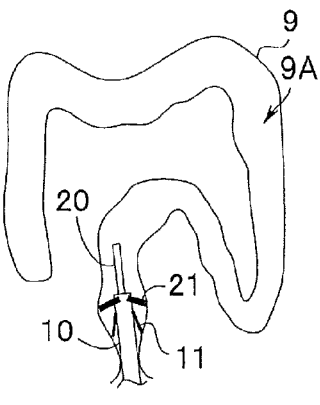
FIG. 25E is a cross-sectional schematic view for describing a method of inserting the endoscope insertion apparatus according to the first embodiment.

<Outer-side Insertion Assisting Section Pressing Release Step> FIG. 23E and FIG. 25E The surgeon causes the outer-side arms 11 of the outer-side unit 10 to enter a reduced diameter state and thereby release the state in which the outer-side arms 11 press against the intestinal wall 9. More specifically, the surgeon performs an operation to push the outer-side slide ring 14Y of the outer-side operation portion 14X.

Figure 24A:
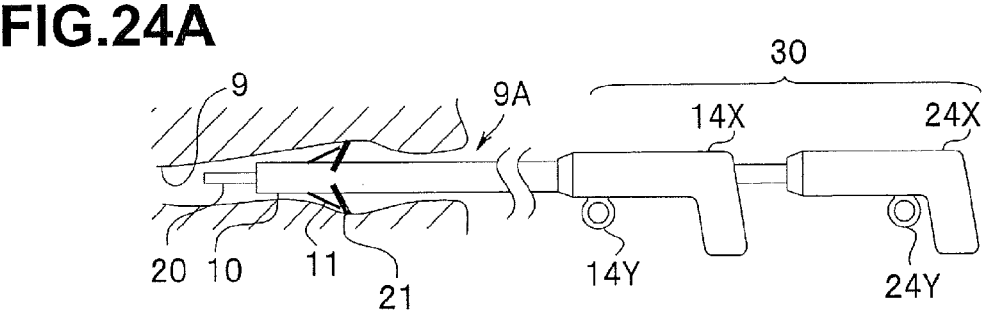
FIG. 24A is a cross-sectional schematic view for describing a method of inserting the endoscope insertion apparatus according to the first embodiment.
Figure 25F:
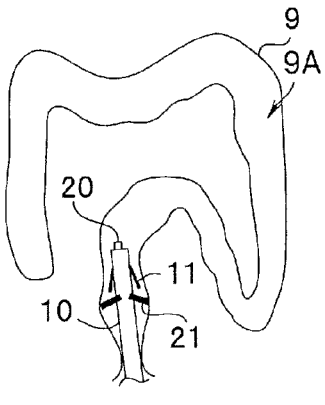
FIG. 25F is a cross-sectional schematic view for describing a method of inserting the endoscope insertion apparatus according to the first embodiment.

<Outer-side Insertion Assisting Section Advancing Step> FIG. 24A and FIG. 25F

The surgeon advances the outer-side unit 10 as far as the deep region side of the intestinal tract 9A until the outer-side arms 11 move to the front in the insertion direction with respect to the inner-side arms 21 that are alternately arranged in the circumferential direction with the outer-side arm members in the circumferential direction of the axis of advancement and retraction.

Figure 24B:
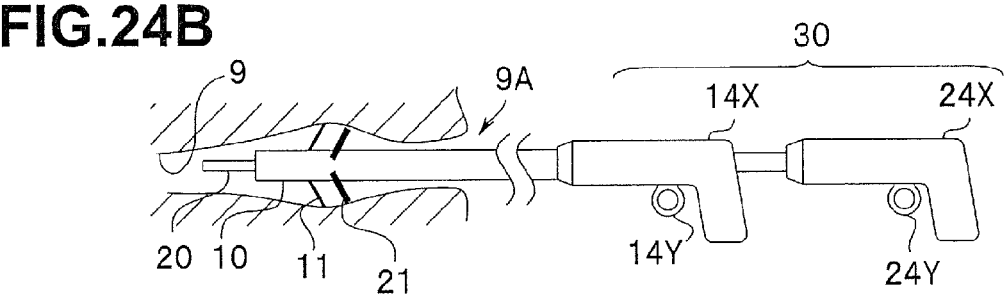
FIG. 24B is a cross-sectional schematic view for describing a method of inserting the endoscope insertion apparatus according to the first embodiment.
Figure 25G:
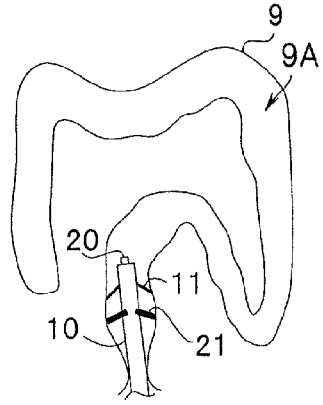
FIG. 25G is a cross-sectional schematic view for describing a method of inserting the endoscope insertion apparatus according to the first embodiment.

<Outer-side Insertion Assisting Section Fixing Step> FIG. 24B and FIG. 25G

The surgeon again causes the outer-side arms 11 of the outer-side unit 10 to enter an expanded diameter state so that the outer-side arms 11 press against the intestinal wall 9 and are fixed thereto.

Figure 24C:
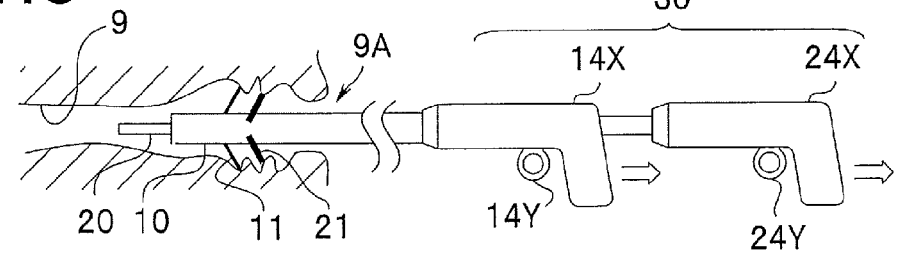
FIG. 24C is a cross-sectional schematic view for describing a method of inserting the endoscope insertion apparatus according to the first embodiment.
Figure 25H:
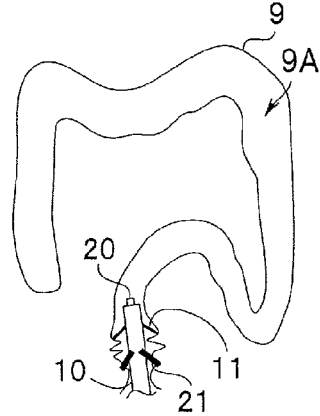
FIG. 25H is a cross-sectional schematic view for describing a method of inserting the endoscope insertion apparatus according to the first embodiment.

<Intestinal Tract Shortening Step> FIG. 24C and FIG. 25H

The surgeon performs an operation to pull the operation portions 14A and 24X to the proximal end portion side. More specifically, the surgeon shortens the intestinal tract 9A that is not fixed inside the body cavity by drawing in the intestinal tract 9A towards the surgeon.

Figure 24D:
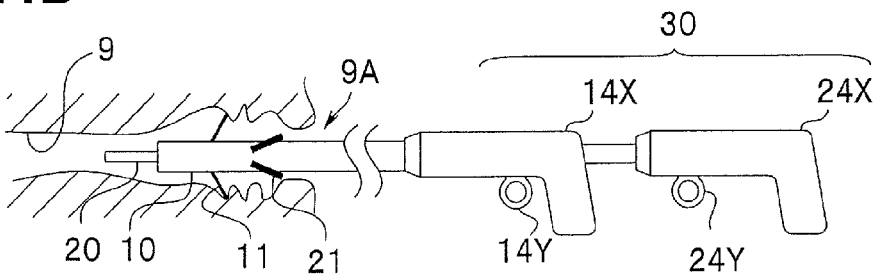
FIG. 24D is a cross-sectional schematic view for describing a method of inserting the endoscope insertion apparatus according to the first embodiment.
Figure 25I:
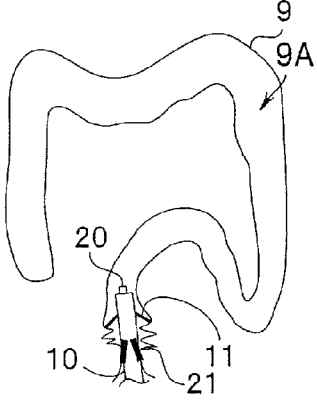
FIG. 25I is a cross-sectional schematic view for describing a method of inserting the endoscope insertion apparatus according to the first embodiment.
Figure 26A:
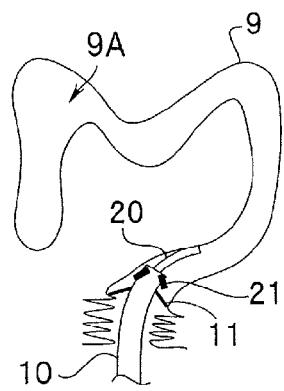
FIG. 26A is a cross-sectional schematic view for describing a method of inserting the endoscope insertion apparatus according to the first embodiment.
Figure 26B:
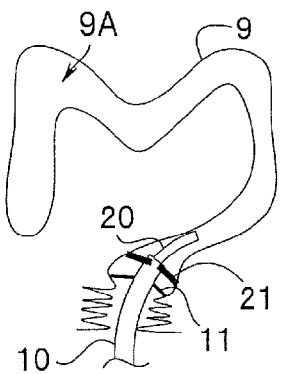
FIG. 26B is a cross-sectional schematic view for describing a method of inserting the endoscope insertion apparatus according to the first embodiment.
Figure 26C:
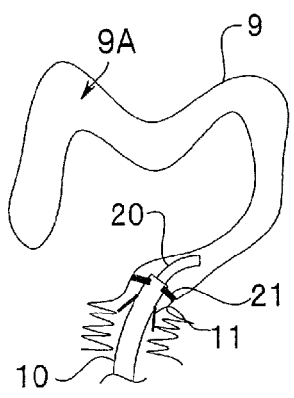
FIG. 26C is a cross-sectional schematic view for describing a method of inserting the endoscope insertion apparatus according to the first embodiment.
Figure 26D:
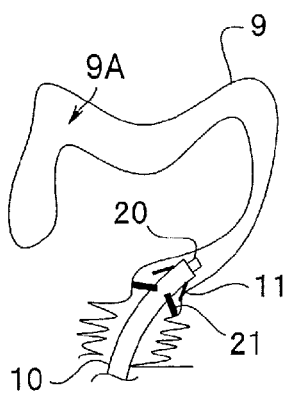
FIG. 26D is a cross-sectional schematic view for describing a method of inserting the endoscope insertion apparatus according to the first embodiment.
Figure 26E:
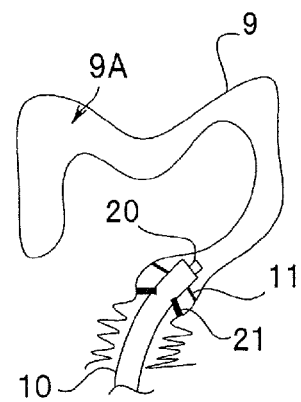
FIG. 26E is a cross-sectional schematic view for describing a method of inserting the endoscope insertion apparatus according to the first embodiment.
Figure 26F:
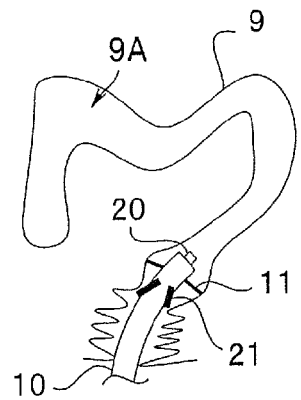
FIG. 26F is a cross-sectional schematic view for describing a method of inserting the endoscope insertion apparatus according to the first embodiment.
Figure 26G:
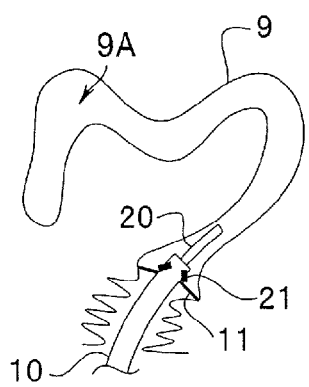
FIG. 26G is a cross-sectional schematic view for describing a method of inserting the endoscope insertion apparatus according to the first embodiment.

<Inner-side Insertion Assisting Section Pressing Release Step> FIG. 24D and FIG. 25I The surgeon causes the inner-side arms 21 of the inner-side unit 20 to enter a reduced diameter state and thereby release the state in which the inner-side arms 21 press against the intestinal wall 9.

By repeating the above procedures the surgeon can easily insert the distal end portion of the insertion apparatus 2, more specifically, the distal end portion of the endoscope 3, as far as a deep region of the intestinal tract 9A.

Next, procedures to insert the insertion apparatus 2 into a deeper region of the intestinal tract 9A are described using FIG. 26A to FIG. 27G.

Figure 27A:
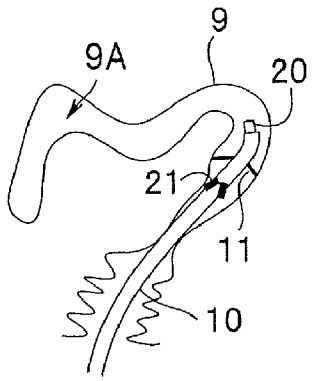
FIG. 27A is a cross-sectional schematic view for describing a method of inserting the endoscope insertion apparatus according to the first embodiment.
Figure 27B:
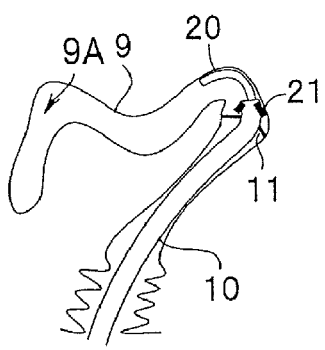
FIG. 27B is a cross-sectional schematic view for describing a method of inserting the endoscope insertion apparatus according to the first embodiment.
Figure 27C:
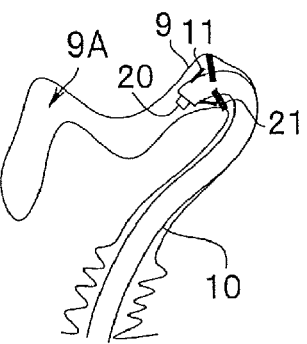
FIG. 27C is a cross-sectional schematic view for describing a method of inserting the endoscope insertion apparatus according to the first embodiment.
Figure 27D:
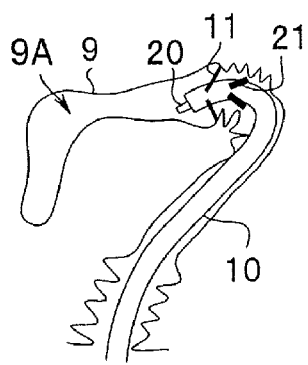
FIG. 27D is a cross-sectional schematic view for describing a method of inserting the endoscope insertion apparatus according to the first embodiment.

The procedures from FIG. 26A to FIG. 27A are approximately the same as the procedures described above. As shown in FIG. 27A, when the distal end portion of the insertion apparatus 2 passes the descending colon and reaches a splenic flexure portion, as shown in FIG. 27B, the surgeon advances the inner-side unit 20 in the insertion direction until the inner-side unit 20 passes beyond the splenic flexure portion. Subsequently, as shown in FIG. 27C, the surgeon also causes the outer-side unit 10 to pass beyond the splenic flexure portion by utilizing the inner-side unit 20 as a guide. As shown in FIG. 27D, at the transverse colon, similarly to the sigmoid colon, the surgeon can shorten the intestinal tract 9A by performing a drawing-in operation.

Figure 27E:
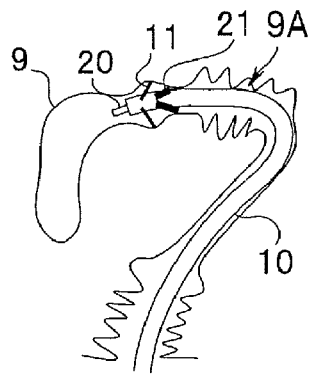
FIG. 27E is a cross-sectional schematic view for describing a method of inserting the endoscope insertion apparatus according to the first embodiment.
Figure 27F:
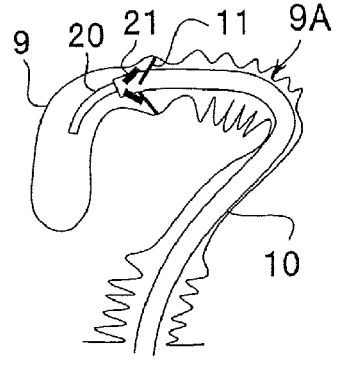
FIG. 27F is a cross-sectional schematic view for describing a method of inserting the endoscope insertion apparatus according to the first embodiment.
Figure 27G:
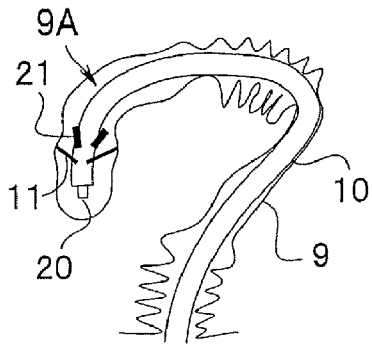
FIG. 27G is a cross-sectional schematic view for describing a method of inserting the endoscope insertion apparatus according to the first embodiment.

When the distal end portion of the insertion apparatus 2 has finished drawing in the transverse colon and reaches a hepatic flexure portion as shown in FIG. 27E, the surgeon advances the inner-side unit 20 in the insertion direction until the inner-side unit 20 passes beyond the hepatic flexure portion as shown in FIG. 27F. Subsequently, as shown in FIG. 27G, the surgeon also causes the inner-side unit 20 to pass beyond the hepatic flexure portion by utilizing the outer-side unit 10 as a guide.

Further, by performing procedures that are similar to the procedures described already, the surgeon can easily insert the distal end portion of the insertion apparatus 2, more specifically, the distal end portion of the endoscope 3, as far as a cecum portion that is a deep region of the intestinal tract 9A, and furthermore as far as the small intestine.

As described above, according to the method of inserting the insertion apparatus 2, at all times, either the outer-side arms 11 or the inner-side arms 21 are in an expanded diameter state and constantly press the intestinal wall 9. More specifically, at least one of the outer-side operation portion 14X and the inner-side operation portion 24X is always fixed to the intestinal wall 9. Consequently, when the insertion apparatus 2 is inserted, the insertion apparatus 2 can easily advance to a deep region of the intestinal tract 9A while the shortened intestinal tract 9A is retained in a shortened state.

The inner-side unit 20 and outer-side unit 10 of the insertion apparatus 2 have a link mechanism, and there is a risk that a foreign body may be sandwiched between the outer-side arms 11 and inner-side arms 21 or the like when a movement is performed to change the relative positional relationship between the inner-side unit 20 and outer-side unit 10.

Figure 28:
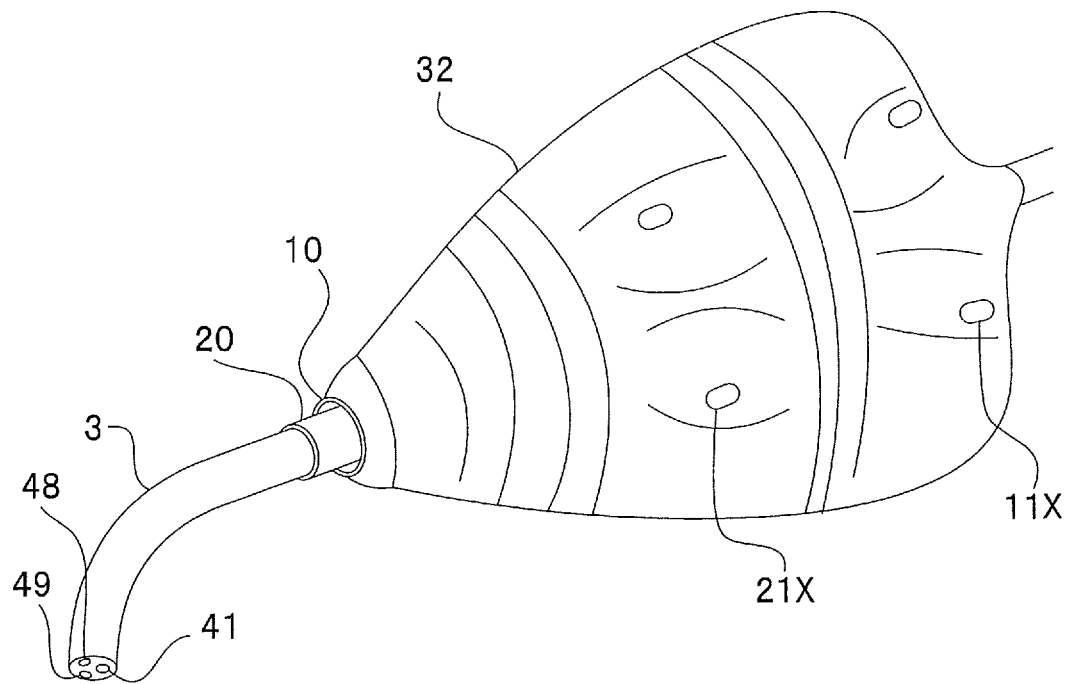
FIG. 28 is an oblique perspective view for describing a cover section of the endoscope insertion apparatus according to the first embodiment.
Figure 29:
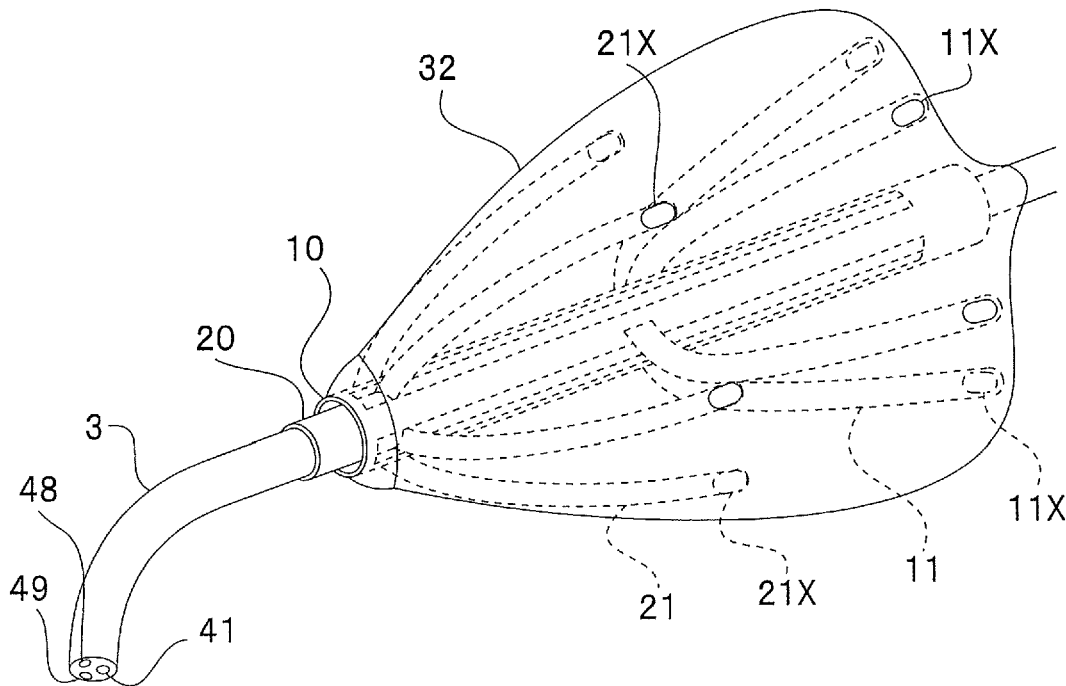
FIG. 29 is a transparent perspective view for describing the cover section of the endoscope insertion apparatus according to the first embodiment.

Consequently, as shown in FIG. 28 and FIG. 29, preferably the insertion apparatus 2 includes a cover section 32 formed by a flexible resin film that covers the outer surface of the inner-side unit 20 and the outer-side unit 10.

By forming the cover section 32 using, for example, a silicon rubber film that has excellent stretching properties, it is possible to prevent obstruction of advancing and retracting motions of the inner-side unit 20 and the outer-side unit 10, entry of a foreign body to inside the inner-side unit 20 and outer-side unit 10, and diameter-expanding and diameter-reducing motions of the inner-side unit 20 and the outer-side unit 10.

As shown in FIG. 28 and FIG. 29, in order to securely fix the insertion apparatus 2 to the intestinal wall 9, preferably the outer-side distal end portions 11X and the inner-side distal end portions 21X are exposed out of the surface of the cover section 32.

Modification Example 1 and Modification Example 2 of First Embodiment

Hereunder, insertion apparatuses 2A and 2B of modification examples of the first embodiment of the present invention are described referring to the drawings.

The insertion apparatuses 2A and 2B according to the present modification examples are similar to the insertion apparatus 2 of the first embodiment. Hence, the same components are designated by the same symbols, and a description of such components is omitted hereunder.

Figure 30:
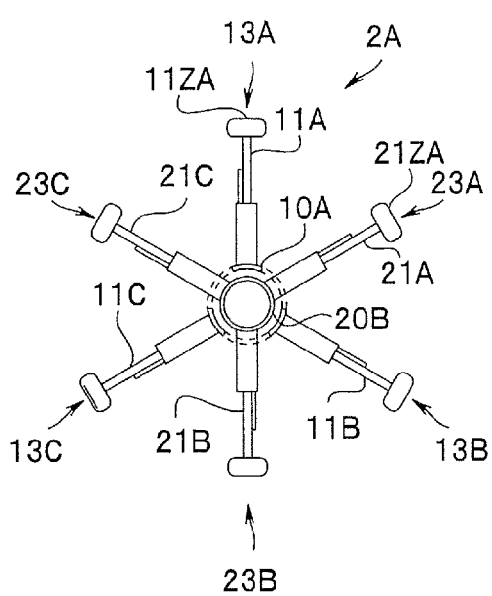
FIG. 30 is a view of an endoscope insertion apparatus according to modification example 1 of the first embodiment as observed from the distal end side thereof.

As shown in FIG. 30, an inner-side unit 20A of the insertion apparatus 2A of modification example 1 has three inner-side fixing sections 23A to 23C, and an outer-side unit 10A of the insertion apparatus 2A has three outer-side fixing sections 13A to 13C.

Figure 31:
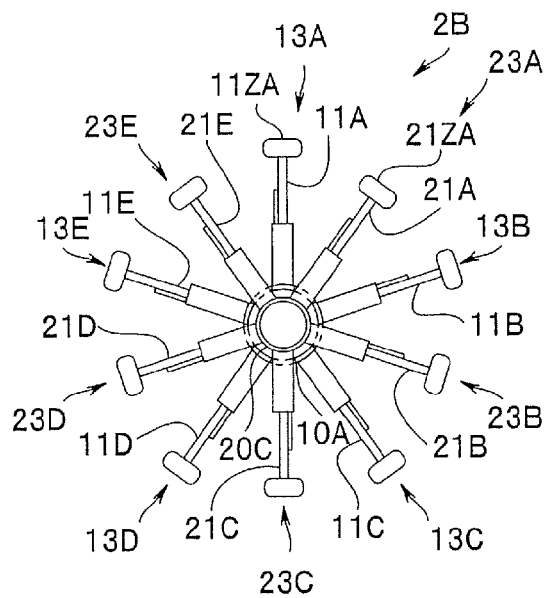
FIG. 31 is a view of an endoscope insertion apparatus according to modification example 2 of the first embodiment as observed from the distal end side thereof.

As shown in FIG. 31, an inner-side unit 20B of the insertion apparatus 2B of modification example 2 has five inner-side fixing sections 23A to 23E, and an outer-side unit 10B of the insertion apparatus 2B has five outer-side fixing sections 13A to 13E.

The insertion apparatus 2A of modification example 1 and the insertion apparatus 2B of modification example 2 have similar advantages to the insertion apparatus 2 of the first embodiment. More specifically, as long as an endoscope insertion apparatus of the present invention has two or more inner-side fixing sections 23 and two or more outer-side fixing sections 13, advantages can be obtained. In this connection, since the inner-side fixing sections 23 and the outer-side fixing sections 13 are alternately arranged in the circumferential direction on an outer circumferential portion of the insertion apparatus 2, the same number of inner-side fixing sections 23 and outer-side fixing sections 13 are provided.

Further, in FIG. 30 and FIG. 31, examples are illustrated in which the insertion apparatuses 2A and 2B include inner-side distal end members 21Z that are separate members to the inner-side arms 21 at the inner-side distal end portions 21X, and are provided with outer-side distal end members 11Z that are separate members to the outer-side arms 11 at the outer-side distal end portions 11X. The inner-side distal end members 21Z and the outer-side distal end members 11Z are the same. The inner-side distal end members 21Z and outer-side distal end members 11Z are softer than portions other than the distal end portions that are principal parts of the outer-side arms 11 and inner-side arms 21.

Modification Examples 3 and 4 of First Embodiment

Hereunder, insertion apparatuses 2C and 2D of modification examples of the first embodiment of the present invention are described referring to the drawings.

The insertion apparatuses 2C and 2D according to the present modification examples are similar to the insertion apparatus 2 of the first embodiment. Hence, the same components are designated by the same symbols, and a description of such components is omitted hereunder.

Figure 32:
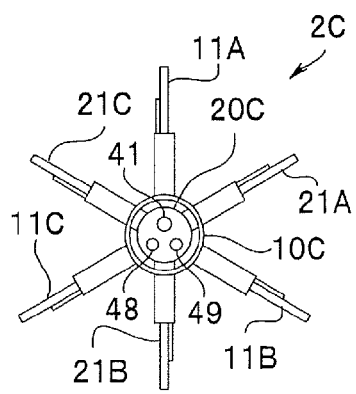
FIG. 32 is a view of an endoscope insertion apparatus according to modification example 3 of the first embodiment as observed from the distal end side thereof.

FIG. 32 is a view of an endoscope insertion apparatus according to modification example 3 of the first embodiment of the present invention as observed from the distal end side thereof. As shown in FIG. 32, the insertion apparatus 2C of modification example 3 is an endoscope in which an inner-side unit 20C has the image pickup section 41. In other words, the endoscope has functions of the inner-side unit 20C of the insertion apparatus 2C. The outer-side unit 10C is the same as the outer-side unit 10.

Figure 33:
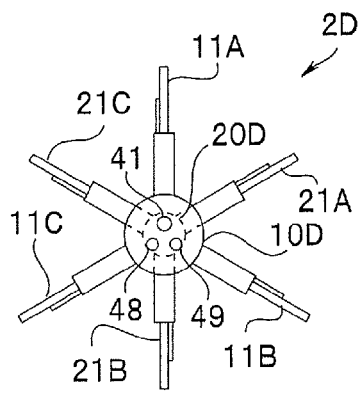
FIG. 33 is a view of an endoscope insertion apparatus according to modification example 4 of the first embodiment as observed from the distal end side thereof.

FIG. 33 is a view of an endoscope insertion apparatus according to modification example 4 of the first embodiment of the present invention as observed from the distal end side thereof. As shown in FIG. 33, the insertion apparatus 2D of modification example 4 is an endoscope in which an outer-side unit 10D has the image pickup section 41. In other words, the endoscope has functions of the outer-side unit 10D of the insertion apparatus 2C. The inner-side unit 20D is provided inside the insertion assisting section of the endoscope.

The insertion apparatus 2C in which the inner-side insertion assisting section has an image pickup section according to the modification example 3, the insertion apparatus 2D in which the outer-side insertion assisting section has an image pickup section according to the modification example 4, and the endoscope insertion apparatus in which the inner-side insertion assisting section has an insertion channel portion into which an endoscope that has an image pickup section can be inserted have similar advantages to the insertion apparatus 2 of the first embodiment.

Modification Examples 5 to 11 of First Embodiment

Hereunder, insertion apparatuses 2E to 2K of modification examples of the first embodiment of the present invention are described referring to the drawings.

The insertion apparatuses 2E to 2K according to the present modification examples are similar to the insertion apparatus 2 of the first embodiment. Hence, the same components are designated by the same symbols, and a description of such components is omitted hereunder. Further, while the following description takes the structure of inner-side fixing sections 63 to 123 as an example, an outer-side arm member that is not described below or illustrated in the drawings has the same structure.

Figure 34A:
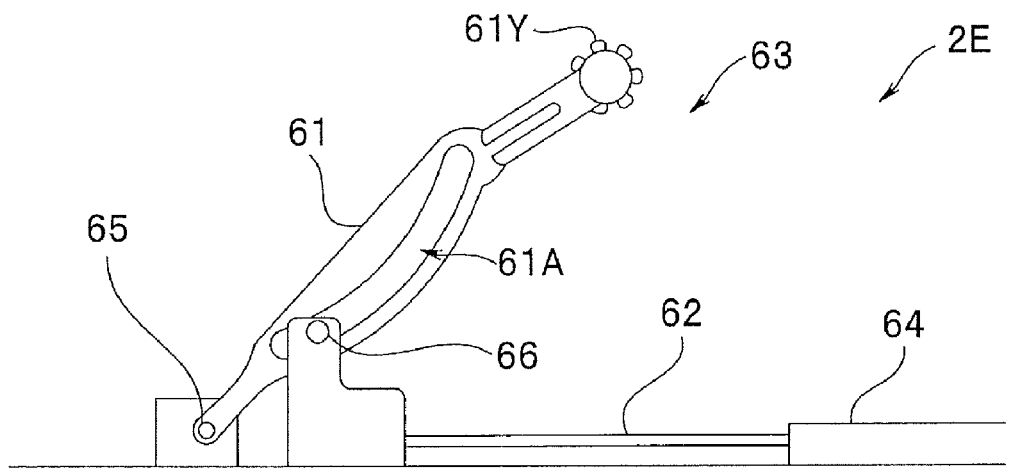
FIG. 34A is a side view of an outer-side fixing section of an endoscope insertion apparatus according to modification example 5 of the first embodiment.
Figure 34B:
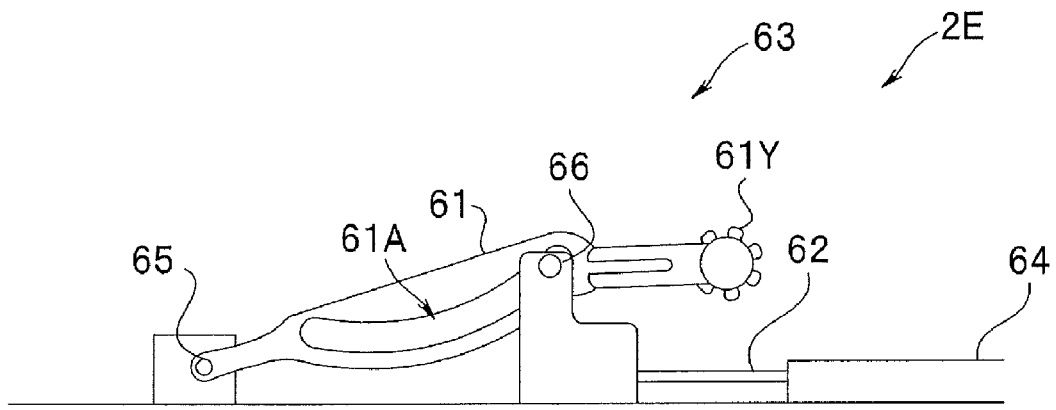
FIG. 34B is a side view of the outer-side fixing section of the endoscope insertion apparatus according to modification example 5 of the first embodiment.

As shown in FIG. 34A and FIG. 34B, in an inner-side fixing section 63 of the insertion apparatus 2E of modification example 5, an inner-side arm member 61 has a first cam groove 61A that engages with a first cam pin 66. In other words, the first cam groove 61A interfits with the first cam pin 66 in a manner that enables movement of the first cam groove 61A. The first cam pin 66 is moved by a pushing/pulling operation of an inner-side operation transmitting section 62, and is pivotally held by a first pivot 65.

As shown in FIG. 34A and FIG. 34B, the inner-side operation transmitting section 62 of the inner-side fixing section 63 of the insertion apparatus 2E is housed inside a guide pipe 64. Further, an inner-side arm member distal end portion 61Y is a separate element to the inner-side arm member 61 and is formed with a material that is softer than the inner-side arm member 61 and has projections and depressions on the surface thereof.

When the surgeon performs an operation to pull the inner-side operation transmitting section 62 to the proximal end portion side, since the first cam pin 66 is drawn to the proximal end portion side, the inner-side arm member 61 rotates around the pivot 65 that is the first pivot and enters a reduced diameter state.

More specifically, according to the insertion apparatus 2E, the inner-side arm member has a first cam groove that engages with a first cam pin that is moved by a pushing/pulling operation of the inner-side operation transmitting section and is pivotally held by a first pivot, and the outer-side arm member has a second cam groove that engages with a second cam pin that is moved by a pushing/pulling operation of the outer-side operation transmitting section and is pivotally held by a second pivot.

Figure 35:
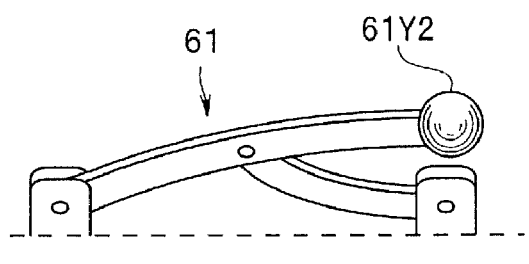
FIG. 35 is an oblique perspective view for describing a distal end portion of an arm member of an endoscope insertion apparatus.
Figure 36:
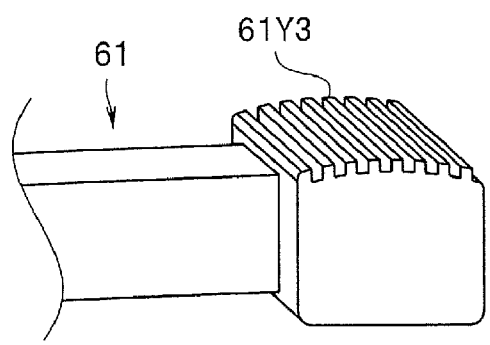
FIG. 36 is an oblique perspective view for describing a distal end portion of an arm member of an endoscope insertion apparatus.
Figure 37:
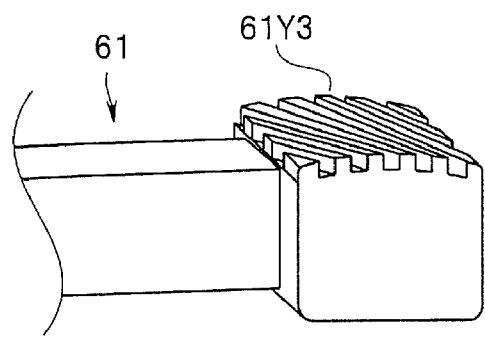
FIG. 37 is an oblique perspective view for describing a distal end portion of an arm member of an endoscope insertion apparatus.

The inner-side arm member distal end portion 61Y is an important component for securely fixing the insertion apparatus 2 to the intestinal wall 9. Therefore, a substantially spheroid distal end portion 61Y2 shown in FIG. 35 or a distal end portion formed from a curved surface can also be preferably used. Further, as shown in FIG. 36, a distal end portion 61Y3 in which projections and depressions are formed in a direction that is perpendicular to the insertion direction or, as shown in FIG. 37, a distal end portion 61Y4 in which projections and depressions are formed in a direction that is at an angle of approximately 45 degrees with respect to the insertion direction can also be preferably used as the contact surface with the intestinal wall 9. The distal end portion 61Y3 generates a large amount of friction with respect to the insertion direction, and the distal end portion 61Y4 generates a large amount of friction with respect to rotation of the insertion apparatus 2. Therefore, the distal end portion 61Y3 has a high fixing capacity with respect to the insertion direction of the insertion apparatus 2, and the distal end portion 61Y3 can prevent rotation of the insertion apparatus 2 inside a tube cavity.

In this connection, preferably the distal end portion is rounded at all angular portions including the portion with projections and depressions, and is formed with a soft material.

As described above, preferably the distal end portion of an arm member that presses the intestinal wall has a curved surface that is formed with a soft material. It is particularly preferable that grooves for increasing the fixing capability with respect to the intestinal wall are formed in the surface.

The insertion apparatus 2E of modification example 5 has similar advantages to the insertion apparatus 2 of the first embodiment.

Figure 38A:
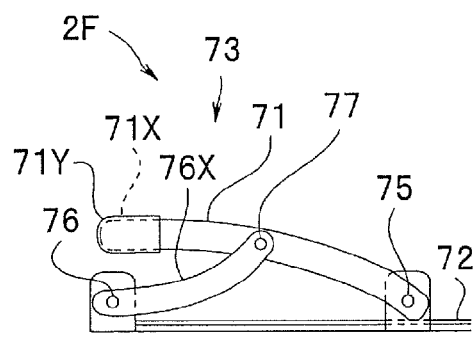
FIG. 38A is a side view of a fixing section of an endoscope insertion apparatus according to modification example 6 of the first embodiment.
Figure 38B:
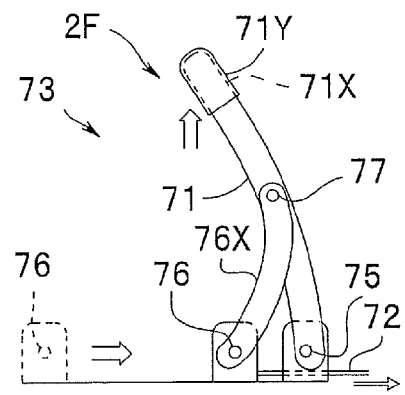
FIG. 38B is a side view of the fixing section of the endoscope insertion apparatus according to modification example 6 of the first embodiment.

As shown in FIG. 38A and FIG. 38B, an inner-side fixing section 73 of an insertion apparatus 2F of modification example 6 has a link mechanism that is different from the link mechanism of the inner-side fixing section 23 according to the first embodiment.

Further, as shown in FIG. 38A and FIG. 38B, in the insertion apparatus 2F, a pivot 75 and a pivot 76 of the inner-side fixing section 73 differ from the pivots of the endoscope insertion apparatuses described in the foregoing in the respect that the pivots 75 and 76 are single-sided support pivots that are supported from only one side, respectively, while the pivots of the endoscope insertion apparatuses described in the foregoing are double-sided support pivots that are supported from both sides.

According to the insertion apparatus 2F, when the surgeon performs an operation to pull the inner-side transmitting rod 72 in the proximal end portion direction, the inner-side arm member 71 rotates around the pivot 75 to enter an expanded diameter state, and when the surgeon performs an operation to push the inner-side transmitting rod 72 in the distal end portion direction, the inner-side arm member 71 enters a reduced diameter state.

The insertion apparatus 2F of modification example 6 has similar advantages to the insertion apparatus 2 of the first embodiment.

Further, in the insertion apparatus 2F, an inner-side arm member distal end portion 71X is covered with a cover 71Y that is formed using a soft resin. Thus, the same advantages are obtained as when the inner-side arm member distal end portion 71X is softer than the inner-side arm member 71.

Figure 39A:
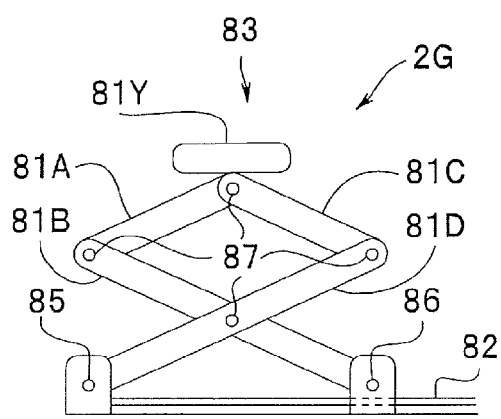
FIG. 39A is a side view of a fixing section of an endoscope insertion apparatus according to modification example 7 of the first embodiment.
Figure 39B:
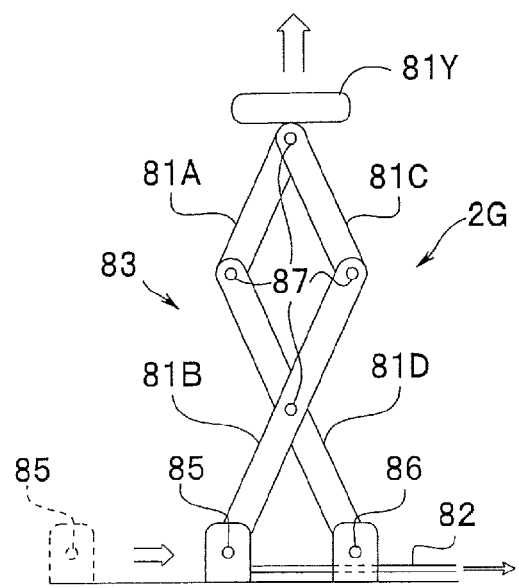
FIG. 39B is a side view of the fixing section of the endoscope insertion apparatus according to modification example 7 of the first embodiment.

As shown in FIG. 39A and FIG. 39B, an inner-side fixing section 83 of an insertion apparatus 2G according to modification example 7 presses an inner-side distal end member 81X against the intestinal wall 9 by a so-called "magic hand" method. More specifically, the inner-side fixing section 83 includes an inner-side arm member 81A, an inner-side arm member 81B, an inner-side arm member 81C, and an inner-side arm member 81D. Further, in the inner-side fixing section 83, an inner-side transmitting rod 82 is connected to a pivot 85.

Thus, according to the insertion apparatus 2G, when the surgeon performs an operation to push the inner-side transmitting rod 82 in the distal end portion direction, the inner-side arm member 81 enters a reduced diameter state. Further, when the surgeon performs an operation to pull the inner-side transmitting rod 82 in the proximal end portion direction, the inner-side arm member 81 enters an expanded diameter state.

The insertion apparatus 2G of modification example 7 has similar advantages to the insertion apparatus 2 of the first embodiment.

Figure 40A:
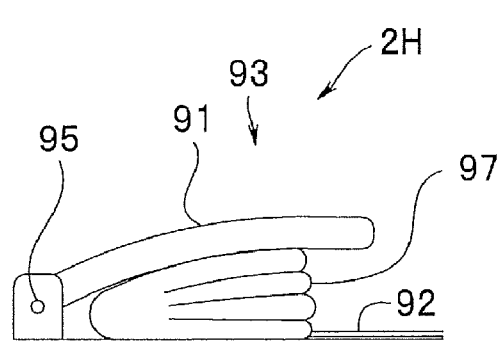
FIG. 40A is a side view of a fixing section of an endoscope insertion apparatus according to modification example 8 of the first embodiment.
Figure 40B:
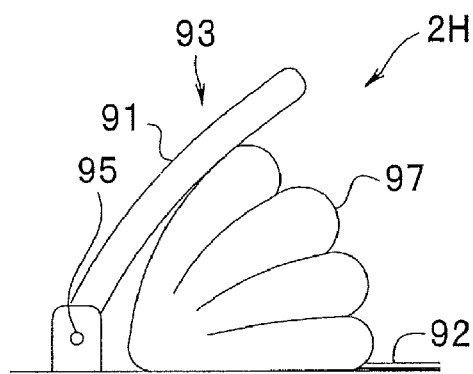
FIG. 40B is a side view of the fixing section of the endoscope insertion apparatus according to modification example 8 of the first embodiment.

As shown in FIG. 40A and FIG. 40B, a fixing section 93 of an insertion apparatus 2H of modification example 8 has a balloon 97 as an inner-side inflation/deflation portion that is inflatable and deflatable. The balloon 97 retains an inner-side arm 91 in an expanded diameter state when inflated, and retains the inner-side arm 91 in a reduced diameter state when deflated. The inner-side arm 91 rotates around a pivot 95. A supply and discharge tube 92 is connected to the balloon 97. The supply and discharge tube 92 is an inner-side supply and discharge section that is connected to a pump or the like that supplies or discharges a fluid to or from the balloon 97.

Preferably, the balloon 97 is, for example, an anisotropic inflation balloon that regulates inflation in a lateral direction by linking a plurality of balloons. The anisotropic inflation balloon, for example, may be formed by combining a plurality of balloons, or a direction in which it is desired to regulate the inflation direction may be restricted using a separate member.

More specifically, in the insertion apparatus 2H, an inner-side fixing section has an inner-side inflation/deflation portion that is inflatable and deflatable and that retains an inner-side arm member in an expanded diameter state when inflated and retains the inner-side arm member in a reduced diameter state when deflated, an outer-side fixing section has an outer-side inflation/deflation portion that is inflatable and deflatable and that retains an outer-side arm member in an expanded diameter state when inflated and retains the outer-side arm member in a reduced diameter state when deflated. The inner-side inflation/deflation portion includes an inner-side supply and discharge section that supplies or discharges a fluid. The outer-side inflation/deflation portion includes an outer-side supply and discharge section that supplies or discharges a fluid.

The insertion apparatus 2H not only has the same advantages as the insertion apparatus 2 of the first embodiment, but also has a simple structure since the arm member can be changed between an expanded diameter state and a reduced diameter state by means of fluid driving. Further, since the balloon 97 has elasticity, the arm member can be prevented from pressing excessively against the intestinal wall 9.

Figure 41A:
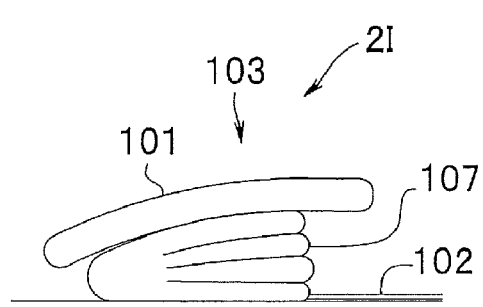
FIG. 41A is a side view of a fixing section of an endoscope insertion apparatus according to modification example 9 of the first embodiment.
Figure 41B:
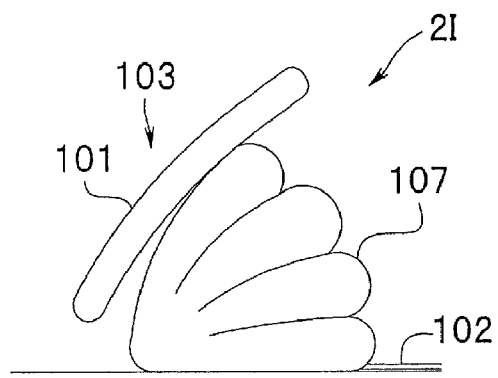
FIG. 41B is a side view of the fixing section of the endoscope insertion apparatus according to modification example 9 of the first embodiment.

As shown in FIG. 41A and FIG. 41B, a fixing section 103 of an insertion apparatus 2I of modification example 9 has a balloon 107 as an inner-side inflation/deflation portion that is inflatable and deflatable. The balloon 107 retains an inner-side arm 101 in an expanded diameter state when inflated, and retains the inner-side arm 101 in a reduced diameter state when deflated. According to the insertion apparatus 2I, only a side at one end of the inner-side arm 101 is fixed to the balloon 107. A supply and discharge tube 102 is connected to the balloon 107. The supply and discharge tube 102 is an inner-side supply and discharge section that is connected to a pump or the like that supplies or discharges a fluid to or from the balloon 107.

The insertion apparatus 2I not only has similar advantages to the insertion apparatus 2H of modification example 8 of the first embodiment, but also has a simpler structure.

Figure 42A:
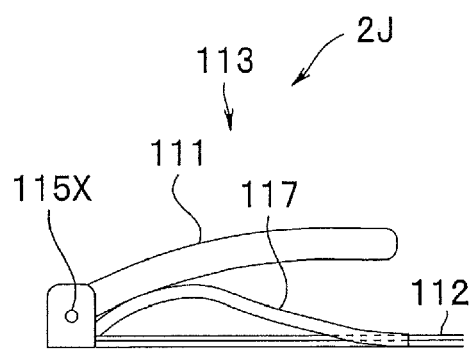
FIG. 42A is a side view of a fixing section of an endoscope insertion apparatus according to modification example 10 of the first embodiment.
Figure 42B:
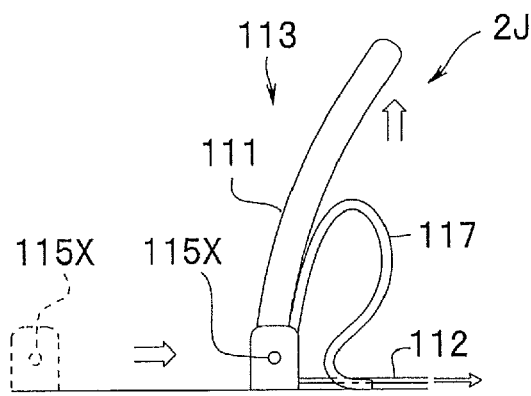
FIG. 42B is a side view of the fixing section of the endoscope insertion apparatus according to modification example 10 of the first embodiment.

As shown in FIG. 42A and FIG. 42B, a fixing section 113 of an insertion apparatus 2J of modification example 10 has an inner-side elastic fixing section 117 that is an inner-side elastic fixing section that retains the inner-side arm 111 in a reduced diameter state, and an inner-side operation transmitting section 112 that is connected to the inner-side arm 111 and that changes the position of the inner-side arm 111 to an expanded diameter state by compressing the inner-side elastic fixing section 117 by means of a pushing/pulling operation in the direction of the axis of advancement and retraction. The inner-side arm 111 rotates around a pivot 115X.

More specifically, in the insertion apparatus 2J, an inner-side fixing section has the inner-side elastic fixing section that retains the inner-side arm member in a reduced diameter state, and an outer-side fixing section has an outer-side elastic fixing section that retains an outer-side arm member in a reduced diameter state. The insertion apparatus 2J also includes an inner-side operation transmitting section that is connected to the inner-side arm member and changes the position of the inner-side arm member to an expanded diameter state by compressing the inner-side elastic fixing section by means of a pushing/pulling operation in the direction of the axis of advancement and retraction, and an outer-side operation transmitting section that is connected to the outer-side arm member and changes the position of the outer-side arm member to an expanded diameter state by compressing the outer-side elastic fixing section by means of a pushing/pulling operation in the direction of the axis of advancement and retraction.

The insertion apparatus 2J not only has similar advantages to the insertion apparatus 2 of the first embodiment, but can also prevent the arm members from pressing excessively against the intestinal wall 9 because the elastic fixing section has elasticity. Further, according to the insertion apparatus 2J, when the surgeon stops a pulling operation, the arm member automatically changes position to enter a reduced diameter state under the elastic force of the elastic fixing section. Therefore, the operability of the insertion apparatus 2J is better than the operability of the insertion apparatus 2. In this connection, the operation portion of the insertion apparatus 2J may have a stopper that can maintain the arm member in an expanded diameter state by fixing the operation transmitting section.

Figure 43A:
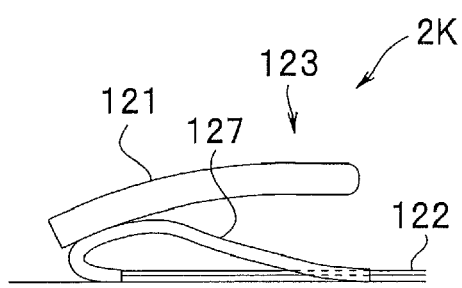
FIG. 43A is a side view of a fixing section of an endoscope insertion apparatus according to modification example 11 of the first embodiment.
Figure 43B:
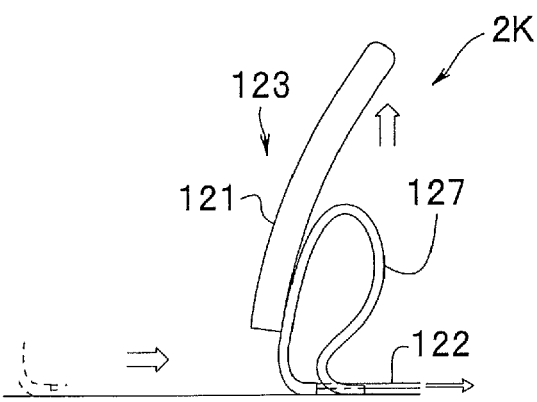
FIG. 43B is a side view of the fixing section of the endoscope insertion apparatus according to modification example 11 of the first embodiment.

As shown in FIG. 43A and FIG. 43B, an inner-side fixing section 123 of an insertion apparatus 2K of modification example 11 has an inner-side elastic fixing section 127 that is an inner-side elastic fixing section that retains an inner-side arm 121 in a reduced diameter state, and an inner-side operation transmitting section 122 that is connected to the inner-side arm 121 and that changes the position of the inner-side arm 121 to a reduced diameter state by compressing the inner-side elastic fixing section 127 by means of a pushing/pulling operation in the direction of the axis of advancement and retraction. Further, according to the insertion apparatus 2K, only a side at one end of the inner-side arm 121 is fixed to the inner-side elastic fixing section 127.

The insertion apparatus 2K not only has similar advantages to the insertion apparatus 2J of modification example 10 of the first embodiment, but also has a simpler structure.

Modification Example 12 of First Embodiment

Hereunder, an insertion apparatus 2L of modification example 12 of the first embodiment of the present invention is described referring to the drawings.

The insertion apparatus 2L according to the present modification example is similar to the insertion apparatus 2 of the first embodiment. Hence, the same components are designated by the same symbols, and a description of such components is omitted hereunder.

Figure 44:
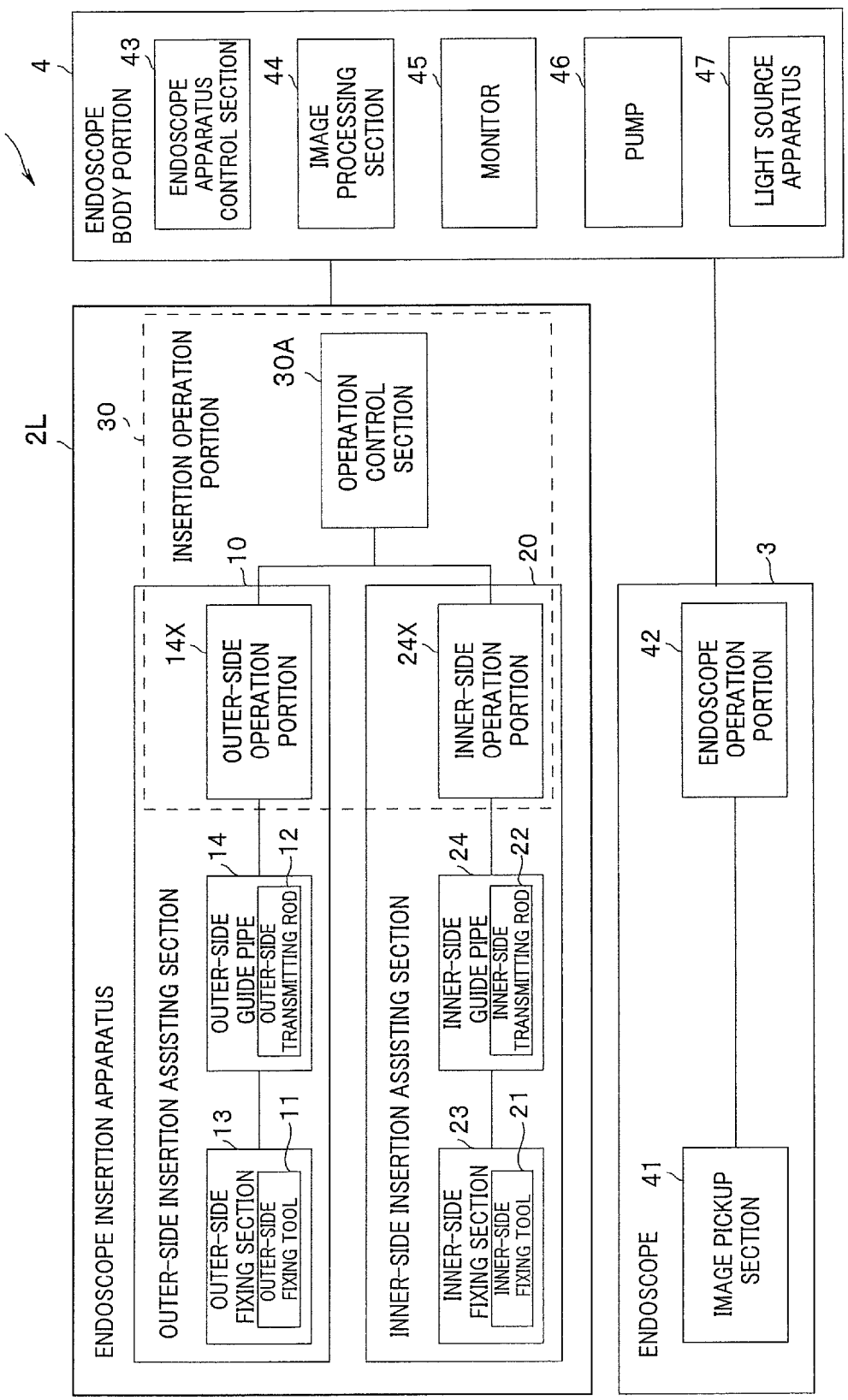
FIG. 44 is an overall configuration diagram of an endoscope apparatus that includes an endoscope insertion apparatus according to modification example 12 of the first embodiment.

As shown in FIG. 44, an insertion operation portion 30 of the insertion apparatus 2L of an endoscope apparatus 1L of modification example 12 further includes an operation control section 30A that automates the operations thereof.

According to the insertion apparatus 2 of the first embodiment, operations to change the positions of the outer-side arms 11 and the inner-side arms 21 between an expanded diameter state and a reduced diameter state and operations to advance or retract the outer-side unit 10 and the inner-side unit 20, more specifically, operations to change the relative positions of the inner-side insertion assisting section and the outer-side insertion assisting section, are all performed manually by the surgeon. In contrast, the insertion apparatus 2L of the present modification example 12 includes the operation control section 30A that carries out control to automatically perform at least any one of the aforementioned operations by means of an unshown motor or the like. Therefore, according to the insertion apparatus 2L, at least one of an operation to change a position of an arm member and an operation to advance or retract the outer-side unit 10 or the inner-side unit 20 can be performed automatically.

More specifically, the insertion apparatus 2L includes a control section that automatically performs at least one of an operation to change a position of the inner-side and outer-side arm members between an expanded diameter state and a reduced diameter state and an operation that changes the relative positions of the inner-side insertion assisting section and the outer-side insertion assisting section.

The insertion apparatus 2L has the advantages of the insertion apparatus 2 of the first embodiment, and also has the advantage of further reducing the burden of the surgeon since a position changing operation or an advancing or retracting operation can be automated according to the situation.

Modification Example 13 of First Embodiment

Hereunder, an insertion apparatus 2M of modification example 13 of the first embodiment of the present invention is described referring to the drawings. The insertion apparatus 2M is similar to the insertion apparatus 2 of the first embodiment and the like. Hence, the same components are designated by the same symbols, and a description of such components is omitted hereunder.

Figure 45A:
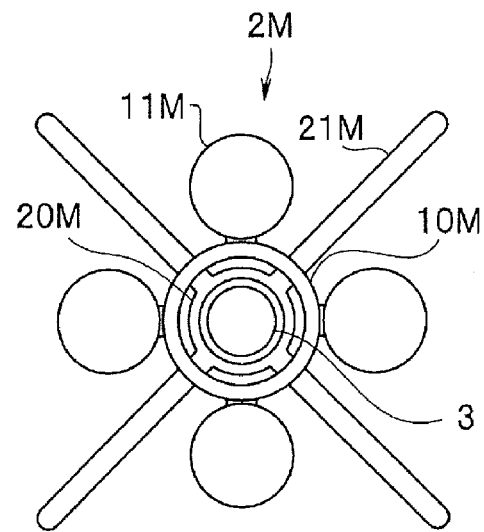
FIG. 45A is an exterior view for describing the configuration of an endoscope insertion apparatus according to modification example 13 of the first embodiment, that is a view as observed from the distal end side thereof.
Figure 45B:
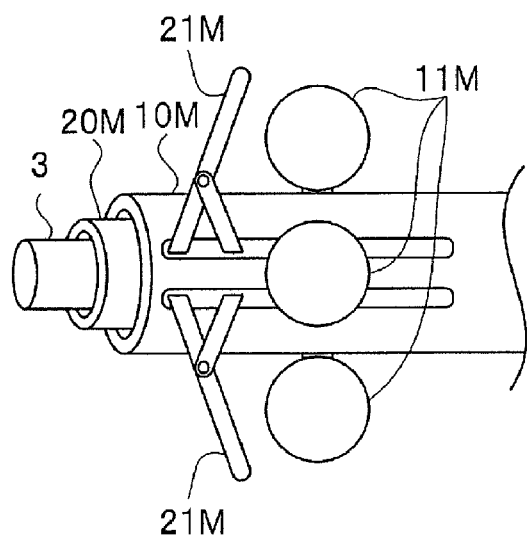
FIG. 45B is an exterior side view for describing the configuration of the endoscope insertion apparatus according to modification example 13 of the first embodiment.

As shown in FIG. 45A and FIG. 45B, the insertion apparatus 2M includes an inner-side unit 20M and an outer-side unit 10M. The inner-side unit 20M is the same as the inner-side unit 20 of the insertion apparatus 2. In contrast, the outer-side unit 10M presses the intestinal wall 9 not with arm members, but with balloons 11M that are inflatable and deflatable. The balloons 11M inflate upon receiving a supply of fluid from the pump 46 or the like, and press the intestinal wall 9. At this time, inner-side arms 21M that are in a reduced diameter state can be moved to the front or rear of the balloons 11M. Similarly, when the inner-side arms 21M are in an expanded diameter state, the deflated balloons 11M can be moved to the front or rear of the inner-side arms 21M. As described above, operation of the inflatable and deflatable balloons can, in other words, be regarded as an operation that can expand the diameter or reduce the diameter of the balloons.

More specifically, the insertion apparatus 2M is an endoscope insertion apparatus for inserting the endoscope 3 into a duct, including: an inner-side insertion assisting section in which inner-side arm members that press a duct wall are uniformly arranged in a circumferential direction on a distal end side of an inner-side insertion assisting section body portion; and an outer-side insertion assisting section that advances and retracts on the same axis as the inner-side insertion assisting section, in which outer-side balloon members that press the duct wall are uniformly arranged in a circumferential direction on a distal end side of an outer-side insertion assisting section body portion, and which is mounted to an outer circumferential portion of the inner-side insertion assisting section so that the inner-side arm members and the outer-side balloon members are alternately disposed in the circumferential direction; in which the outer-side balloon members and the inner-side arm members can be moved to an overlapping state in the insertion direction or can be moved to a state in which the outer-side balloon members and the inner-side arm members move forward and rearward with respect to each other in the insertion direction.

Since the outer-side unit 10 and the inner-side unit 20 of the insertion apparatus 2 each have mechanical arm members, the structure thereof may become a little complex. On the other hand, when an insertion assisting section that uses balloons for both the outer-side unit and the inner-side unit is used, an insertion operation may take a relatively long time because it takes time to inflate/deflate the balloons. In contrast, the insertion apparatus 2M has a simple structure while having similar advantages to the insertion apparatus 2, and an insertion operation using the insertion apparatus 2M can be performed comparatively quickly.

Modification Example 14 of First Embodiment

Hereunder, an insertion apparatus 2N of modification example 14 of the first embodiment of the present invention is described referring to the drawings. The insertion apparatus 2N is similar to the insertion apparatus 2M of modification example 13 and the like. Hence, the same components are designated by the same symbols, and a description of such components is omitted hereunder.

Although the insertion apparatus 2N is similar to the insertion apparatus 2M, it is not necessary for the surgeon to inflate/deflate balloons 11N during an insertion operation. More specifically, during an insertion operation the balloons 11N are maintained in a state in which the balloons 11N are inflated to a predetermined size. In this case, the term "predetermined size" refers to a size at which the balloons 11N can move to the front or rear of inner-side arms 21N that are in an expanded diameter state, that is, that press against the intestinal wall, and furthermore, a size that allows the inner-side arms 21N that are in a reduced diameter state to move to the front or rear of the balloons 11N.

Hereunder, a shortening operation (drawing-in operation) with respect to the large intestine using the insertion apparatus 2N according to modification example 14 is described using FIG. 46A to FIG. 50B.

Figure 46A:
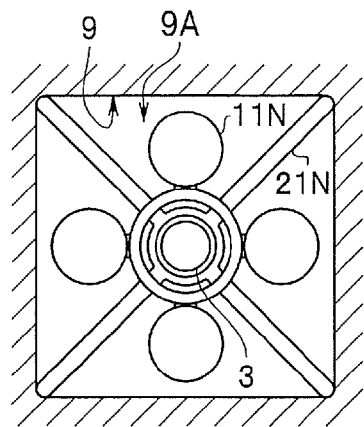
FIG. 46A is an exterior view for describing operation of an endoscope insertion apparatus according to modification example 14 of the first embodiment, that is a view as observed from the distal end side thereof.
Figure 46B:
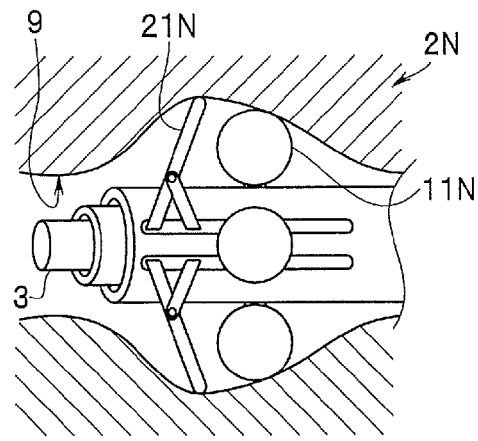
FIG. 46B is an exterior side view for describing operation of the endoscope insertion apparatus according to modification example 14 of the first embodiment.
Figure 47A:
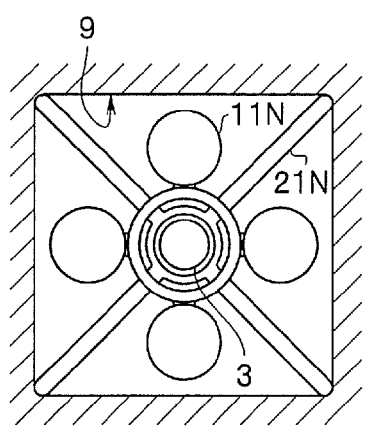
FIG. 47A is an exterior view for describing operation of the endoscope insertion apparatus according to modification example 14 of the first embodiment, that is a view as observed from the distal end side thereof.
Figure 47B:
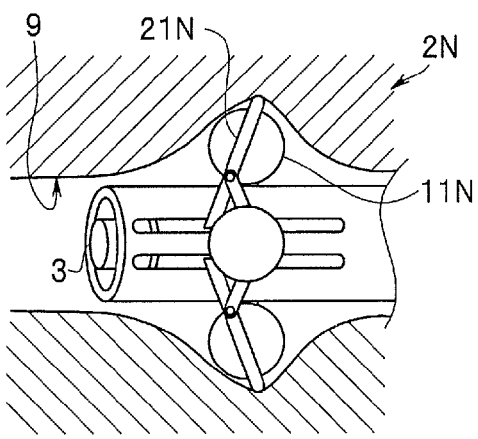
FIG. 47B is an exterior side view for describing operation of the endoscope insertion apparatus according to modification example 14 of the first embodiment.
Figure 48A:
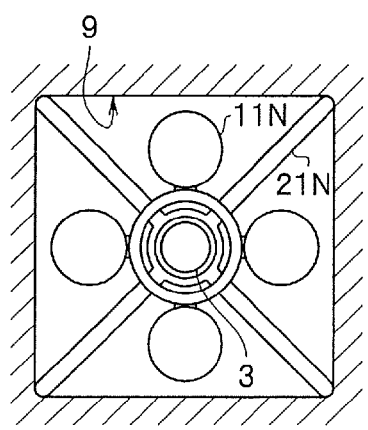
FIG. 48A is an exterior view for describing operation of the endoscope insertion apparatus according to modification example 14 of the first embodiment, that is a view as observed from the distal end side thereof.
Figure 48B:
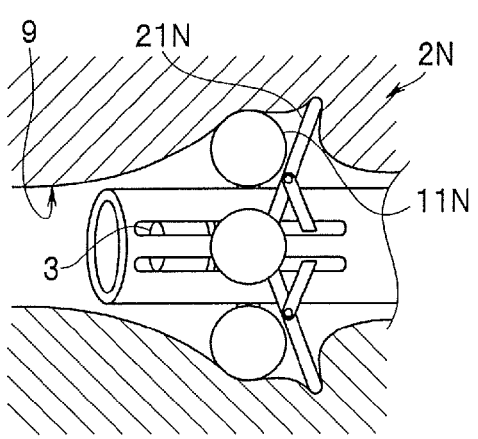
FIG. 48B is an exterior side view for describing operation of the endoscope insertion apparatus according to modification example 14 of the first embodiment.

The distal end portion side of the insertion apparatus 2N in which the inner-side arms 21N are in a reduced diameter state and the balloons 11N are in a deflated state is inserted into the intestinal tract 9A from the anus of the subject. Next, as shown in FIG. 46A and FIG. 46B, the surgeon inflates the balloons 11N to a predetermined size and also places the inner-side arms 21N into an expanded diameter state at a location that is further on the distal end side than the balloons 11N to thereby cause the inner-side arms 21N to press the intestinal wall 9.

Figure 49A:
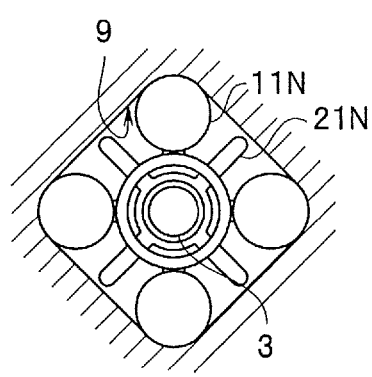
FIG. 49A is an exterior view for describing operation of the endoscope insertion apparatus according to modification example 14 of the first embodiment, that is a view as observed from the distal end side thereof.
Figure 49B:
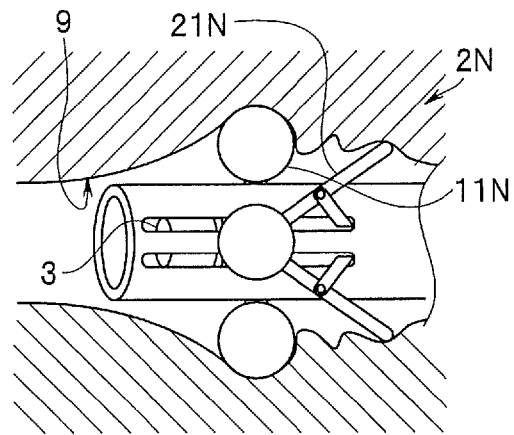
FIG. 49B is an exterior side view for describing operation of the endoscope insertion apparatus according to modification example 14 of the first embodiment.
Figure 50A:
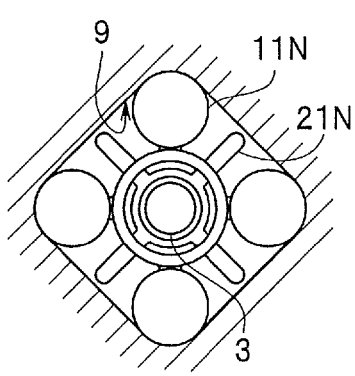
FIG. 50A is an exterior view for describing operation of the endoscope insertion apparatus according to modification example 14 of the first embodiment, that is a view as observed from the distal end side thereof.
Figure 50B:
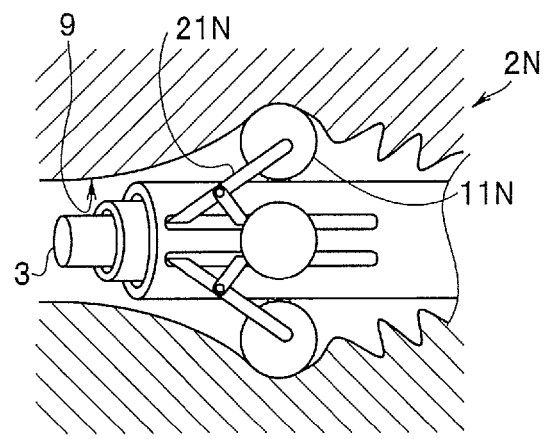
FIG. 50B is an exterior side view for describing operation of the endoscope insertion apparatus according to modification example 14 of the first embodiment.

Next, as shown in FIG. 47A, FIG. 47B, FIG. 48A, and FIG. 48B, when the surgeon draws the inner-side arms 21N that are in an expanded diameter state to the proximal end portion side, the intestinal tract 9A is pulled to the proximal end portion side by the inner-side arms 21N and is thereby shortened. At this time, the balloons 11N do not obstruct movement of the inner-side arms 21N. Subsequently, as shown in FIG. 49A and FIG. 49B, the surgeon places the inner-side arms 21N in a reduced diameter state. Since the shortened intestinal tract 9A is fixed by the balloons 11N at this time, the shortened state of the intestinal tract 9A is maintained. Next, as shown in FIGS. 50A and 50B, the surgeon pushes the inner-side arms 21N that are in a reduced diameter state towards the distal end portion side. At this time, the balloons 11N do not obstruct movement of the inner-side arms 21N. Next, the surgeon again causes the inner-side arms 21N to enter an expanded diameter state, more specifically, the state shown in FIG. 46A and FIG. 46B.

By repeating the procedures illustrated in FIG. 46A to FIG. 50B the surgeon can advance the endoscope insertion apparatus to a deep region side while drawing-in the intestine towards the surgeon, in other words, while shortening the intestinal tract 9A.

In this connection, although the insertion apparatus 2N is an endoscope insertion apparatus that includes the inner-side arms 21N and outer-side balloons 11N, similar advantages can be obtained with an endoscope insertion apparatus that includes the inner-side arms 21N and outer-side arm members that are fixed in a predetermined expanded diameter state. More specifically, in the insertion apparatus 2 and the like that are already described above, the endoscope insertion apparatus can also be advanced to a deep region side while performing an operation to shorten the intestinal tract 9A using the above described operating method.

Similar advantages can also be obtained by an endoscope insertion apparatus including inner-side balloons and outer-side arm members or by an endoscope insertion apparatus including inner-side arm members that are fixed in a predetermined expanded diameter state and outer-side arm members.

The method of using an endoscope insertion apparatus described above is a method of using an endoscope insertion apparatus for inserting an endoscope into a duct, having: an initial insertion step of inserting into an intestinal tract: an inner-side insertion assisting section in which a plurality of inner-side fixing sections having an inner-side arm member that is changeable between an expanded diameter state and a reduced diameter state and whose distal end portion is pressed and fixed against an intestinal wall in the expanded diameter state are uniformly arranged in a circumferential direction; and an outer-side insertion assisting section in which a plurality of outer-side fixing sections having a member that is changeable between an expanded diameter state and a reduced diameter state and that is pressed and fixed against an intestinal wall in the expanded diameter state are uniformly arranged in a circumferential direction, and in which slit portions that extend in a direction perpendicular to the circumferential direction and from which the inner-side arm members protrude when the outer-side insertion assisting section is mounted to an outer circumferential portion of the inner-side insertion assisting section are uniformly arranged in the circumferential direction between the outer-side fixing sections; an inner-side insertion assisting section fixing step of placing the inner-side fixing sections of the inner-side insertion assisting section in an expanded diameter state; an outer-side insertion assisting section fixing step of placing the outer-side fixing sections of the outer-side insertion assisting section into a predetermined expanded diameter state; a shortening step of shortening the duct by pulling back the inner-side insertion assisting section until the inner-side fixing sections move to the rear of the outer-side fixing sections; a step of releasing the fixed state of the inner-side insertion assisting section by placing the inner-side fixing sections in a reduced diameter state to release a state in which the inner-side fixing sections press the duct wall, and fixing the duct that has been shortened by means of the outer-side fixing sections; and an inner-side insertion assisting section insertion step of inserting the inner-side insertion assisting section until the inner-side fixing sections move to the front of the outer-side fixing sections.

Second Embodiment

An endoscope insertion apparatus 402 according to a second embodiment of the present invention is described hereunder with reference to the drawings.

Figure 51:
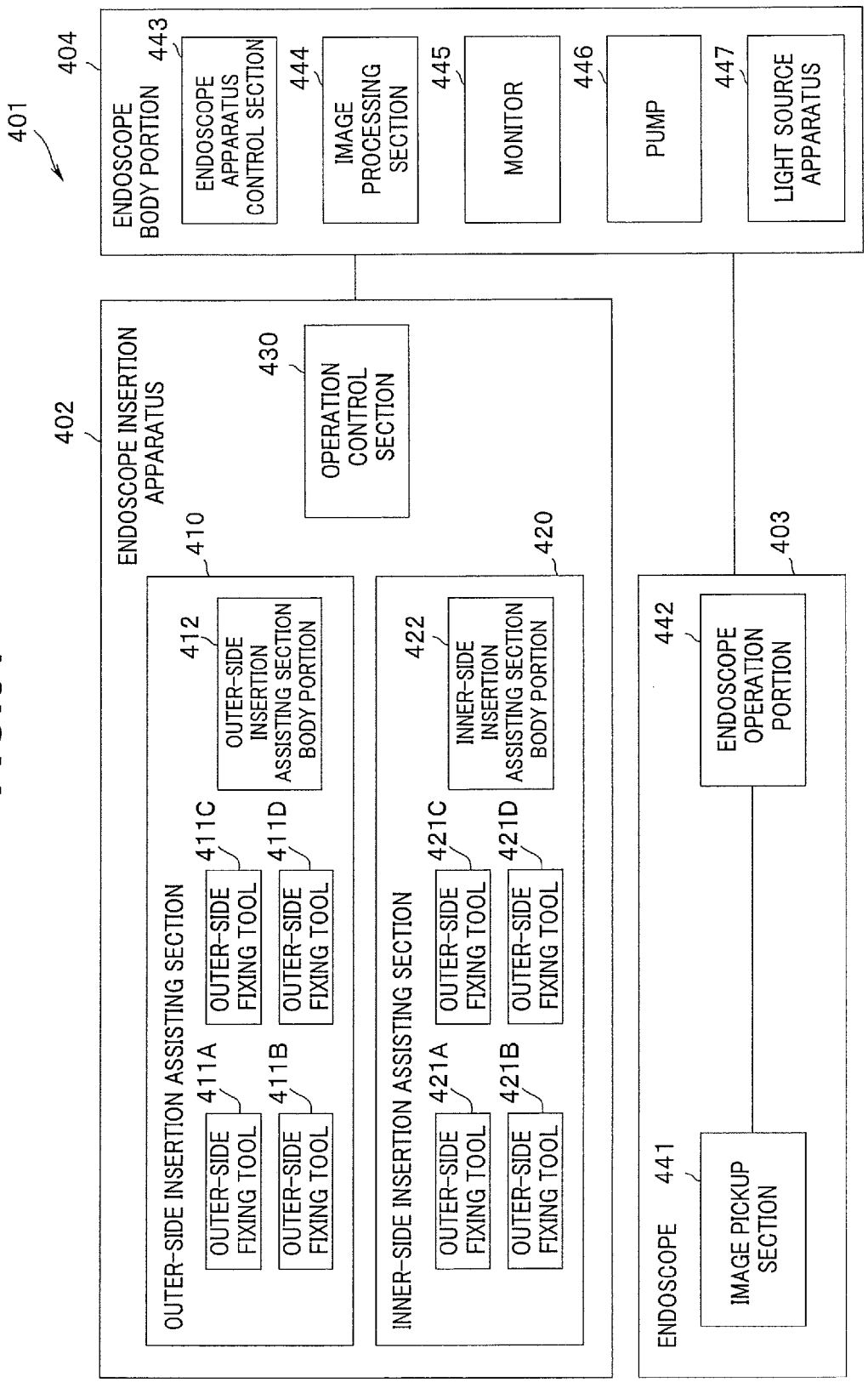
FIG. 51 is an overall configuration diagram of an endoscope apparatus that includes an endoscope insertion apparatus according to a second embodiment.

As shown in FIG. 51, an endoscope apparatus 401 has an endoscope 403, an endoscope insertion apparatus 402 for inserting a distal end portion of the endoscope 403 into a deep region of an intestinal tract 409A (see FIG. 56) that is an elongated duct, and an endoscope body portion 404. More specifically, the endoscope insertion apparatus 402 of the present embodiment is used in combination with the endoscope 403 that has an image pickup section 441 and an endoscope operation portion 442.

The endoscope body portion 404 has an endoscope apparatus control section 443, an image processing section 444, a monitor 445, a pump 446, and a light source apparatus 447. The endoscope apparatus control section 443 performs control of the endoscope apparatus 401. The image processing section 444 processes signals of images that have been photographed by the image pickup section 441 provided at the distal end portion of the endoscope 403. The monitor 445 displays images that have been processed by the image processing section 444. The pump 446 feeds air or water into the intestinal tract 409A through an opening 448 (see FIG. 52) in the distal end portion of the endoscope 403, or sucks fluid from inside the intestinal tract 409A. An illuminating light of the light source apparatus 447 is guided as far as an illumination section 449 (see FIG. 52) of the distal end portion of the endoscope 403.

The endoscope insertion apparatus 402 includes an inner-side insertion assisting section (inner-side unit) 420, an outer-side insertion assisting section (outer-side unit) 410, and an operation control section 430. The outer-side unit 410 has an elongated outer-side insertion assisting section body portion 412 (hereunder, referred to as "body portion 412") and four outer-side arm members (outer-side arms) 411A to 411D. The inner-side unit 420 has an elongated inner-side insertion assisting section body portion 422 (hereunder, referred to as "body portion 422") and four inner-side arm members (inner-side arms) 421A to 421D.

Hereunder, when each of a plurality of components that have the same structure is referred to, one alphabet character at the end of the symbol thereof is omitted. For example, when each of the outer-side arms 411A to 411D is referred to, the term "outer-side arms 411" is used. Further, when the outer-side unit 410 and the inner-side unit 420 have a similar structure, in some cases only one of the outer-side unit 410 and the inner-side unit 420 may be described.

Next, the structure of the endoscope insertion apparatus 402 is described using FIG. 52 to FIG. 58. The arrows in FIG. 54A to FIG. 54D indicate the insertion direction.

Figure 52:
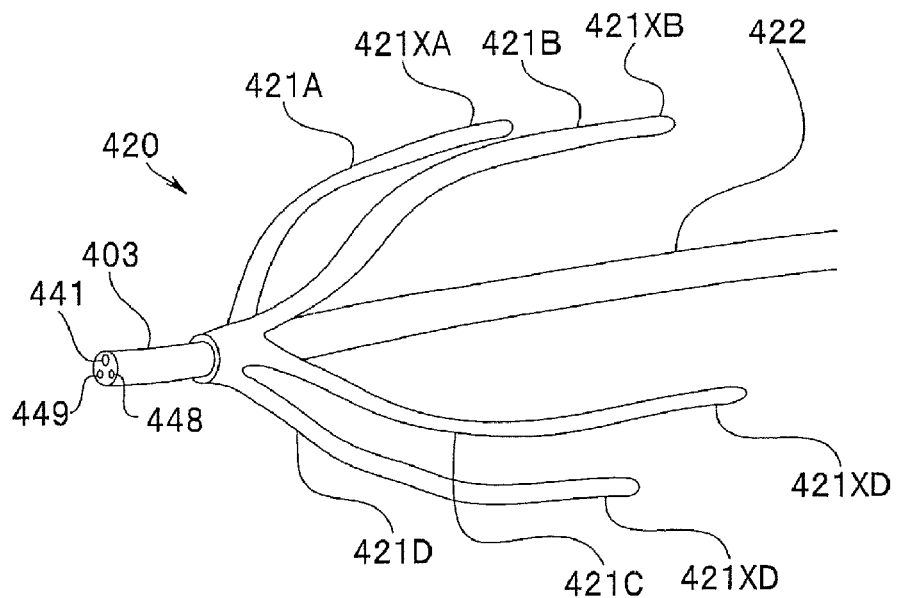
FIG. 52 is a perspective figure of the external appearance when an inner-side insertion assisting section according to the second embodiment is joined to an endoscope.
Figure 53:
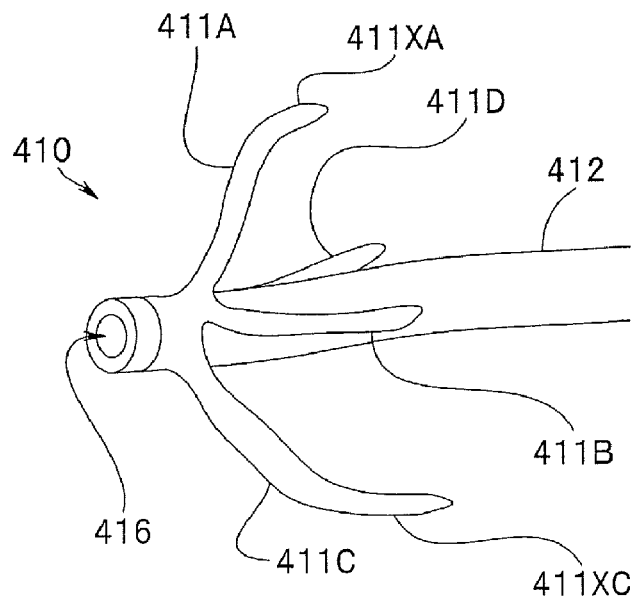
FIG. 53 is a perspective figure of the external appearance of an outer-side insertion assisting section according to the second embodiment.
Figure 54A:
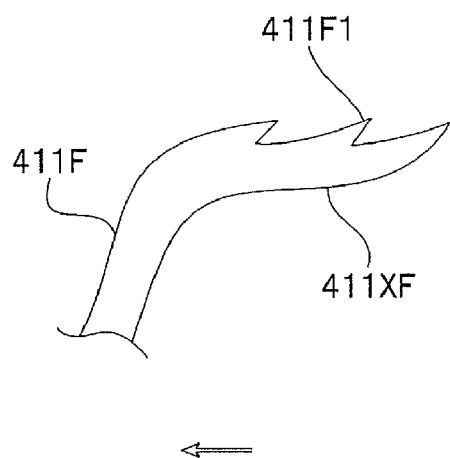
FIG. 54A is a view for describing the configuration of a distal end portion of an arm member according to the second embodiment.
Figure 54B:
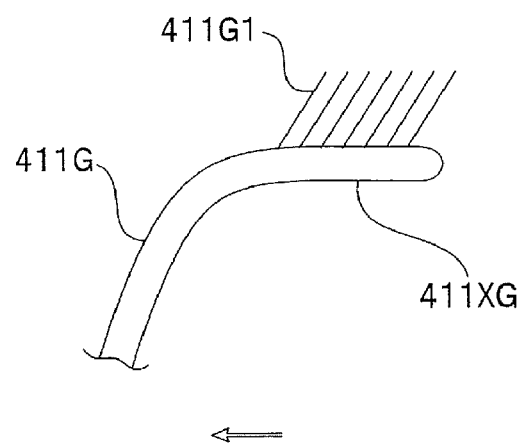
FIG. 54B is a view for describing the configuration of a distal end portion of an arm member according to the second embodiment.
Figure 54C:
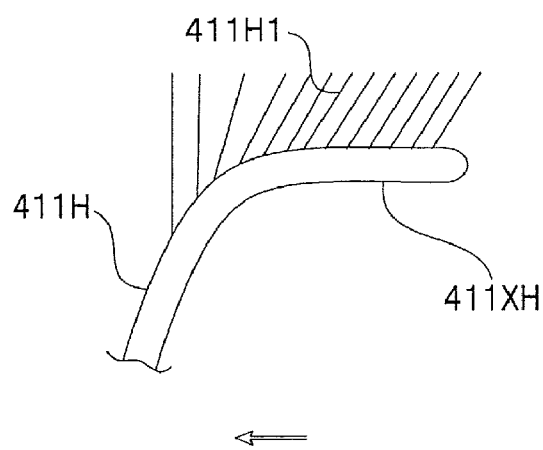
FIG. 54C is a view for describing the configuration of a distal end portion of an arm member according to the second embodiment.
Figure 54D:
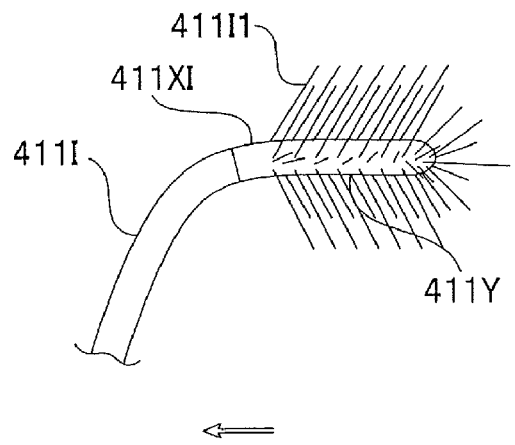
FIG. 54D is a view for describing the configuration of a distal end portion of an arm member according to the second embodiment.

As shown in FIG. 52, four inner-side arms 421A to 421D that are uniformly arranged on an outer circumferential portion of the inner-side unit 420 are elongated metal plates or resin plates or the like that each have elasticity. In an unloaded state the four inner-side arms 421A to 421D enter an expanded diameter state in which the inner-side arms 421A to 421D spread in a radial shape in a direction perpendicular to the circumferential direction. The inner-side unit 420 is mounted and fixed to an outer circumferential portion of the endoscope 403. Further, as shown in FIG. 53, four outer-side arms 411A to 411D that are uniformly arranged on the outer circumferential portion of the body portion 412 each have elasticity, and in an unloaded state the four outer-side arms 411A to 411D enter an expanded diameter state in which the outer-side arms 411A to 411D spread in a radial shape in a direction perpendicular to the circumferential direction. The body portion 412 of the outer-side unit 410 has an insertion channel portion 416 in a center part thereof through which the body portion 422 of the inner-side unit 420 can be inserted.

Outer-side arm member distal end portions (distal end portions) 411X that are distal end portions of the outer-side arms 411 of the endoscope insertion apparatus 402 shown in FIG. 54A to FIG. 54D have a structure such that friction in the insertion direction with respect to a duct wall, more specifically, the intestinal wall 409, is less than friction in a withdrawal direction. For example, a distal end portion 411XF shown in FIG. 54A has a plurality of protruding portions 411F1 that protrude in an opposite direction to the insertion direction of the endoscope insertion apparatus 402, or distal end portions 411X shown in FIG. 54B to FIG. 54D have slanted fibers 411G1, 411H1 or 411I1 that are provided at an angle so that spreading of the slanted fibers 411G1, 411H1 or 411I1 towards the insertion direction of the endoscope insertion apparatus 402 is decreased. In this connection, an anisotropic friction member 411Y that has slanted fibers 411I1 that are arranged in a radial shape is provided at a distal end portion 411X1 shown in FIG. 54D.

Although the amount of friction created at the distal end portions 411X exemplified in FIG. 54A to FIG. 54D is small when the distal end portions 411X move in a direction to insert the outer-side arms 411, the amount of friction created when moving in a direction to withdraw the outer-side arms 411 is large. Consequently, when inserting the endoscope insertion apparatus 402, even if a force is applied in a direction to withdraw the outer-side arms 411, the outer-side arms 411 can continue to be fixed to the intestinal wall 409. In this connection, details of the distal end portion 411X are not shown in other drawings in order to simplify the diagrammatic representation.

Figure 55:
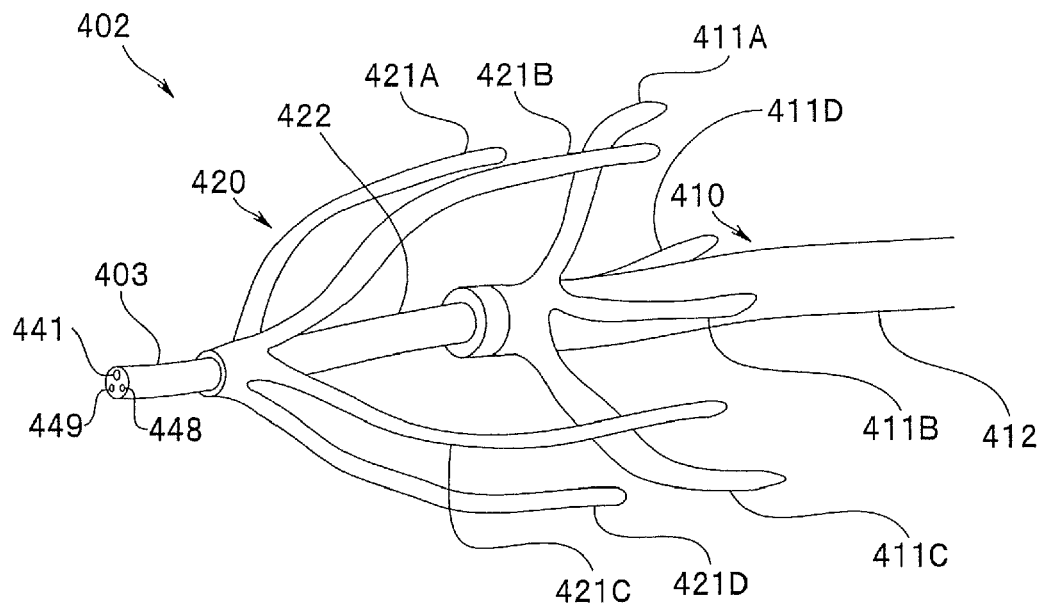
FIG. 55 is a perspective figure of the external appearance when the endoscope insertion apparatus according to the second embodiment is joined to an endoscope.

Next, as shown in FIG. 55, the outer-side unit 410, the inner-side unit 420, and the endoscope 403 are combined and used. More specifically, the endoscope 403 is mounted and fixed to an inner circumferential portion of the body portion 422. The outer-side unit 410 is movably mounted to an outer circumferential portion of the body portion 422. Consequently, the outer-side unit 410 can advance and retract to the front and rear on the same axis as the inner-side unit 420, more specifically, with respect to the insertion direction.

Further, the outer-side arms 411 are alternately arranged on a distal end portion of the body portion 412 at an angle such that spreading thereof decreases towards the insertion direction in a circumferential direction of the axis of advancement and retraction, and the inner-side arms 421 are alternately arranged on a distal end portion of the body portion 422 at an angle such that spreading thereof decreases towards the insertion direction in a circumferential direction of the axis of advancement and retraction. Further, the body portion 412 of the outer-side unit 410 is mounted to an outer circumferential portion of the body portion 422 of the inner-side unit 420 such that the outer-side arms 411 and the inner-side arms 421 are disposed in an equally spaced condition in the circumferential direction.

In the endoscope insertion apparatus 402, the length of the inner-side arms 421 is longer than the length of the outer-side arms 411 in the direction of the axis on which the outer-side unit 410 advances and retracts, more specifically, the insertion direction. Consequently, as described later, when the outer-side unit 410 moves forward in the insertion direction, in other words, moves in the direction of a deep region of the intestinal tract 409A, the distal end portions 411X move to the deep region side of the distal end portions 421X.

Figure 56:
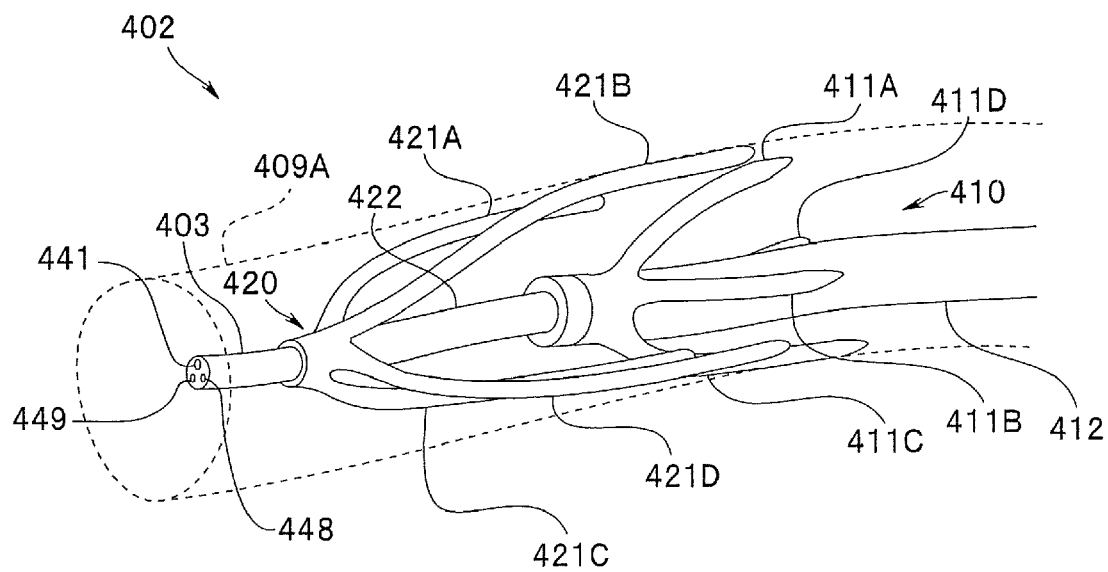
FIG. 56 is a perspective figure of the external appearance when the endoscope insertion apparatus according to the second embodiment is joined to an endoscope that shows a state in which the endoscope insertion apparatus has been inserted inside the intestine.
Figure 57:
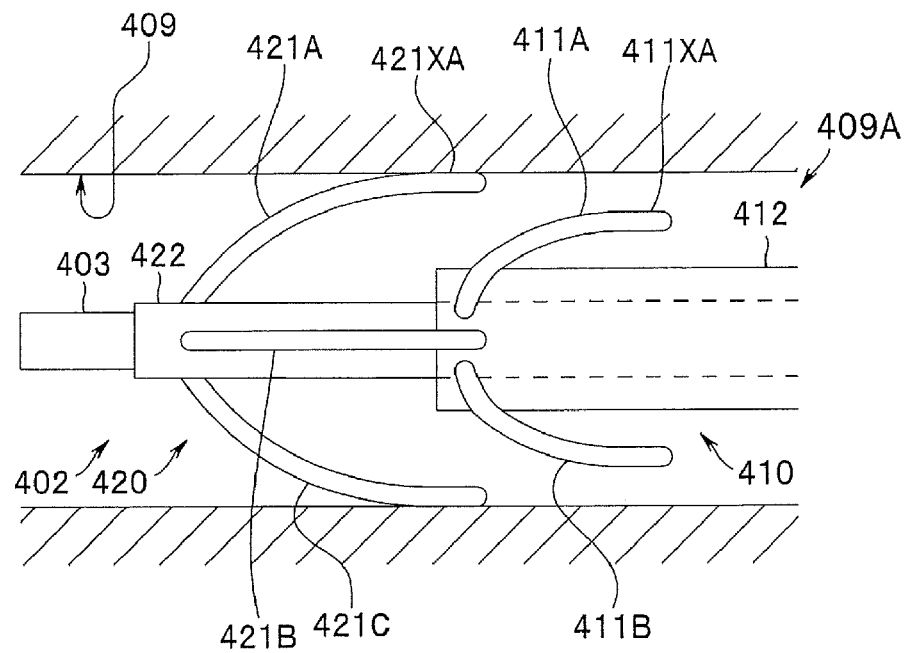
FIG. 57 is a schematic diagram as viewed from a lateral direction showing a state when the endoscope insertion apparatus according to the second embodiment is joined to an endoscope in a state in which the endoscope insertion apparatus has been inserted inside the intestine.
Figure 58:
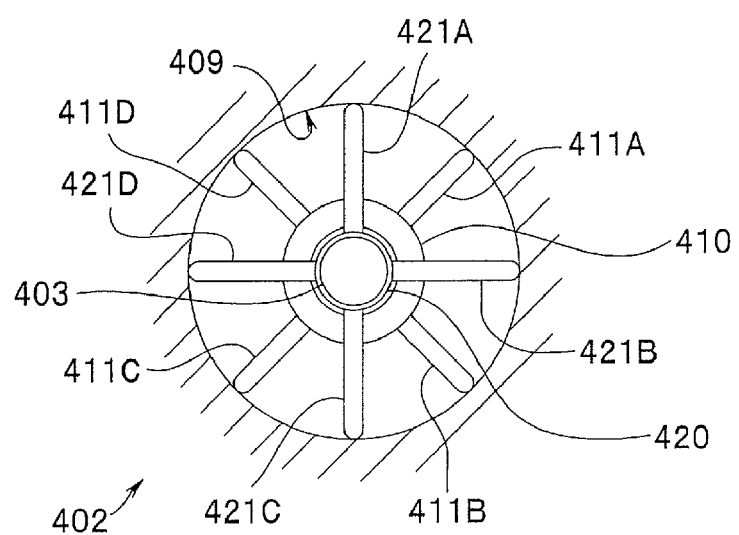
FIG. 58 is a schematic diagram as viewed from an insertion direction showing a state when the endoscope insertion apparatus according to the second embodiment of the present invention is joined to an endoscope in a state in which the endoscope insertion apparatus has been inserted inside the intestine.

As shown in FIG. 56 and FIG. 57, when the endoscope insertion apparatus 402 is inserted into the intestinal tract 409A, the outer-side arms 411 and the inner-side arms 421 change from an expanded diameter state in an unloaded condition (see FIG. 55) to a reduced diameter state that is in accordance with the size of the space inside the intestinal wall 409. Inside the intestinal tract 409A, the outer-side arms 411 and inner-side arms 421 are fixed to the intestinal wall 409 by pressing the intestinal wall 409 by means of the elastic force of the outer-side arms 411 and inner-side arms 421, respectively.

As described previously, as shown in FIG. 58, the outer-side arms 411 and inner-side arms 421 are alternately arranged in the circumferential direction of the axis of advancement and retraction. Preferably, the spaces between the outer-side arms 411 are inner-side arms 421 are equal.

As described above, in the endoscope insertion apparatus 402, the distal end portions 411X and the distal end portions 421X can be moved to an overlapping state in the insertion direction or can be moved to a state in which the distal end portions 411X and the distal end portions 421X move forward and rearward with respect to each other in the insertion direction.

In other words, according to the endoscope insertion apparatus 402, the distal end portions 411X and distal end portions 421X can be moved to at least an overlapping state in a direction that is perpendicular to the circumferential direction of the body portion 412, and preferably can be moved so as to pass by each other in the forward and rearward directions.

In this connection, the direction of the axis on which the outer-side arms 411 and the inner-side arms 421 advance and retract, the direction of the axis of the body portion 412 and the body portion 422, the direction perpendicular to the circumferential direction of the body portion 412 and the body portion 422, and the insertion direction and withdrawal direction of the endoscope insertion apparatus 402 are the same directions.

Figure 59:
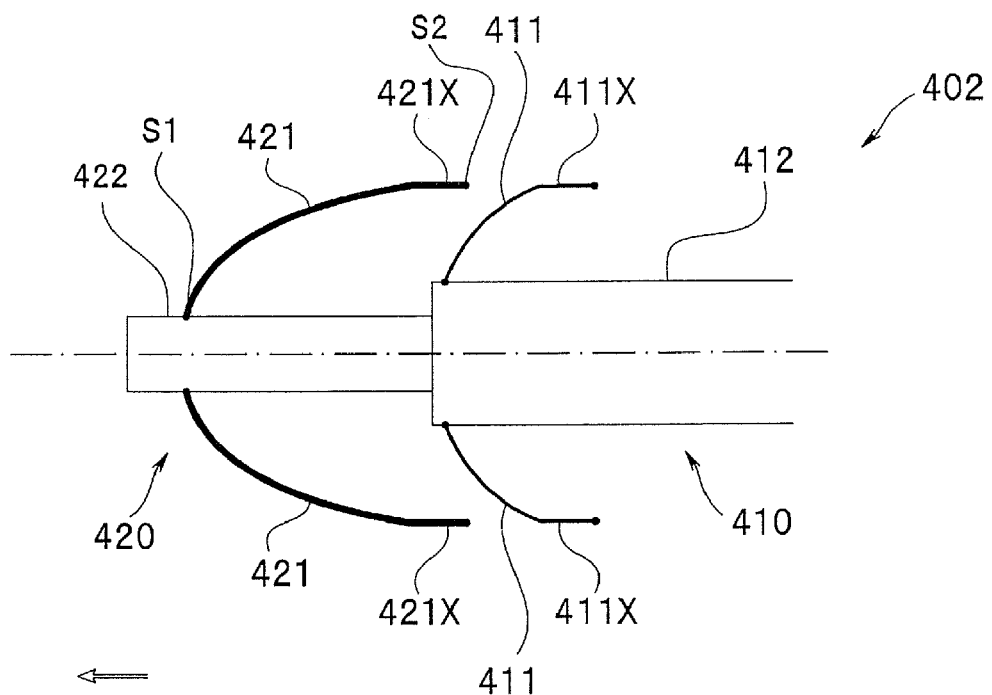
Figure 60:
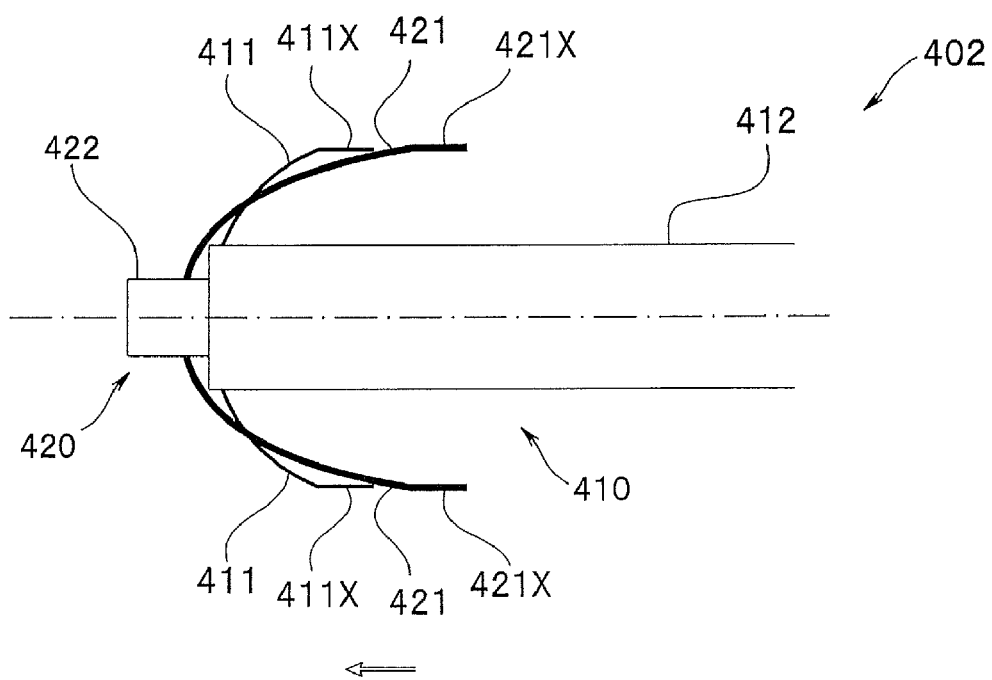

Next, a method of using the endoscope insertion apparatus 402 is described using FIG. 59 to FIG. 61D. In this connection, in FIG. 59 to FIG. 61A, and FIG. 61A to FIG. 61D, to facilitate the description, the outer-side arms 411 and the inner-side arms 421 are illustrated so as to appear above and below the center axis in the same manner. Further, the arrows shown in FIG. 59 and FIG. 60 represent the insertion direction.

FIG. 59 is a view that illustrates a state in which the outer-side unit 410 and the inner-side unit 420 are separated by a large distance on the same axis. FIG. 60 is a view that illustrates a state in which the outer-side unit 410 and the inner-side unit 420 are adjacent to each other on the same axis.

As already described, the endoscope insertion apparatus 402 is mounted to the outer circumferential portion of the body portion 422, and has an outer-side unit 410 that advances and retracts on the same axis as the inner-side unit 420. The length of inner-side arms 421 is longer than the length of outer-side arms 411. In this case, the term "length" of an arm member refers to, when taking the inner-side arm 421 as an example, a length from a connection portion S1 at which the inner-side arm 421 is connected to the body portion 422 to an other end portion S2 of the inner-side arm 421. As shown in FIG. 59, the connection portion of the outer-side arm 411 is at or adjacent to the distal end portion of the outer-side unit 410.

Therefore, as shown in FIG. 60, in a state in which the distal end portion of the outer-side unit 410 and the distal end portion of the inner-side unit 420 are adjacent, the distal end portions 411X are disposed at a position that is more forward in the insertion direction than the distal end portions 421X, more specifically, at a position on the deep region side of the intestinal tract 409A. In this connection, it is sufficient that the distal end portions 411X can be moved at least as far as the same position in the insertion direction as the distal end portions 421X, more specifically, as far as the same insertion depth as the distal end portions 421X.

Next, the method of using the endoscope insertion apparatus of the present embodiment is described using FIG. 61A to FIG. 61D.

<Initial Insertion Step>

The surgeon pushes the endoscope insertion apparatus 402 having the endoscope 403 fixed at a distal end portion thereof into the rectum from the anus of the subject. Although the outer-side arms 411 and inner-side arms 421 are in an expanded diameter state at this time, because the friction in the insertion direction with respect to the intestinal wall 409 of the distal end portion 411X and distal end portion 421X is comparatively small, it is not difficult to insert the endoscope insertion apparatus 402 into the intestine. The outer-side arms 411 and inner-side arms 421 of the endoscope insertion apparatus 402 that has been inserted into the intestine press the intestinal wall 409 by means of their own elastic force.

Figure 61A:
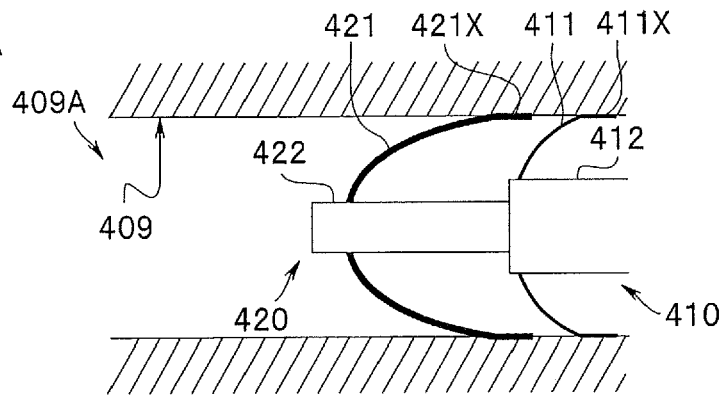

<Inner-side Insertion Assisting Section Insertion Step> FIG. 61A

The surgeon pushes only the inner-side unit 420 further in towards a deep region of the intestinal tract 409A. More specifically, the surgeon advances the inner-side arms 421 together with the body portion 422. When the inner-side unit 420 is pushed in, a force in the withdrawal direction produced by the reactive force thereof acts on the outer-side unit 410. However, because the amount of friction of the distal end portions 411X of the outer-side unit 410 is large in the withdrawal direction, the outer-side unit 410 moves little with respect to the intestinal tract 409A.

Figure 61B:
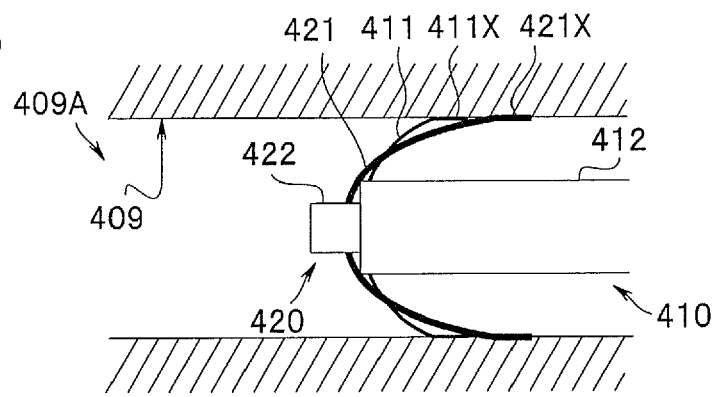

<Outer-side Insertion Assisting Section Insertion Step> FIG. 61B

Using the inner-side unit 420 as a guide, the surgeon pushes in the outer-side unit 410 until reaching a position at which the distal end portions 411X are located more forward in the insertion direction than the inner-side arms 421. When the outer-side unit 410 is pushed in, a force in the withdrawal direction produced by the reactive force thereof acts on the inner-side unit 420. However, because the amount of friction of the inner-side arm member distal end portions (distal end portions) 421X of the inner-side unit 420 is large in the withdrawal direction, the inner-side unit 420 moves little with respect to the intestinal tract 409A.

Further, because the outer-side unit 410 moves to a position at which the distal end portions 411X are more forward in the insertion direction than the inner-side arms 421, in other words, a position at a deeper region of the intestinal tract 409A, even if the intestinal tract 409A is shortened during the movement, the shortening of the intestinal tract 409A is released when the movement is completed.

Figure 61C:
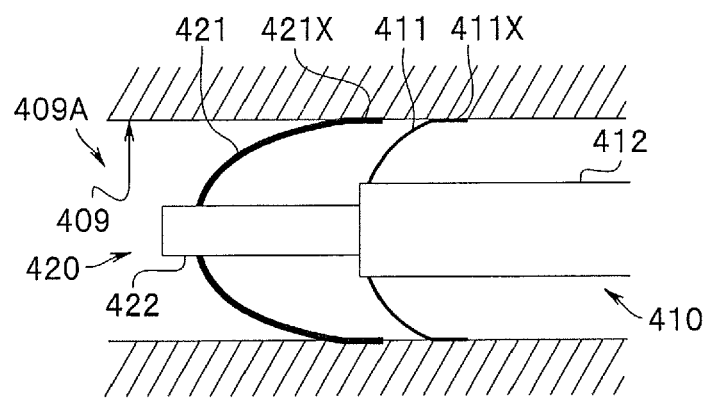

<Inner-side Insertion Assisting Section Insertion Step> FIG. 61C

The procedures in this step are the same as in the above described inner-side insertion assisting section insertion step.

Figure 61D:
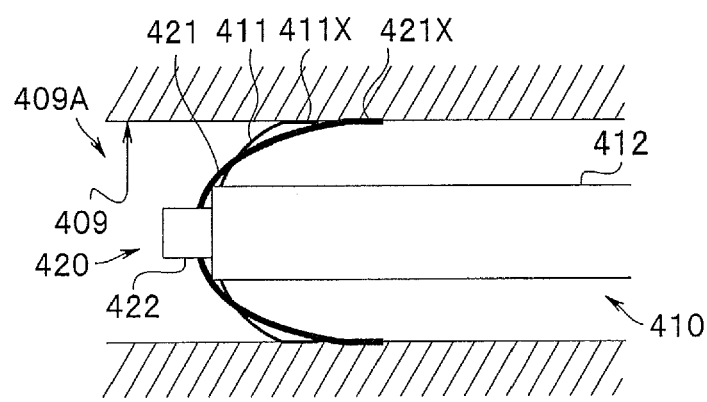

<Outer-side Insertion Assisting Section Insertion Step> FIG. 61D

The procedures in this step are the same as in the above described outer-side insertion assisting section insertion step.

By repeating the inner-side insertion assisting section insertion step and the outer-side insertion assisting section insertion step, the endoscope insertion apparatus 402 can insert the endoscope 403 into a deep region of the intestinal tract 409A by performing simple operations.

In this connection, operations to move the outer-side unit 410 and the inner-side unit 420 may be manually performed by the surgeon or may be performed by the operation control section 430 automatically controlling an unshown drive section.

In the foregoing description, an endoscope insertion apparatus 402 is exemplified that inserts a distal end portion of the endoscope 403 as a separate member attached to the endoscope insertion apparatus 402 into a deep region of the intestinal tract 409A. However, a configuration may also be adopted in which the outer-side insertion assisting section or the inner-side insertion assisting section is one portion of an endoscope that has an image pickup section.

Third Embodiment

Hereunder, an endoscope insertion apparatus according to a third embodiment of the present invention is described using the drawings. An endoscope insertion apparatus 402B of the present embodiment is similar to the endoscope insertion apparatus 402 of the second embodiment. Hence, the same components are designated by the same symbols, and a description of such components is omitted below.

Similarly to the endoscope insertion apparatus 402 of the second embodiment, in the endoscope insertion apparatus 402B, the friction in the insertion direction with respect to the intestinal wall 409 of the distal end portions 411X and distal end portions 421X that press the intestinal wall 409 is less than the friction in the withdrawal direction. Therefore, if the endoscope insertion apparatus 402B is removed while the distal end portions 411X and distal end portions 421X press against the intestinal wall 409, a comparatively large amount of friction occurs between the insertion assisting section distal end portions and the intestinal wall 409.

Figure 62:
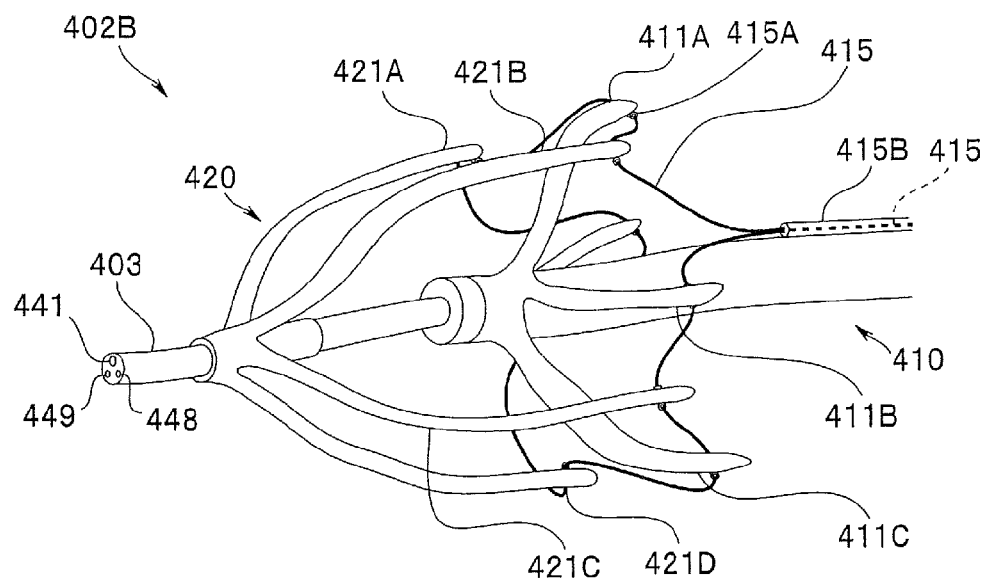

However, as shown in FIG. 62, the endoscope insertion apparatus 402B of the present embodiment includes a wire 415 as a traction portion that draws the distal end portions 411X and distal end portions 421X in the direction of the central axis of the elongated body portion 412, more specifically, the direction of the central axis of the body portion 422, to thereby release the state in which the outer-side arms 411 and inner-side arms 421 press the intestinal wall 409.

The wire 415 is inserted through wire insertion pipes (guide pipes) 415A that are provided on each of the distal end portions 411X and distal end portions 421X. The wire 415 passes through the inside of a wire guide tube 415B and extends to the proximal end portion side, so that the surgeon can perform an operation to pull the wire 415 from the proximal end portion side.

Figures 63A, 63B:
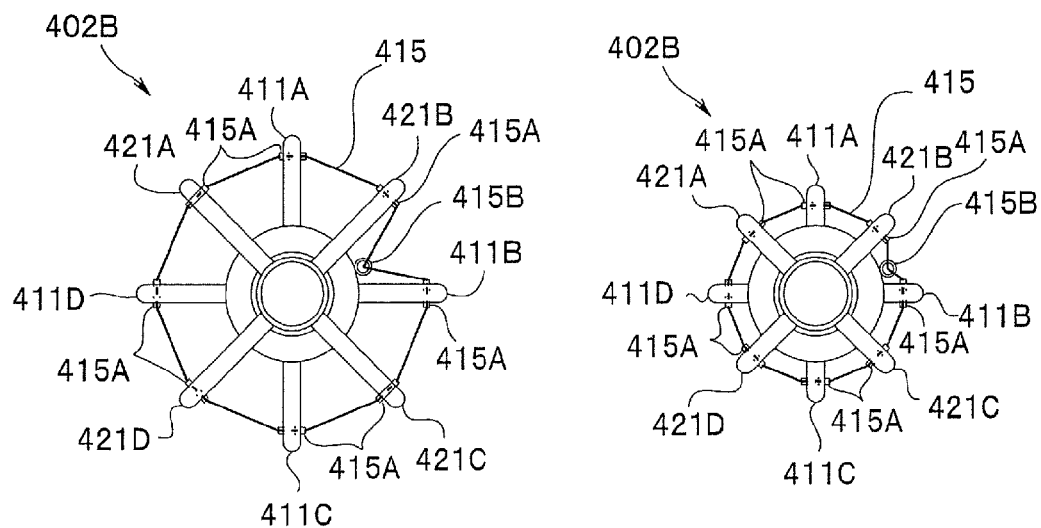

As shown in FIG. 63A and FIG. 63B, in the endoscope insertion apparatus 402B, when the wire 415 is subjected to a pulling operation from the proximal end portion side, the arm members that have been in an expanded diameter state because of the elastic force thereof are drawn in the diameter-reducing direction. When the pulling operation from the proximal end portion side is released, more specifically, when the wire 415 loosens, the arm members again enter an expanded diameter state as a result of the elastic force thereof. The arm members in a reduced diameter state hardly press against the intestinal wall 409

Figure 64A:
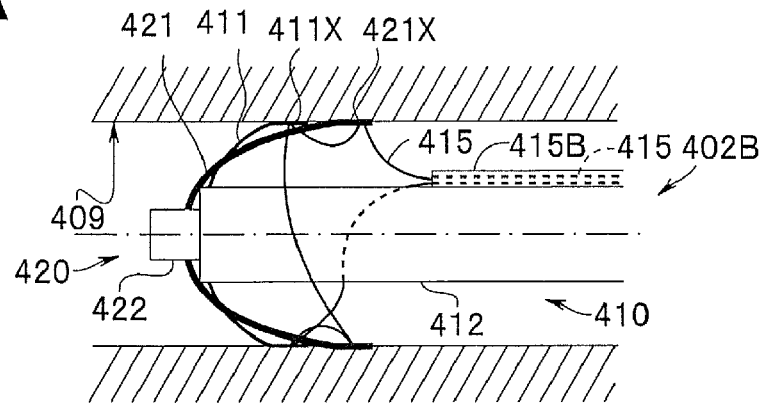
Figure 64B:
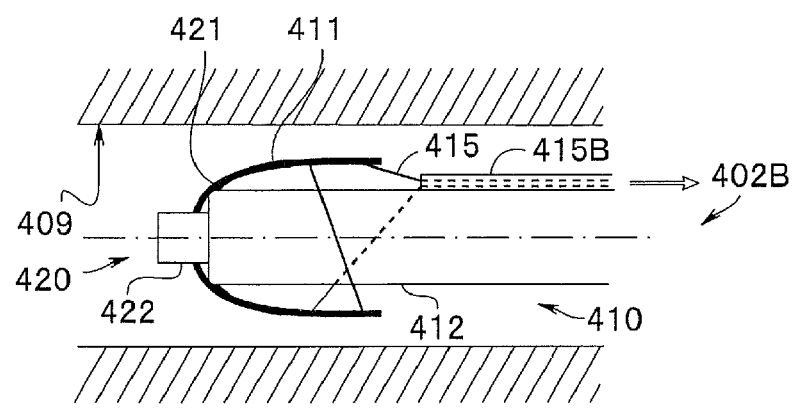
Figure 64C:
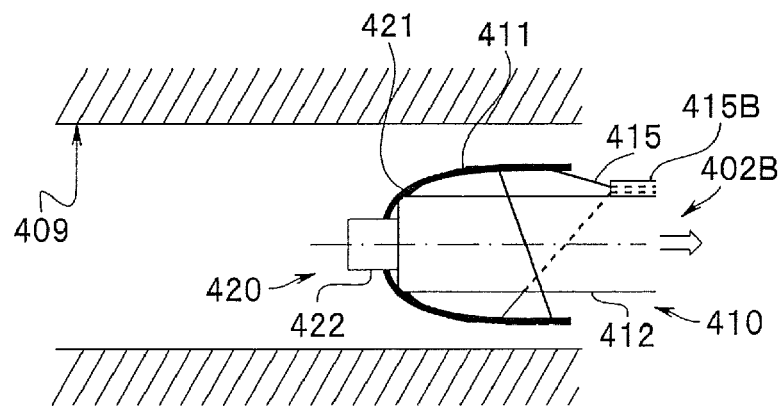

Next, a method of withdrawing the endoscope insertion apparatus 402B is described using FIG. 64A to FIG. 64C.

<Insertion Step> FIG. 64A

When the endoscope insertion apparatus 402B is inserted into the intestinal tract 409A, the wire 415 is in a loosened state and the outer-side arms 411 and inner-side arms 421 are pressed against the intestinal wall 409 by their own elastic force.

<Detachment Step> FIG. 64B

The surgeon releases the state in which the distal end portions 421X and distal end portions 411X press against the intestinal wall 409 by performing an operation to pull the wire 415 from the proximal end portion side. In this connection, it is not necessary for the surgeon to pull the wire 415 until entering a state in which the distal end portions 421X and distal end portions 411X are completely not in contact with the intestinal wall 409.

<Withdrawal Step> FIG. 64C

In the detachment step, the state in which the distal end portions 421X and distal end portions 411X of the endoscope insertion apparatus 402B press against the intestinal wall 409 is released. Consequently, the amount of friction between the distal end portions 411X and distal end portions 421X and the intestinal wall 409 is extremely small not only in, naturally, the insertion direction, but also in the withdrawal direction. Therefore, the surgeon can easily withdraw the endoscope insertion apparatus 402B from the intestinal tract 409A.

More specifically, according to the endoscope insertion apparatus 402B, the surgeon can easily withdraw the endoscope insertion apparatus 402B by manipulating the wire 415 from the proximal end portion side.

In this connection, by placing the outer-side arms 411 and inner-side arms 421 in a reduced diameter state using the wire 415 in the initial insertion step also, the insertion operation is facilitated further. Further, a traction portion is not limited to a structure in which a single wire 415 is arranged from the proximal end portion side to the distal end portion side and back again to the proximal end portion side. For example, a traction portion may be configured with an annular wire of a size that is sufficient for arm members to enter an expanded diameter state, and a single wire that is connected to the annular wire and is inserted through the inside of the wire guide tube.

The endoscope insertion apparatus 402B of the present embodiment has the advantages of the endoscope insertion apparatus 402 of the second embodiment, and also has the advantage that a withdrawal operation is simple.

Fourth Embodiment

Hereunder, an endoscope insertion apparatus according to a fourth embodiment of the present invention is described using the drawings. An endoscope insertion apparatus 402C of the present embodiment is similar to the endoscope insertion apparatus 402 of the second embodiment. Hence, the same components are designated by the same symbols, and a description of such components is omitted below.

FIG. 65 is an oblique perspective view of an endoscope insertion apparatus according to the third embodiment.

As shown in FIG. 65, an endoscope insertion apparatus 402C of the present embodiment includes a cover section 413 that is a regulating member that regulates an axial distance between the distal end portion of the outer-side unit 410 and the distal end portion of the inner-side unit 420. In other words, the cover section 413 regulates the relative positions in the insertion direction of the outer-side arms 411 and the inner-side arms 421. The cover section 413 is a member such as a bellows-like member that has a structure that can expand and contract in an axial direction in which the outer-side unit 410 and the inner-side unit 420 advance and retract with respect to each other, and has the advantage of preventing dirt or the like from entering a gap at a position at which the outer-side unit 410 is mounted on the inner-side unit 420.

Further, the cover section 413 can prevent the outer-side unit 410 and the inner-side unit 420 from separating more than necessary. More specifically, even if the surgeon performs an operation to move the outer-side unit 410 or the inner-side unit 420 to a degree greater than necessary, the outer-side unit 410 or the inner-side unit 420 can only move within a predetermined because of the action of the cover section 413.

According to the endoscope insertion apparatus 402C that includes the cover section 413 that regulates the relative positions of the inner-side unit 420 and the outer-side unit 410 in the direction of the axis of advancement and retraction, the surgeon can perform an operation to move the outer-side unit 410 or the inner-side unit 420 without being concerned about the operation amount.

In this connection, although an example is illustrated in FIG. 65 in which the cover section 413 as a regulating member is provided between the outer-side unit 410 and the inner-side unit 420, a configuration may also be adopted in which the cover section 413 is provided between the endoscope 403 and the outer-side unit 410.

The endoscope insertion apparatus 402C of the present embodiment has the advantages of the endoscope insertion apparatus 402 of the second embodiment, and also has favorable operability since advancing/retracting operations between the outer-side unit 410 and the inner-side unit 420 can be efficiently performed. Further, because dirt or the like does not enter a gap between the outer-side unit 410 and the inner-side unit 420, troubles are not liable to occur in the endoscope insertion apparatus 402C.

Fifth Embodiment

Hereunder, an endoscope insertion apparatus according to a fifth embodiment of the present invention is described using the drawings. An endoscope insertion apparatus 402D of the present embodiment is similar to the endoscope insertion apparatus 402 of the second embodiment. Hence, the same components are designated by the same symbols, and a description of such components is omitted below.

FIG. 66 is a front view of an endoscope insertion apparatus according to a fifth embodiment of the present invention. As shown in FIG. 66, the endoscope insertion apparatus 402D of the present embodiment has three inner-side arms 421A to 421C and three outer-side arms 411A to 411C.

The endoscope insertion apparatus 402D of the present embodiment has similar advantages to the endoscope insertion apparatus 402 of the second embodiment. More specifically, as long as the endoscope insertion apparatus of the present invention has two or more outer-side arm members and two or more inner-side arm members, advantages can be obtained. In this connection, since the outer-side arm members and the inner-side arm members are alternately arranged in the circumferential direction, the number of outer-side arm members and inner-side arm members is the same.

Sixth Embodiment

Hereunder, an endoscope insertion apparatus according to a sixth embodiment of the present invention is described using the drawings. An endoscope insertion apparatus 402E of the present embodiment is similar to the endoscope insertion apparatus 402 of the second embodiment. Hence, the same components are designated by the same symbols, and a description of such components is omitted below.

FIG. 67 is a schematic diagram as viewed from a lateral direction of the endoscope insertion apparatus according to the sixth embodiment of the present invention in a state in which the endoscope insertion apparatus is inserted inside an intestine.

Although inner-side arms 461 and outer-side arms 451 of the endoscope insertion apparatus 402E of the present embodiment do not have elasticity, the inner-side arms 461 and outer-side arms 451 are rotatably fixed to the body portion 422 or body portion 412 at unshown pivots. The endoscope insertion apparatus 402E also includes balloons 414 as inner-side elastic body portions and balloons 424 as outer-side elastic body portions that are inflatable and deflatable and that press the inner-side arms 461 and outer-side arms 451 to the intestinal wall 409. The balloons 424 are disposed so as not to obstruct the movement of an outer-side unit 410C.

The balloons 414 and balloons 424 are connected to an unshown inner-side fluid supply and discharge section and outer-side fluid supply and discharge section, respectively, and inflate when supplied with a fluid such as air, and deflate when the air or the like is discharged therefrom. When inflated, the balloons 414 and balloons 424 press the inner-side arms 461 and outer-side arms 451 to the intestinal wall 409. The elastic body portions are not limited to balloons, and a plate spring or helical spring or the like may also be used.

The endoscope insertion apparatus 402E of the present embodiment in which the inner-side insertion assisting section includes inner-side elastic body portions that press inner-side arm members to a duct wall and the outer-side insertion assisting section includes outer-side elastic body portion that press outer-side arm member to the duct wall has the advantages of the endoscope insertion apparatus 402 of the second embodiment. Furthermore, since the endoscope insertion apparatus 402E that has inner-side elastic body portions and outer-side elastic body portions that are inflatable and deflatable can control a force with which the inner-side arms 461 and outer-side arms 451 press the intestinal wall 409 by means of the degree of inflation of the balloons, and can also perform control so that arm members do not contact the intestinal wall 409 by means of deflation of the balloons, insertion and withdrawal operations can be performed more simply.

Sixth Embodiment

Hereunder, an endoscope insertion apparatus according to a sixth embodiment of the present invention is described using the drawings. An endoscope insertion apparatus 402F of the present embodiment is similar to the endoscope insertion apparatus 402 of the second embodiment. Hence, the same components are designated by the same symbols, and a description of such components is omitted below.

As shown in FIG. 68, in the endoscope insertion apparatus 402F of the present embodiment, a body portion 412D of an outer-side unit 410D has four elongated slit portions 479A to 479D that have a width that allows inner-side arms 481 to protrude therefrom. According to the endoscope insertion apparatus 402F, because of the existence of the slit portions 479A to 479D, distal end portions 471X and distal end portions 481X can move to an overlapping state in the insertion direction or can move to a state in which the distal end portions 471X and distal end portions 481X move forward and rearward with respect to each other in the insertion direction.

In other words, according to the endoscope insertion apparatus 402F, the distal end portions 471X and distal end portions 481X can move to at least an overlapping state in a direction that is perpendicular to the circumferential direction of the body portion 412, and preferably can move so as to pass by each other in the forward and rearward directions.

In this case, although a structure in which the distal end portion side of the slit portions 479 is provided as an open end is necessary in order to attach and detach the inner-side unit 420D to and from the outer-side unit 410D, this structure is not necessary after the outer-side unit 410D has been mounted to the outer circumferential portion of the inner-side unit 420D. Therefore, when it is not necessary to attach and detach the inner-side unit 420D to and from the outer-side unit 410D, the slit portions 479 may be elongated window portions in a roughly rectangular shape whose distal end portion side is closed. In other words, the slit portions 479 may be shaped like a comparatively wide window formed in the axial direction in a side surface of a tubular member of the outer-side unit 410D.

Further, after mounting the outer-side unit 410D to the outer circumferential portion of the inner-side unit 420D, for example, a ring-shaped member may be provided that fixes an open end of the distal side of the slit portions 479 and closes the open end.

In addition to having the advantages of the endoscope insertion apparatus 402 of the second embodiment, the endoscope insertion apparatus 402F of the present embodiment also has favorable operability since the endoscope insertion apparatus 402F has the outer-side arms 471 and inner-side arms 481 that are the same shape, more specifically, the same length, and hence the forces with which the outer-side arms 471 and the inner-side arms 481 press to the intestinal wall 409 are the same.

The endoscope insertion apparatus of the present invention can also be used as an endoscope for industrial use, and not just as an endoscope for medical use. More specifically, when the endoscope insertion apparatus of the present invention is used to insert an endoscope for industrial use into a deep part of pipes that are connected in a complex structure, particularly into pipes with a flexible structure, the same advantages are obtained as when an endoscope for medical use is inserted into a deep region of an intestine.

The endoscope insertion apparatus of the present invention as described above is as follows.

(1) An endoscope insertion apparatus for inserting an endoscope into an intestine of a subject, including:

an inner-side insertion assisting section in which a plurality of inner-side fixing sections that have an inner-side arm member that is changeable between an expanded diameter state and a reduced diameter state and that has a distal end portion that is pressed and fixed to an intestinal wall in the expanded diameter state are uniformly arranged in a circumferential direction;

an outer-side insertion assisting section in which a plurality of outer-side fixing sections that have an outer-side arm member that is changeable between an expanded diameter state and a reduced diameter state and that has a distal end portion that is pressed and fixed to an intestinal wall in the expanded diameter state are uniformly arranged in a circumferential direction, and in which slit portions that extend in a direction perpendicular to the circumferential direction and from which the inner-side arm members protrude when the outer-side insertion assisting section is mounted to an outer circumferential portion of the inner-side insertion assisting section are uniformly arranged in the circumferential direction between the outer-side fixing sections; and an insertion operation portion that causes the inner-side arm members and the outer-side arm members to perform a diameter-expanding operation or a diameter-reducing operation, and also changes relative positions between the inner-side insertion assisting section and the outer-side insertion assisting section to change a front/rear relationship with respect to the insertion direction between the inner-side arm members and the outer-side arm members.

(2) An endoscope insertion apparatus for inserting an endoscope into a duct, including:

an inner-side insertion assisting section in which inner-side arm members that press a duct wall by means of an elastic force in a condition in which an amount of friction in an insertion direction with respect to the duct wall of distal end portions of the inner-side arm members is less than an amount of friction in a withdrawal direction are uniformly arranged in a circumferential direction on a distal end side of an inner-side insertion assisting section body portion; and an outer-side insertion assisting section in which outer-side arm members that press the duct wall by means of an elastic force in a condition in which an amount of friction in an insertion direction with respect to the duct wall of distal end portions of the outer-side arm members is less than an amount of friction in a withdrawal direction are uniformly arranged in a circumferential direction on a distal end side of an outer-side insertion assisting section body portion, and that is mounted to an outer circumferential portion of the inner-side insertion assisting section such that the inner-side arm members and the outer-side arm members are alternately arranged in a circumferential direction, and that advances and retracts on the same axis as the inner-side insertion assisting section;

wherein the distal end portions of the outer-side arm members and the distal end portions of the inner-side arm members can move to an overlapping state in the insertion direction or can move to a state in which the distal end portions of the outer-side arm members and the distal end portions of the inner-side arm members move forward and rearward with respect to each other in the insertion direction.

Further, a method of inserting the endoscope insertion apparatus of the present invention is as follows.

(1) A method of inserting an endoscope insertion apparatus that inserts an endoscope into an intestinal tract of a subject, including:

an initial insertion step of inserting into an intestinal tract:

an inner-side insertion assisting section in which a plurality of inner-side fixing sections having an inner-side arm member that is changeable between an expanded diameter state and a reduced diameter state and that has a distal end portion that is pressed against an intestinal wall in the expanded diameter state are uniformly arranged in a circumferential direction, and an outer-side insertion assisting section in which a plurality of outer-side fixing sections having an outer-side arm member that is changeable between an expanded diameter state and a reduced diameter state and that has a distal end portion that is pressed against an intestinal wall in the expanded diameter state are uniformly arranged in a circumferential direction, and in which slit portions that extend in an axial direction and from which the inner-side arm members protrude when the outer-side insertion assisting section is mounted to an outer circumferential portion of the inner-side insertion assisting section are formed between the outer-side fixing sections;

an inner-side insertion assisting section fixing step of placing the inner-side fixing sections of the inner-side insertion assisting section in an expanded diameter state to press and fix the inner-side fixing sections against the intestinal wall;

an outer-side insertion assisting section advancing step of advancing the outer-side insertion assisting section to a deep region side until the outer-side arm members that are in a reduced diameter state move forward of the inner-side arm members with respect to the insertion direction;

an outer-side insertion assisting section fixing step of placing the outer-side arm members of the outer-side insertion assisting section in an expanded diameter state so that the outer-side arm members press the intestinal wall;

an inner-side insertion assisting section pressing release step of placing the inner-side arm members of the inner-side insertion assisting section in a reduced diameter state to thereby release a state in which the inner-side arm members press the duct wall; and an inner-side insertion assisting section advancing step of advancing the inner-side insertion assisting section until the inner-side arm members move forward of the outer-side arm members with respect to the insertion direction.

(2) The method of inserting an endoscope insertion apparatus according to (1) above, further including an intestinal tract shortening step of shortening the intestinal tract by placing the inner-side arm members and the outer-side arm members in an expanded diameter state, and performing an operation to pull the outer-side insertion assisting section and the inner-side insertion assisting section to a proximal end portion side.

(3) The method of inserting an endoscope insertion apparatus according to (1) or (2) above, in which, after the initial insertion step, at all times, at least either the inner-side arm members or the outer-side arm members are in the expanded diameter state.

(4) The method of inserting an endoscope insertion apparatus according to any one of (1) to (3) above, in which the inner-side insertion assisting section is an endoscope that has an image pickup section.

(5) The method of inserting an endoscope insertion apparatus according to any one of (1) to (3) above, in which the outer-side insertion assisting section is an endoscope that has an image pickup section.

(6) The method of inserting an endoscope insertion apparatus according to any one of (1) to (3) above, in which the inner-side insertion assisting section has an insertion channel portion through which an endoscope having an image pickup section can be inserted.

(7) The method of inserting an endoscope insertion apparatus according to any one of (1) to (6) above, in which at least any one operation among a position changing operation and an advancing/retracting operation with respect to the inner-side arm members and the outer-side arm members is automatically performed.

(8) The method of inserting an endoscope insertion apparatus according to any one of (1) to (7) above, in which the endoscope insertion apparatus includes a cover section that is formed of a flexible resin film and that covers the inner-side arm members and the outer-side arm members.

A method of using an endoscope insertion apparatus according to a separate embodiment of the present invention is as follows.

(1) A method of using an endoscope insertion apparatus for inserting an endoscope into a duct, including:

an initial insertion step of inserting into a duct:

an inner-side insertion assisting section in which inner-side arm members that press a duct wall by means of an elastic force in a condition in which an amount of friction in an insertion direction with respect to the duct wall of distal end portions of the inner-side arm members is less than an amount of friction in a withdrawal direction are uniformly arranged in a circumferential direction on a distal end side of an inner-side insertion assisting section body portion, and an outer-side insertion assisting section in which outer-side arm members that press the duct wall by means of an elastic force in a condition in which an amount of friction in an insertion direction with respect to the duct wall of distal end portions of the outer-side arm members is less than an amount of friction in a withdrawal direction are uniformly arranged in a circumferential direction on a distal end side of an outer-side insertion assisting section body portion, and that is mounted to an outer circumferential portion of the inner-side insertion assisting section such that the inner-side arm members and the outer-side arm members are alternately arranged in a circumferential direction, and that advances and retracts on the same axis as the inner-side insertion assisting section;

an inner-side insertion assisting section insertion step of inserting the inner-side insertion assisting section until the inner-side arm member distal end portions are in front of the outer-side arm member distal end portions with respect to the insertion direction; and an outer-side insertion assisting section insertion step of inserting the outer-side insertion assisting section until the outer-side arm member distal end portions are in front of the inner-side arm member distal end portions with respect to the insertion direction.

(2) The method of using an endoscope insertion apparatus according to (1) above, further including:

a separating step of releasing a pressing state of the inner-side arm members and the outer-side arm members with respect to the duct wall; and a withdrawing step of withdrawing from the duct the endoscope insertion apparatus in a state in which a pressing state of the inner-side arm members and the outer-side arm members with respect to the duct wall has been released.

(3) The method of using an endoscope insertion apparatus according to (1) or (2) above, in which the inner-side arm members of the endoscope insertion apparatus are longer than the outer-side arm members thereof in a direction of an axis on which the outer-side insertion assisting section advances and retracts.

(4) The method of using an endoscope insertion apparatus according to (1) or (2) above, in which the outer-side insertion assisting section body portion of the endoscope insertion apparatus has slit portions through which the inner-side arm members can protrude at a distal end portion of the outer-side insertion assisting section body portion.

The present invention is not limited to the above described embodiments and modification examples, and various changes and alterations are possible within a range that does depart from the spirit and scope of the present invention.

What is claimed is:

1. An endoscope insertion apparatus for inserting an endoscope into a duct, the endoscope insertion apparatus comprising:

inner-side arm members that press a duct wall;

an inner-side insertion assisting section in which the inner-side arm members are uniformly arranged in a circumferential direction on a distal end side of an inner-side insertion assisting section body portion;

outer-side arm members that press the duct wall; and an outer-side insertion assisting section mounted on an outer circumferential portion of the inner-side insertion assisting section, in which the outer-side arm members are uniformly arranged in a circumferential direction on a distal end side of an outer-side insertion assisting section body portion such that the inner-side arm members and the outer-side arm members are alternately arranged circumferentially around the outer-side insertion assisting section;

wherein the inner-side arm members can be changed between a reduced diameter state and an expanded diameter state in which the inner-side arm members press the duct wall, and the outer-side arm members can be changed between a reduced diameter state and an expanded diameter state in which the outer-side arm members press the duct wall, and the outer-side arm members and the inner-side arm members move forward and rearward with respect to each other in an insertion direction such that the outer-side arm members and the inner-side arm members alternately change between:

a state in which the outer-side arm members in the expanded diameter state change to the reduced diameter state and the inner-side arm members in the reduced diameter state change to the expanded diameter state, to thereby change a front/rear relationship with respect to the insertion direction between the outer-side arm members and the inner-side arm members; and a state in which the inner-side arm members in the expanded diameter state change to the reduced diameter state and the outer-side arm members in the reduced diameter state change to the expanded diameter state, to thereby change a front/rear relationship with respect to the insertion direction between the inner-side arm members and the outer-side arm members.

2. The endoscope insertion apparatus according to claim 1, wherein:

in the inner-side insertion assisting section, a plurality of inner-side fixing sections are uniformly arranged in a circumferential direction, the inner-side fixing sections comprising the inner-side arm members each of which is changeable between the expanded diameter state and the reduced diameter state, with distal end portions of the inner-side arm members being pressed and fixed to the duct wall in the expanded diameter state; and in the outer-side insertion assisting section, a plurality of outer-side fixing sections are uniformly arranged in a circumferential direction, the outer-side fixing sections comprising:

the outer-side arm members each of which is changeable between the expanded diameter state and the reduced diameter state, with distal end portions of the outer-side arm members being pressed and fixed to the duct wall in the expanded diameter state, and slit portions that extend in a direction perpendicular to the circumferential direction and from which the inner-side arm members protrude when the outer-side insertion assisting section is mounted to the outer circumferential portion of the inner-side insertion assisting section are uniformly arranged in the circumferential direction between the outer-side fixing sections;

the endoscope insertion apparatus further comprising:

an insertion operation portion that causes the inner-side arm members and the outer-side arm members to perform the diameter-expanding operation or the diameter-reducing operation, and to change the relative positions between the inner-side insertion assisting section and the outer-side insertion assisting section to thereby change the front/rear relationship with respect to the insertion direction between the inner-side arm members and outer-side arm members.

3. The endoscope insertion apparatus according to claim 2, further comprising:

an inner-side operation transmitting section that is connected to each of the inner-side arm members and that is capable of a pushing/pulling operation with respect to each of the inner-side arm members in the insertion direction; and an outer-side operation transmitting section that is connected to each of the outer-side arm members and that is capable of a pushing/pulling operation with respect to each of the outer-side arm members in the insertion direction;

wherein each of the inner-side arm members changes position between the expanded diameter state and the reduced diameter state by rotating around a corresponding inner-side insertion assisting section pivot as a result of the pushing/pulling operation of the inner-side operation transmitting section, and each of the outer-side arm members changes position between the expanded diameter state and the reduced diameter state by rotating around a corresponding outer-side insertion assisting section pivot as a result of the pushing/pulling operation of the outer-side operation transmitting section.

4. The endoscope insertion apparatus according to claim 3, wherein the insertion operation portion comprises:
an inner-side operation portion that operates the inner-side operation transmitting section and to which is connected an inner-side guide pipe through which the inner-side operation transmitting section is inserted; and
an outer-side operation portion that operates the outer-side operation transmitting section and to which is connected an outer-side guide pipe through which the outer-side operation transmitting section is inserted;
wherein the inner-side insertion assisting section and the outer-side insertion assisting section can be moved with respect to the insertion direction.

5. The endoscope insertion apparatus according to claim 3, wherein:
each of the inner-side arm members has an inner-side arm member cam groove that engages with a corresponding inner-side arm member cam pin that is moved by a pushing/pulling operation of the inner-side operation transmitting section, and is pivotally held by the corresponding inner-side insertion assisting section pivot; and
each of the outer-side arm members has an outer-side arm member cam groove that engages with a corresponding outer-side arm member cam pin that is moved by a pushing/pulling operation of the outer-side operation transmitting section, and is pivotally held by the corresponding outer-side insertion assisting section pivot.

6. The endoscope insertion apparatus according to claim 3, wherein:
each of the inner-side fixing sections has an inner-side elastic fixing section that retains each of the inner-side arm members in the reduced diameter state; and
each of the outer-side fixing sections has an outer-side elastic fixing section that retains each of the outer-side arm members in the reduced diameter state,
the endoscope insertion apparatus further comprising:
an inner-side operation transmitting section that is connected to each of the inner-side arm members and that changes a position of each of the inner-side arm members to the expanded diameter state by compressing the inner-side elastic fixing section by means of a pushing/pulling operation in a direction of the axis of advancement and retraction; and
an outer-side operation transmitting section that is connected to each of the outer-side arm members and that changes a position of each of the outer-side arm members to the expanded diameter state by compressing the outer-side elastic fixing section by means of a pushing/pulling operation in a direction of the axis of advancement and retraction.

7. The endoscope insertion apparatus according to claim 3, wherein:
each of the inner-side fixing sections has an inner-side inflation/deflation portion that is inflatable and deflatable and that retains each of the inner-side arm members in the expanded diameter state when inflated and retains each of the inner-side arm members in the reduced diameter state when deflated; and
each of the outer-side fixing sections has an outer-side inflation/deflation portion that is inflatable and deflatable and that retains each of the outer-side arm members in the expanded diameter state when inflated and retains each of the outer-side arm members in the reduced diameter state when deflated;
the endoscope insertion apparatus further comprising an inner-side supply and discharge section that supplies or discharges a fluid to or from the inner-side inflation/deflation portion, and an outer-side supply and discharge section that supplies or discharges a fluid to or from the outer-side inflation/deflation portion.

8. The endoscope insertion apparatus according to claim 3, further comprising a cover section that is formed using a flexible resin film and that covers a portion of the inner-side arm members and the outer-side arm members while exposing the distal end portions of the inner-side arm members and the distal end portions of the outer-side arm members.

9. The endoscope insertion apparatus according to claim 1, wherein:
in the inner-side insertion assisting section, inner-side arm members that press a duct wall by means of an elastic force in a condition in which an amount of friction in an insertion direction with respect to the duct wall of distal end portions of the inner-side arm members is less than an amount of friction in a withdrawal direction are uniformly arranged in a circumferential direction on the distal end side of the inner-side insertion assisting section body portion; and
in the outer-side insertion assisting section, outer-side arm members that press the duct wall by means of an elastic force in a condition in which an amount of friction in an insertion direction with respect to the duct wall of distal end portions of the outer-side arm members is less than an amount of friction in a withdrawal direction are uniformly arranged in a circumferential direction on the distal end side of the outer-side insertion assisting section body portion, and the outer-side insertion assisting section is mounted to the outer circumferential portion of the inner-side insertion assisting section such that the inner-side arm members and the outer-side arm members are alternately arranged in a circumferential direction, and advances and retracts on a same axis as the inner-side insertion assisting section.

10. The endoscope insertion apparatus according to claim 9, wherein the inner-side arm members and the outer-side arm members are elastic bodies.

11. The endoscope insertion apparatus according to claim 10, wherein the inner-side arm members are longer than the outer-side arm members in an axial direction along which the outer-side insertion assisting section advances and retracts.

12. The endoscope insertion apparatus according to claim 9, wherein the outer-side insertion assisting section has slit portions through which the inner-side arm members protrude at the distal end side of the outer-side insertion assisting section body portion.

13. The endoscope insertion apparatus according to claim 9, further comprising a traction portion that draws the distal end portions of the inner-side arm members and the distal end portions of the outer-side arm members in a direction of a center of the axis of advancement and retraction, and releases a state in which the inner-side arm members and the outer-side arm members press the duct wall.

* * * * *